US008185367B2

(12) United States Patent  
Zhu et al.

(10) Patent No.: US 8,185,367 B2
(45) Date of Patent: May 22, 2012

(54) SYSTEMS AND METHODS FOR RECONSTRUCTING GENE NETWORKS IN SEGREGATING POPULATIONS

(75) Inventors: Jun Zhu, Redmond, WA (US); Eric E. Schadt, Kirkland, WA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 882 days.

(21) Appl. No.: 11/587,900

(22) PCT Filed: May 2, 2005

(86) PCT No.: PCT/US2005/015419
§ 371 (c)(1), (2), (4) Date: Jul. 30, 2008

(87) PCT Pub. No.: WO2005/107412
PCT Pub. Date: Nov. 17, 2005

(65) Prior Publication Data
US 2008/0294403 A1   Nov. 27, 2008

Related U.S. Application Data

(60) Provisional application No. 60/567,075, filed on Apr. 30, 2004.

(51) Int. Cl.
G06G 7/58 (2006.01)
(52) U.S. Cl. ......................................................... 703/11
(58) Field of Classification Search .................... 703/11
See application file for complete search history.

(56) References Cited

U.S. PATENT DOCUMENTS

| 5,075,217 | A | 12/1991 | Weber |
| 5,324,631 | A | 6/1994 | Helentjaris et al. |
| 5,510,270 | A | 4/1996 | Fodor et al. |
| 5,569,588 | A | 10/1996 | Ashby et al. |
| 5,578,832 | A | 11/1996 | Trulson et al. |
| 5,965,352 | A | 10/1999 | Stoughton et al. |
| 6,132,969 | A | 10/2000 | Stoughton et al. |
| 6,132,997 | A | 10/2000 | Shannon |
| 6,165,709 | A | 12/2000 | Friend et al. |
| 6,218,122 | B1 | 4/2001 | Friend et al. |
| 6,271,002 | B1 | 8/2001 | Linsley et al. |
| 6,324,479 | B1 | 11/2001 | Friend et al. |
| 6,368,806 | B1 | 4/2002 | Openshaw et al. |
| 7,035,739 | B2 | 4/2006 | Schadt et al. |
| 2002/0094532 | A1 | 7/2002 | Bader et al. |
| 2003/0180761 | A1 | 9/2003 | Castonguay et al. |
| 2003/0224394 | A1 | 12/2003 | Schadt et al. |
| 2006/0111849 | A1 | 5/2006 | Schadt et al. |
| 2006/0122816 | A1 | 6/2006 | Schadt et al. |
| 2006/0241869 | A1 | 10/2006 | Schadt et al. |
| 2007/0038386 | A1 | 2/2007 | Schadt et al. |
| 2007/0166707 | A1 | 7/2007 | Schadt et al. |
| 2007/0185656 | A1 | 8/2007 | Schadt |

FOREIGN PATENT DOCUMENTS

| WO | WO 99/13107 | 3/1999 |
| WO | WO 03/065282 | 8/2003 |
| WO | WO 03/100557 | 12/2003 |
| WO | WO 2004/013727 | 2/2004 |
| WO | WO 2004/061616 | 7/2004 |
| WO | WO 2004/109447 | 12/2004 |
| WO | WO 2005/017652 | 2/2005 |
| WO | WO 2005/107412 | 2/2005 |

OTHER PUBLICATIONS

U.S. Appl. No. 11/986,001, filed Nov. 19, 2007, Schadt et al.
U.S. Appl. No. 11/985,979, filed Nov. 19, 2007, Schadt et al.
U.S. Appl. No. 11/527,145, filed Sep. 25, 2006, Schadt.
PCT/US05/15419, International Search Report, dated May 10, 2005.
PCT/US03/41613, International Search Report, dated Dec. 24, 2003.
PCT/US03/23976, International Search Report, dated Aug. 1, 2003.
PCT/US03/15768, International Search Report, dated May 20, 2003.
PCT/US03/03100, International Search Report, dated Februry 3, 2003.
PCT/USO4/17754, International Search Report, dated May 23, 2007.
Aitman et al., 1999, "Identification of Cd36 (Fat) as an insulin-resistance gene causing defective fatty acid and glucose metabolism in hypertensive rats," Nature Genetics 21: 76-83.
Akagi et al., 1996, "Microsatellite DNA markers for rice chromosomes," Theor. Appl. Genet. 93:1071-1077.
Allison et al., 1998, "Multiple phenotype modeling in gene-mapping studies of quantitative traits: power advantages," Am. J. Hum. Genet. 63:1190-1201.
Amos et al., 1990, "A multivariate method for detecting genetic linkage, with application to a pedigree with an adverse lipoprotein phenotype," Am. J. Hum. Genet. 47:247-254.
Barbosa et al., 1976, "The genetic heterogeneity of diabetes : histocompatibility antigens (HLA) in families with maturity-onset type diabetes of the young (MODY) and juvenile, insulin-dependent diabetes (JID) [proceedings]," Diabete. Metab. 2:160.
Blanchard et al., 1996, "Sequence to array: Probing the genome's secrets," Nature Biotechnology 14:1649.
Blanchard et al., 1996, "High-density oligonucleotide arrays," Biosensors & Bioelectronics 11: 687-690.

(Continued)

Primary Examiner — Jerry Lin
(74) Attorney, Agent, or Firm — Christensen O'Connor Johnson Kindness PLLC

(57) ABSTRACT

The reconstruction of genetic networks in mammalian systems is one of the primary goals in biological research, especially as such reconstructions relate to elucidating not only common, polygenic human disease, but living systems more generally. The present invention provides novel gene network reconstruction algorithms that utilize naturally occurring genetic variations as a source of perturbations to elucidate the networks. The algorithms incorporate relative transcript abundance and genotypic data from segregating populations by employing a generalized scoring function of maximum likelihood commonly used in Bayesian network reconstruction problems. The utility of these novel algorithms can be demonstrated via application to gene expression data from a segregating mouse population. The network derived from such data using the novel network reconstruction algorithm is able to capture causal associations between genes that result in increased predictive power, compared to more classically reconstructed networks derived from the same data.

9 Claims, 12 Drawing Sheets

OTHER PUBLICATIONS

Bligh et al, 1995, "A microsatellite sequence closely linked to the Waxy gene of *Oryza sativa*," Euphytica 86:83-85.

Bochner et al., 2001, "Phenotype microarrays for high-throughput phenotypic testing and assay of gene function," Genome Res. 11:1246-1255.

Börjeson, 1976, "The aetiology of obesity in children," Acta. Paediar. Scand. 65:279-287.

Bray, 1989, "1989 McCollum Award Lecture. Genetic and hypothalamic mechanisms for obesity-finding the needle in the haystack," Am. J. Clin. Nutr. 50:891-902.

Bray, 1992, "Genetic, hypothalamic and endocrine features of clinical and experimental obesity," Progress in Brain Research 93:333-341.

Brem et al., 2002, "Genetic Dissection of Transcriptional Regulation in Budding Yeast," Science 296:752-755.

Brown et al., 2000, "Knowledge-based analysis of microarray gene expression data by using support vector machines," Proc. Natl. Acad. Sci. USA 97:262-267.

Cheung et al., 2002, "The genetics of variation in gene expression," Nature Genetics Supplement 32:522-525.

Cheung et al., 2003, "Natural variation in human gene expression assessed in lymphoblastoid cells," Nature Genetics 33: 422-425.

Chirgwin et al., 1979, "Isolation of biologically active ribonucleic acid from sources enriched in ribonuclease," Biochemistry 18:5294-5299.

Cohen et al., 2000, "A computational analysis of whole-genome expression data reveals chromosomal domains of gene expression," Nature Genetics 26:183-186.

Corder et al., 1993, "Gene dose of apolipoprotein E type 4 allele and the risk of Alzheimer's disease in late onset families," Science 261:921-923.

Cox et al., 1999, "Loci on chromosomes 2 (NIDDMI) and 15 interact to increase susceptibility to diabetes in Mexican Americans," Nature Genetics 21:213-215.

Davis et al., 2005, "Ultrafine Mapping of SNPs From Mouse Strains C57BL/6J, DBA/2J, and C57BLKS/J for Loci Contributing to Diabetes and Atherosclerosis Susceptibility," Diabetes 54:1191-1199.

DeRisi et al., 1996, "Use of a cDNA microarray to analyse gene expression patterns in human cancer," Nature Genetics 14:457-460.

Doerge, 2002, "Mapping and analysis of quantitative trait loci in experimental populations," Nature Reviews 3:43-52.

Doss et al., 2005, "*Cis*-acting Expression Quantitative Trait Loci in Mice," Genome Research 15:681-691.

Draghici, 2003, "Data Analysis Tools for DNA Microarrays," Chapman & Hall, p. 1-478.

Duda et al., 2001, Pattern Classification, John Wiley & Sons, New York, NY, p. 521-530.

Duda et al., 2001, Pattern Classification, John Wiley & Sons, New York, NY, p. 550-557.

Easton et al., 1993, "Inherited susceptibility to breast cancer," Cancer Surv. 18:95-113.

Eaves et al., 2002, "Combining Mouse Congenic Strains and Microarray Gene Expression Analyses to Study a Complex Trait: The NOD Model of Type 1 Diabetes," Genome Research 12: 232-243.

Egholm et al., 1993, "PNA hybridizes to complementary oligonucleotides obeying the Watson-Crick hydrogen-bonding rules," Nature 365:566-568.

Elowitz et al., 2002, "Stochastic Gene Expression in a Single Cell," Science 297:1183-1186.

Falk et al., 1987, "Haplotype relative risks: an easy reliable way to construct a proper control sample for risk calculations," Ann. Hum. Genet. 51 ( Pt 3):227-233.

Ferguson et al., 1996, "A fiber-optic DNA biosensor microarray for the analysis of gene expression," Nature Biotechnology 14:1681-1684.

Fiehn et al., 2000, "Metabolite profiling for plant functional genomics," Nature Biotech. 18:1157-1161.

Fishel et al., 1993, "The human mutator gene homolog MSH2 and its association with hereditary nonpolyposis colon cancer," Cell 75:1027-1038.

Fodor et al., 1991, "Light-directed, spatially addressable parallel chemical synthesis," Science 251:767-773.

Ford et al., 1994, "Risks of cancer in BRCA1-mutation carriers. Breast Cancer Linkage Consortium," Lancet 343:692-695.

Friedman et al., 1991, "Molecular mapping of obesity genes," Mammalian Genome 1:130-144.

Friedman et al., 1992, "Tackling a weighty problem," Cell 69:217-220.

Froehler et al., 1986, "Synthesis of DNA via deoxynucleoside H-phosphonate intermediates," Nucleic Acids Research 14:5399-5407.

Fulker et al., 1999, "Combined Linkage and Association Sib-Pair Analysis for Quantitative Traits," Am. J. Hum. Genet. 64:259-267.

Fullerton et al., 2000, "Apolipoprotein E variation at the sequence haplotype level: implications for the origin and maintenance of a major human polymorphism," Am. J. Hum. Genet. 67:881-900.

Gaasterland et al., 2000, "Making the most of microarray data," Nature Genetics 24:204-206.

Ghazalpour et al., 2005, "Genomic analysis of metabolic pathway gene expression in mice," Genome Biology 6:R59.

Goffeau et al., 1996, "Life with 6000 genes," Science 274:546-567.

Grunau et al., 2001, "MethDB—a public database for DNA methylation data," Nucleic Acids Research, 29: 270-274.

Grundy et al., 1990, "Metabolic and health complications of obesity," Dis. Mon. 36:641-731.

Haley et al., 1992, "A simple regression method for mapping quantitative trait loci in line crosses using flanking markers," The Genetical Society of Great Britain 69:315-324.

Hayashi et al., 1994, "Detection of additive and dominance effects of QTLs in interval mapping of F2 RFLP data," Theor. Appl. Genet. 87:1021-1027.

Helentjaris et al., 1985, "Restriction fragment polymorphisms as probes for plant diversity and their development as tools for applied plant breeding," Plant Molecular Biology 5:109-118.

Helm et al., 1991, "Classification and identification of bacteria by Fourier-transform infrared spectroscopy," Journal of General Microbiology 137: 69-79.

Hu et al., 1991, "Identification of broccoli and cauliflower cultivars with RPD markers," Plant Cell Reports 10:505-511.

Hughes et al., 2000, "Functional Discovery via a Compendium of Expression Profiles," Cell 102:109-126.

International Human Genome Consortium, 2001, "Initial sequencing and analysis of the human genome," Nature 409:860-921.

James et al., 1998, "Non-alcoholic steatohepatitis (NASH): a disease of emerging identity and importance," Journal of Hepatology 29: 495-501.

Jansen, 1993, "Interval mapping of multiple quantitative trait loci," Genetics 135:205-211.

Jansen, 1994, "Controlling the type I and type II errors in mapping quantitative trait loci," Genetics 138:871-881.

Jansen et al., 2001, "Genetical genomics: the added value from segregation," TRENDS in Genetics 17:388-391.

Jarvis et al., 1973, "Clustering using a similarity measure based on shared near neighbors," IEEE Transactions on computers C-22:1025-1034.

Jaspers et al., 1982, "Genetic heterogeneity in ataxia-telangiectasia studied by cell fusion," Proc. Natl. Acad. 79: 2641-2644.

Jiang et al., 1995, "Multiple trait analysis of genetic mapping for quantitative trait loci," Genetics 140:1111-1127.

Jin et al., 2001, "The contributions of sex, genotype and age to transcriptional variance in *Drosophila melanogaster*," Nature Genetics 29: 389-395.

Kajiwara et al., 1994, "Digenic Retinitis Pigmentosa Due to Mutations at the Unlinked Peripherin/RDS and ROM1 Loci," Science 264: 1604-1608.

Karp et al., 2000, "Identification of complement factor 5 as a susceptibility locus for experimental allergic asthma," Nature Immunology, vol. 1, No. 3: 221-226.

Kearsey et al., 1994, "QTL analysis: a simple 'marker-regression' approach," Theor. Appl. Genet. 89:698-702.

Knapp et al., 1993, "The haplotype-relative-risk (HRR) method for analysis of association in nuclear families," Am. J. Hum. Genet. 52:1085-1093.

Knoll et al., 1993, "Cytogeneitc and Molecular Studies in the Prader-Willi and Angelman Syndromes: An Overview," Amer. Journal of Medical Genetics 46: 2-6.
Kraft et al., 2003, "A Family-Based Test for Correlation Between Gene Expression and Trait Values," The American Society of Human Genetics 72:1323-1330.
Kruglyak et al., 1996, "Parametric and nonparametric linkage analysis: a unified multipoint approach," Am. J. Hum. Genet. 58:1347-1363.
Kruglyak et al., 2001, "Variation is the spice of life," Nature Genetics 27:234-236.
Lance et al., 1967, "A general theory of classificatory sorting strategies," Computer Journal 9:373-380.
Lander et al., 1989, "Mapping Mendelian factors underlying quantitative traits using RFLP linkage maps," Genetics 121:185-199.
Lander et al., 1994, "Genetic dissection of complex traits," Science 265:2037-2048.
Lander, 1996, "The new genomics: Global views of biology," Science 274:536-539.
Levsky et al., 2002, "Single-Cell gene expression profiling," Science 297:836-840.
Lockhart et al., 1996, "Expression monitoring by hybridization to high-density oligonucleotide arrays," Nature Biotechnology 14:1675-1680.
Lynch et al., 1998, "Genetics and Analysis of Quantitative Traits," Sinauer Associates, Inc.: 431-484.
Machleder et al., 1997, "Complex Genetic Control of HDL Levels in Mice in Response to an Atherogenic Diet," J. Clin. Invest. 99:1406-1419.
Manley et al., 1999, "Overview of QTL mapping software and introduction to Map Manager QT," Mammalian Genome 10:327-334.
Martinez et al., 1994, "Missing markets when estimating quantitative trait loci using regression mapping," The Genetical Society of Great Britain 73:198-206.
Maskos et al., 1992, "Oligonucleotide hybridisations on glass supports: a novel linker for oligonucleotide synthesis and hybridisation properties of oligonucleotides synthesised in situ," Nucleic Acids Research 20: 1679-1684.
McBride et al., 1983, "An Investigation of Several Deoxynucleoside Phosphoramidites Useful for Sythesizing Deoxyoligonucleotides," Tetrahedron Letters 24: 245-248.
Moll et al., 1991, "The Genetic and Environmental Sources of Body Mass Index Variability: Te Muscatine Ponderosity Family Study," Am. J. Hum. Genet. 49: 1243-1255.
Mount, 2001, "Genome Analysis," Bioinformatics Sequence and Genome Analysis Chapter 10, p. 479-531.
Naumann et al., 1991, "Microbiological characterizations by FT-IR spectroscopy," Nature 351: 81-82.
Nguyen et al., 1995, "Differential gene expression in the murine thymus assayed by quantitative hybridization of arrayed cDNA clones," Genomics 29:207-216.
Nishina et al., 1994, "Atherosclerosis in genetically obese mice: the mutants obese, diabetes, fat, tubby, and lethal yellow," Metabolism 43:554-558.
Olson et al., 1999, "Tutorial in biostatistics genetic mapping of complex traits," Statistics in Medicine 18:2961-2981.
Patil et al., 2001, "Blocks of limited haplotype diversity revealed by high-resolution scanning of human chromosome 21," Science 294:1719-1723.
Pease et al., 1994, "Light-generated oligonucleotide arrays for rapid DNA sequence analysis," Proc. Natl. Acad. Sci. 91: 5022-5026.
Pericak-Vance et al., 1991, "Linkage Studies in Familial Alzheimer Disease: Evidence for Chromosome 19 Linkage," Am. J. Hum. Genet. 48: 1034-1050.
Prashar et al., 1996, "Analysis of differential gene expression by display of 3' end restriction fragments of cDNAs," Proc. Natl. Acad. Sci. USA 93:659-663.
Reeders et al., 1987, "A study of genetic linkage heterogeneity in adult polycystic kidney disease," Hum. Genet. 76:348-351.
Roberts et al., 2000, "Signaling and Circuitry of Multiple MAPK Pathways Revealed by a Matrix of Global Gene Expression Profiles," Science 287: 873-880.

Sagliocco et al., 1996, "Identification of Proteins of the Yeast Protein Map using Genetically Manipulated Strains and Peptide-Mass Fingerprinting," Yeast 12: 1519-1533.
Sandberg et al., 2000, "Regional and strain-specific gene expression mapping in the adult mouse brain," PNAS 97: 11038-11043.
Schadt et al. 2004, A Comprehensive Transcript Index of the Human Genome Generated Using Microarrays and Computational Approaches, Genome Biology 5 R73.
Schadt et al., 2003, "Genetics of gene expression surveyed in maize, mouse and man," Nature 422:297-302.
Schadt et al., 2003, "A new paradigm for drug discovery: integrating clinical genetic, genomic and molecular phenotype data to identify drug targets," Biochemical Society Transactions 31:437-443.
Schena et al., 1996, "Parallel human genome analysis; microarray-based expression of 1000 genes," Proc. Natl. Acad. Sci. USA 93:10614-10619.
Schena et al., 1995, "Quantitative Monitoring of Gene Expression Patterns with a Complementary DNA Microarray," Science 270: 467-470.
Shalon et al., 1996, "A DNA microarray system for analyzing Complex DNA samples using two-color fluorescent probe hybridization," Genome Research 6:639-645.
Shevchenko et al., 1996, "Linking genome and proteome by mass spectrometry: Large-scale identification of yeast proteins from two dimensional gels," Proc. Natl. Acad. Sci. 93: 14440-14445.
Spielman et al., 1989, "Genetic Analysis of IDDM: Summary of GAW5 IDDM Results," Genetic Analysis of complex Traits, Part I: 43-58.
Steinmetz et al., 2002, "Dissecting the architecture of a quantitative trait locus in yeast," Nature 416:326-330.
St. George-Hyslop et al., 1990, "Genetic linkage studies suggest that Alzheimer's disease is not a single homogeneous disorder. FAD Collaborative Study Group," Nature 347:194-197.
Struss et al., 1998, "The use of microsatellite markers for detection of genetic diversity in barley populations," Theor. Appl. Genet. 97:308-315.
Stover, et al., 2001, "Characterization of Gene Expression Profiles in Peripheral Blood Mononuclear Cells and Bone Marrow of Normal Human Volunteers," FASEB Journal, 534.9: A696.
Stunkard et al., 1990, "The Body-Mass Index of Twins Who Have Been Reared Apart," New England Journal of Medicine 322: 1483-1487.
Tamayo et al., 1999, "Interpreting patterns of gene expression with self-organizing maps: Methods and application to hematopoietic differentiation," Proc. Natl. Acad. Sci. USA 96:2907-2912.
Terwilliger et al., 1992, "A haplotype-based 'haplotype relative risk' approach to detecting allelic associations," Hum. Hered. 42:337-346.
Thakurta et al., Sep. 15, 2006, "Cis-regulatory variations: A study of SNPs around genes showing cis-linkage in segregating mouse populations," BMC Genomics 7, 235.
Twine et al., 2003, "Disease-associated Expression Profiles in Peripheral Blood Mononuclear Cells from Patients with Advanced Renal Cell Carcinoma," Cancer Research 63: 6069-6075.
Velculescu et al., 1995, "Serial Analysis of Gene Expression," Science 270: 484-487.
Venter et al., 2001, "The Sequence of the Human Genome," Science 291: 1304-1351.
Weisblum et al., 1972, "Genetic Heterogeneity of Xeroderma Pigmentosum demonstrated by Somatic Cell Hybridization," Nature New Biology 238: 80-83.
Welsh et al., 1990, "Fingerprinting genomes using PCR with arbitrary primers," Nucleic Acids Research 18: 7213-7218.
Williams et al., 1999, "Joint multipoint linkage analysis of multivariate qualitative and quantitative traits," Am. J. Hum. Genet. 6:1134-1147.
Wu et al., 1993, "Abundance, polymorphism and genetic mapping of microsatellites in rice," Mol. Gen. Genet. 241:225-235.
Younossi et al., 2002, "Perspectives in Clinical Hepatology: Nonalcoholic Fatty Liver Disease: An Agenda for Clinical Research," Hepatology: 746-752.
Zeng, 1993, "Theoretical basis for separation of multiple linked gene effects in mapping quantitative trait loci," Proc. Natl. Acad. Sci. USA 90:10972-10976.

Zeng, 1994, "Precision mapping of quantitative trait loci," Genetics 136:1457-1468.

Chen et al., 2008, "Variations in DNA elucidate molecular networks that cause disease," Nature 452, 429-435.

Emilsson et al., 2008, "Genetics of gene expression and its effect on disease," Nature 452, 423-430.

Schadt et al., 2008, "Mapping the Genetic Architecture of Gene Expression in Human Liver," PLoS Biology 6, 1020-1032.

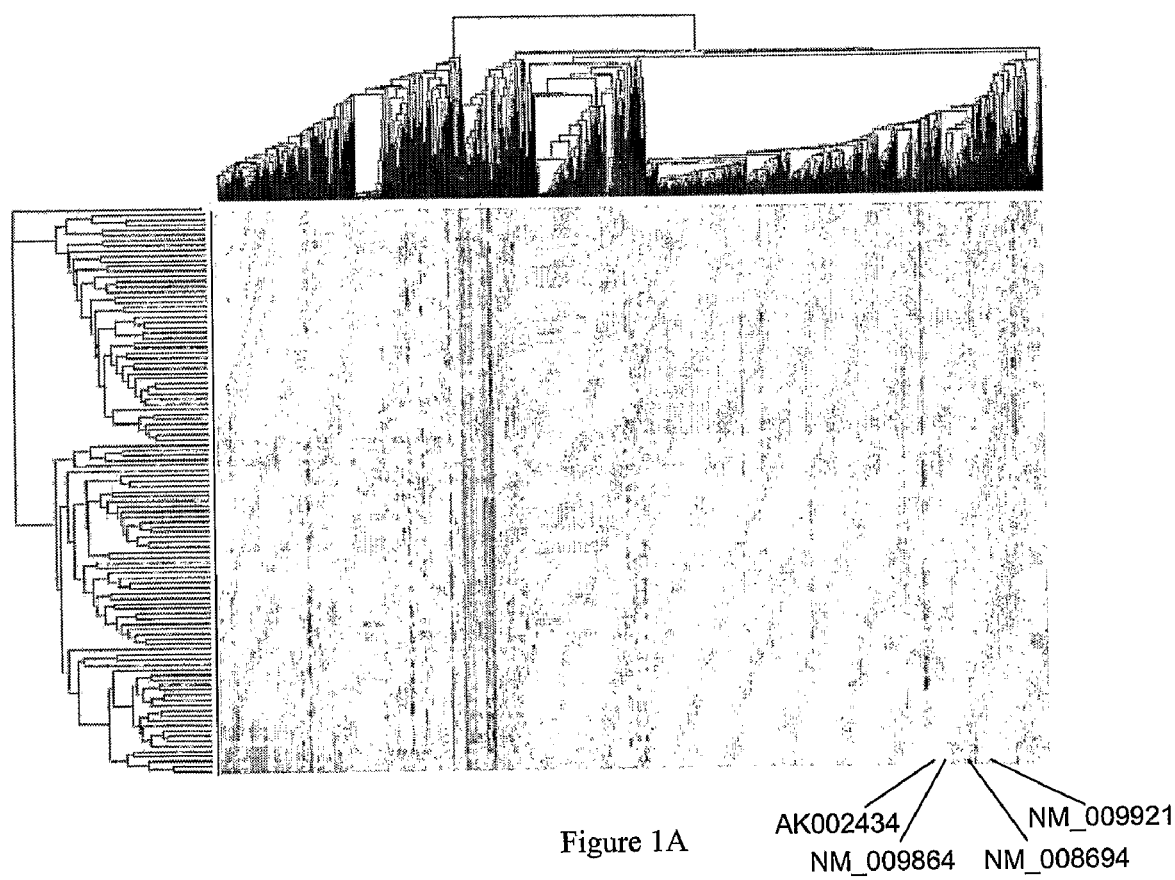
Figure 1A  AK002434 / NM_009921
NM_009864  NM_008694

SYSTEMS AND METHODS FOR RECONSTRUCTING GENE NETWORKS IN SEGREGATING POPULATIONS

CROSS-REFERENCE TO RELATED APPLICATION

This application claims benefit, under 35 U.S.C. §119(e), of U.S. Provisional Patent Application No. 60/567,075, filed on Apr. 30, 2004 which is incorporated herein, by reference, in its entirety.

FIELD OF THE INVENTION

The present invention relates to methods for reconstructing gene networks in segregating populations.

BACKGROUND OF THE INVENTION

Complex disease research has benefited significantly from the completion of the sequencing of several genomes and from high-throughput functional genomics technologies like microarrays for molecular profiling. The complete human and mouse genomic sequences have allowed researchers to more rapidly identify genes underlying susceptibility loci for common human diseases like schizophrenia and autoimmune disorders. See, for example, Stefansson et al., 2002, Am J Hum Genet 71: 877-892; and Ueda et al., 2003, Nature 423: 506-511. Further, gene expression microarrays and other high-throughput molecular profiling technologies have been used to identify complex disease subtypes, to directly identify genes underlying susceptibility loci for common human diseases like asthma and cytochrome c oxidase deficiency, and to identify biomarkers for clinical trials. See, for example, van 't Veer et al., 2002, Nature 415, 530-536; Schadt et al., 2003, Nature 422, 297-302; Karp et al., 2000, Nat Immunol 1, 221-226; and van de Vijver et al., 2002, New England Journal of Medicine 347, 1999-2009.

More recently, Schadt et al., 2003, Nature 422, 297-302, combined gene expression and genetic data in segregating populations to elucidate complex diseases by treating gene expression as a quantitative trait and mapping quantitative trait loci (QTL) for those traits in mouse models for common human diseases. By looking at patterns of co-localization between disease trait QTL and gene expression QTL, Schadt et al., 2003, Nature 422, 297-302, demonstrated how candidate genes for complex diseases can be identified in an objective fashion.

The integration of genotypic, transcription, and clinical trait data to elucidate pathways associated with complex disease traits can be modeled using graphical structures constructed from experimental data. Graphical models have the potential to efficiently identify and represent the key gene-gene interactions driving the complex disease traits. The causal inferences that can be derived from quantitative trait loci (QTL) data, where causality follows from the central dogma of biology (e.g., DNA variations lead to changes in transcription regulation/protein function, which in turn cause variations in disease phenotypes), provide a novel source of information that complement gene expression data and that can be incorporated into methods that seek to identify graphical models (gene networks) of gene interactions. Several approaches exist for the systematic study of biological systems that ultimately result in the construction of these graphical models. A number of methods utilize protein-protein binding information to construct gene networks. See, for example, Marcotte et al., 2001, Bioinformatics 17, 359-63; and Xenarios et al., 2002, Nucleic Acids Research 30, 303-305. These networks, termed association networks, establish gene-gene interactions by examining binding domains shared between protein pairs. While these approaches have been effective in associating genes involved in common pathways, they are not able to determine genes that are causative for other genes in a given pathway, nor are they able to predict outcomes of perturbations to a given system, thus limiting their utility.

Other methods used to systematically characterize interaction data include differential equations for dynamic systems and multiple linear equations for near steady-state systems. See, for example, Davidson et al., 2002, Science 295, 1669-1678; and Gardner et al., 2003, Science 301, 102-105. One drawback with these approaches is that they require extensive data and other quantitative information in addition to the gene expression data, making them suitable for only small, focused networks/pathways.

More recently, significant research interest has shifted to the use of Bayesian networks to study causal interaction networks of biological systems based on gene expression data from time series and gene knockout experiments, protein-protein interaction data derived from predicted genomics features, and on other direct experimental interaction data. See, for example, Pe'er et al., 2001, Bioinformatics 17 Suppl 1, S215-24, which is hereby incorporated by reference in its entirety. Bayesian networks represent acyclic directed graphs, and so are capable of not only depicting important interactions among genes, but they can also represent causal associations between genes since the graphs are directed. In the biological systems context the nodes of these graphs represent genes, and the edges are weighted and directed based on an associated set of conditional probabilities that represent the extent and direction of the association between nodes connected by an edge. The conditional probabilities can be represented by a discrete or continuous probability distribution. To estimate the conditional probabilities used to construct a Bayesian network, perturbations that cover all possible conditions are needed.

Typically, the multiple conditions needed to estimate the conditional probabilities are generated by "artificial" genetic perturbations, such as gene knock outs, transgenics, siRNA, and mutagenesis. Environmental perturbations such as changes in nutrition and temperature can also be used to perturb a network. See, for example, Ideker et al., 2001, Annual Review Genomics Human Genetics 2, 343-72, which is hereby incorporated by reference in its entirety. In addition to genetic and environmental perturbations, it is reasonable to assume a temporal dimension for any given experimental condition. Therefore, sampling a series of time points for a given experimental condition may represent multiple conditions that can be used to estimate conditional probabilities for network reconstruction. It has been demonstrated that when gene expression data are used to estimate these conditional probabilities over different time points, the causal relationships inferred from time series data may be less reliable than those derived from the competing methods just discussed, given absolute mRNA levels are confounded by variations in degradation rates among the different mRNA. See, for example, Gordon et al., 1988, Journal Biological Chemistry 263, 2625-2631, which is hereby incorporated by reference in its entirety.

To systematically study interaction networks in experimental systems, genes can be systematically knocked out, inhibited by drug compounds that target specific genes, or inhibited/activated using chemical or siRNA technologies for every gene in the system under study. Some of these techniques are time consuming and lack the multifactorial context needed to achieve many complex phenotypes of interest Chemical and siRNA inhibition can be accomplished efficiently, but these techniques frequently give rise to off-target effects that cannot be resolved without additional experimentation. See, for example, Jackson et al., 2003, Nature Biotechnology 21, 635-637, which is hereby incorporated by reference in its entirety.

Bayesian networks, or graphical models more generally, can be applied to gene expression data to reconstruct interaction networks. However, because of the limited expression data typically available for any particular system in a given state, network reconstruction processes typically result in the identification of multiple networks that explain the data equally well. In fact, in most cases, causal relationships cannot be reliably inferred from gene expression data alone, since for any particular network, changing the direction of the edge between any two genes has little effect on the model fit. To reliably infer causal relationships, additional information is required.

A need, therefore, exists for improved techniques for reconstructing gene networks.

SUMMARY OF THE INVENTION

The present invention provides improved techniques for reconstructing gene networks. In the present invention, patterns of overlapping gene expression quantitative trait loci (eQTL) are used in the estimation of the conditional probabilities used to construct a Bayesian network that represents a gene network. Patterns of overlapping gene eQTL have been used to help distinguish between gene expression changes representing downstream (e.g., reactive) effects and those representing upstream (e.g., causal) effects. See, for example, Schadt et al., 2003, Nature 422, 297-302, which is hereby incorporated by reference in its entirety. Here, to demonstrate the utility of eQTL data in the estimation of the conditional probabilities used to construct a Bayesian network, by way of example and not limitation, a large-scale liver microarray and genotypic data from the segregating mouse population described by Schadt et al. was used to establish criteria for discriminating among alternative interactions, and to guide reconstruction of an interaction network for the mouse liver system. The utility of the resulting network in this system was verified by examining the gene expression behavior of 11-beta hydroxysteroid dehydrogenase 1 (Hsd11b1) in the reconstructed network. The predictive capabilities of the network are assessed by comparing the set of genes predicted by the network to respond to perturbations in the expression of Hsd11b1, with the set of genes observed to change in response to activating the peroxisome proliferators activated receptor alpha (Ppara) using a Ppara agonist in an independent experiment, where the Hsd11b1 expression is down regulated in response to the Ppara agonist Further, by refining the predicted network based on these combined experimental results, it is shown how this data can be used to identify the key steps involved in Hsd11b1 regulating downstream responders.

One aspect of the invention provides a method for constructing a model of a biological pathway comprising a plurality of genes. In the method an eQTL vector for a gene X in the plurality of genes is obtained. Also, an eQTL vector for a gene Y in the plurality of genes is obtained. A prior $p(X \rightarrow Y)$ is constructed that represents a probability that gene X is upstream of gene Y in the biological pathway. The prior is constructed as:

$$p(X \rightarrow Y) = r(X, Y) \frac{N(Y)}{N(X) + N(Y)},$$

where N(Y) is a number of eQTL in the eQTL vector for the gene Y and N(X) is a number of eQTL in the eQTL vector for the gene X. Further r(X,Y) is a weight that represents a correlation between the eQTL vector for gene X and the eQTL vector for gene Y. The model of the biological pathway is computed using Bayesian analysis that incorporates the prior $p(X \rightarrow Y)$ constructed as set forth in the equation above. In some embodiments in accordance with this aspect of the present invention, this method is implemented in a computer program product or a computer.

Another aspect of the present invention provides a method for constructing a model of a biological pathway comprising a plurality of genes. The method comprises obtaining an eQTL vector for a gene X in the plurality of genes. An eQTL vector for a gene Y in the plurality of genes is also obtained. A prior $p(X \rightarrow Y)$ is constructed that represents a probability that gene X is upstream of gene Y in the biological pathway. The prior is constructed as:

$$p(X \rightarrow Y) = 0$$

when the following conditions hold true:
 (i) there is an eQTL in the eQTL vector for the gene Y that is coincident with the physical location of gene Y; and
 (ii) there is an eQTL in the eQTL vector for the gene X that is coincident with the physical location of gene Y.

In the method, the model of the biological pathway is computed using Bayesian analysis that incorporates the constructed prior $p(X \rightarrow Y)$. In some embodiments in accordance with this aspect of the present invention, this method is implemented in a computer program product or a computer.

Still another aspect of the present invention provides a method for constructing a model of a biological pathway comprising a plurality of genes. In the method, a plurality of eQTL vectors is obtained. Each eQTL vector represents a different gene in the plurality of genes. For each respective eQTL vector in the plurality of eQTL vectors, a correlation between the respective eQTL vector and the eQTL vector that represents gene Y is computed, thereby obtaining a correlation coefficient for each gene in the plurality of genes with respect to gene Y. The plurality of genes is then ranked by theses correlation coefficients with respect to gene Y, thereby forming a ranked list of genes that includes a gene X The prior $p(X \rightarrow Y)$, which represents a probability that gene X is upstream of a gene Y in the biological pathway, is constructed. The prior is constructed as:

$$p(X \rightarrow Y) = 0$$

when the correlation coefficient for gene X is below a threshold percentile in the ranked list of genes. The model of the biological pathway is then computed using Bayesian analysis that incorporates the prior constructed prior $p(X \rightarrow Y)$. In some embodiments in accordance with this aspect of the present invention, this method is implemented in a computer program product or a computer.

Yet another aspect of the invention provides a method for constructing a model of a biological pathway comprising a plurality of genes. The method comprises obtaining a plurality of eQTL vectors. Each eQTL vector represents a different gene in the plurality of genes. For each respective eQTL vector in the plurality of eQTL vectors, a measure of mutual information between the respective eQTL vector and the eQTL vector that represents gene Y is computed, thereby obtaining a mutual information score for each gene in the plurality of genes with respect to gene Y. The plurality of genes are then ranked by the mutual information score with respect to gene Y obtained in above, thereby forming a ranked list of genes that includes a gene X. A prior p(X→Y) is then constructed that represents a probability that gene X is upstream of a gene Y in the biological pathway. The prior is constructed as $$p(X \rightarrow Y) = 0$$

when the mutual information score for gene X is below a threshold percentile in the ranked list of genes. The model of the biological pathway is then constructed using Bayesian analysis that incorporates the prior p(X→Y) constructed above. In some embodiments in accordance with this aspect of the present invention, this method is implemented in a computer program product or a computer.

DETAILED DESCRIPTION OF THE INVENTION

Bayesian networks are a promising tool for analyzing gene expression patterns. First, they are particularly useful for describing processes composed of locally interacting components; that is, the value of each component directly depends on the values of a relatively small number of components. Second, statistical foundations for learning Bayesian networks from observations, and computational algorithms to do so, are well understood and have been used successfully in many applications. Finally, Bayesian networks provide models of causal influence. Although Bayesian networks are mathematically defined strictly in terms of probabilities and conditional independence statements, a connection can be made between this characterization and the notion of direct causal influence. (Heckerman et al., 1999, A Bayesian approach to causal discovery, in Cooper and Glymour, 141-166; Pearl and Verma, 1991, A theory of inferred causation, in *Principles of Knowledge Representation and Reasoning: Proc. Second International Conference*, 441-452; and Spirtes et al., 1993, *Causation, Prediction, and Search*, Springer-Verlag, New York, each of which is hereby incorporated by reference in its entirety). Although this connection depends on several assumptions that do not necessarily hold in gene expression data, the conclusions of Bayesian network analysis might be indicative of some causal connections in the data.

Figure 6:
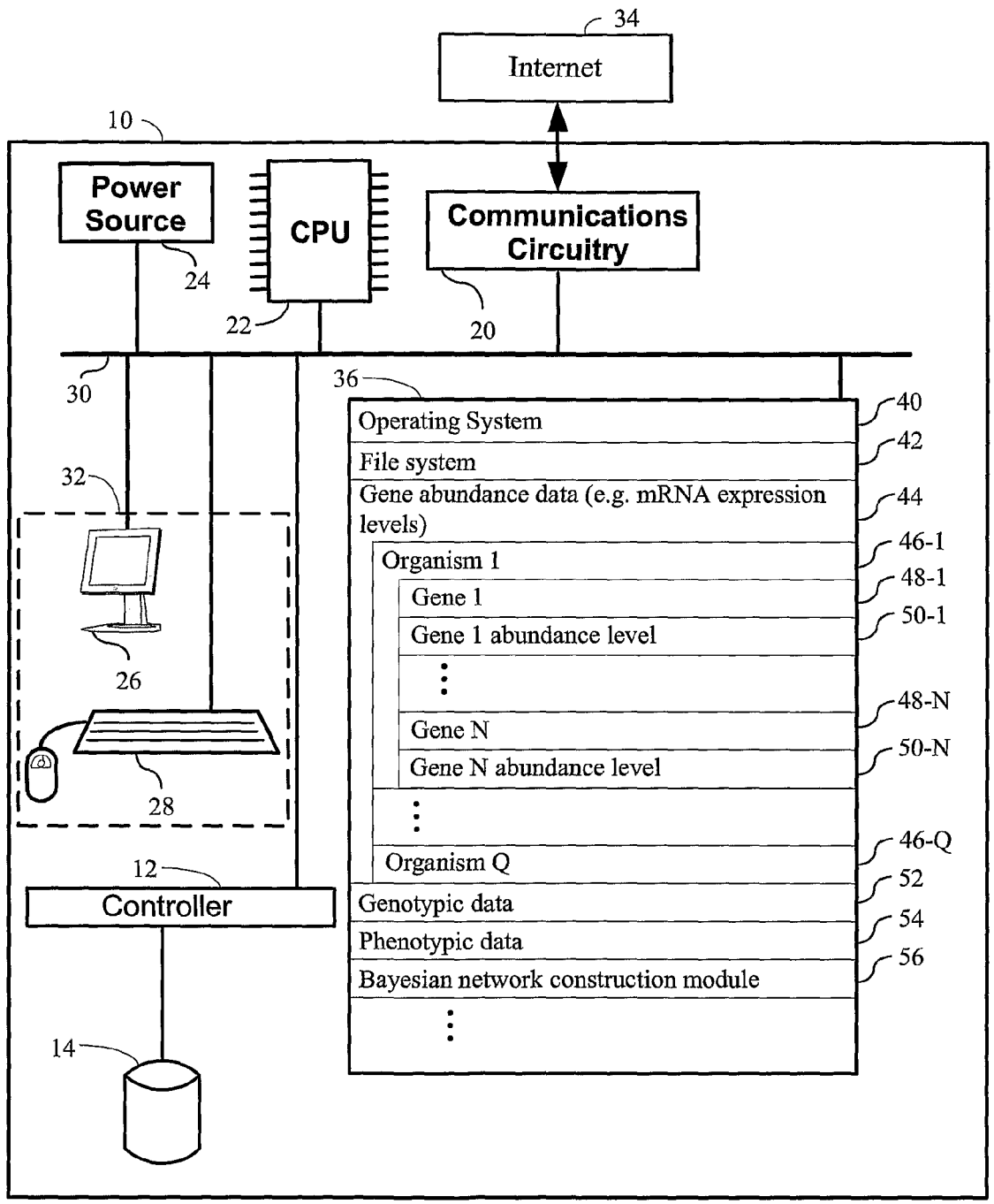
FIG. 6 illustrates a computer system in accordance with an embodiment of the present invention.
Figure 7A:
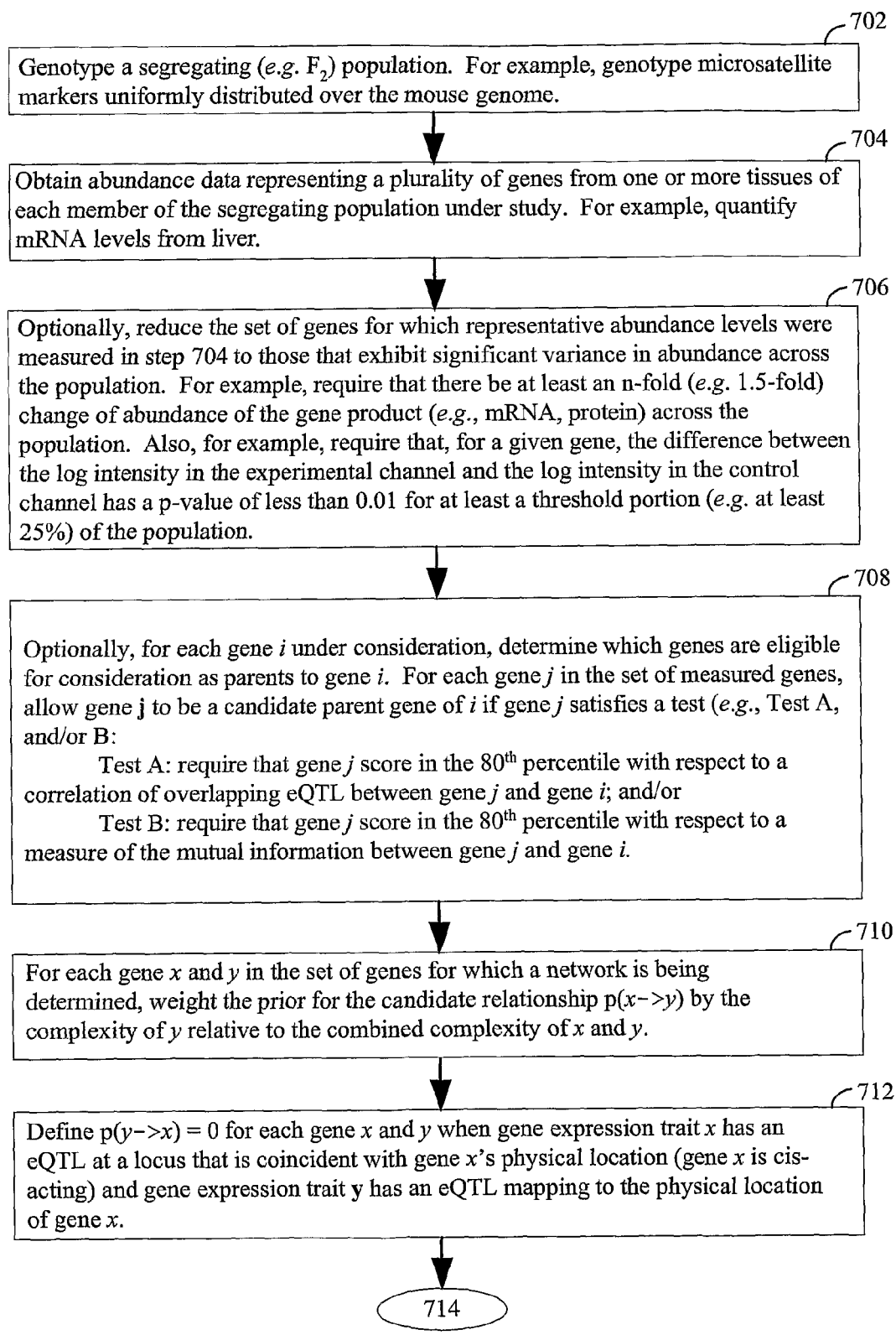
FIG. 7 illustrates an algorithm for reconstructing a gene network in accordance with an embodiment of the present invention.
Figure 7B:
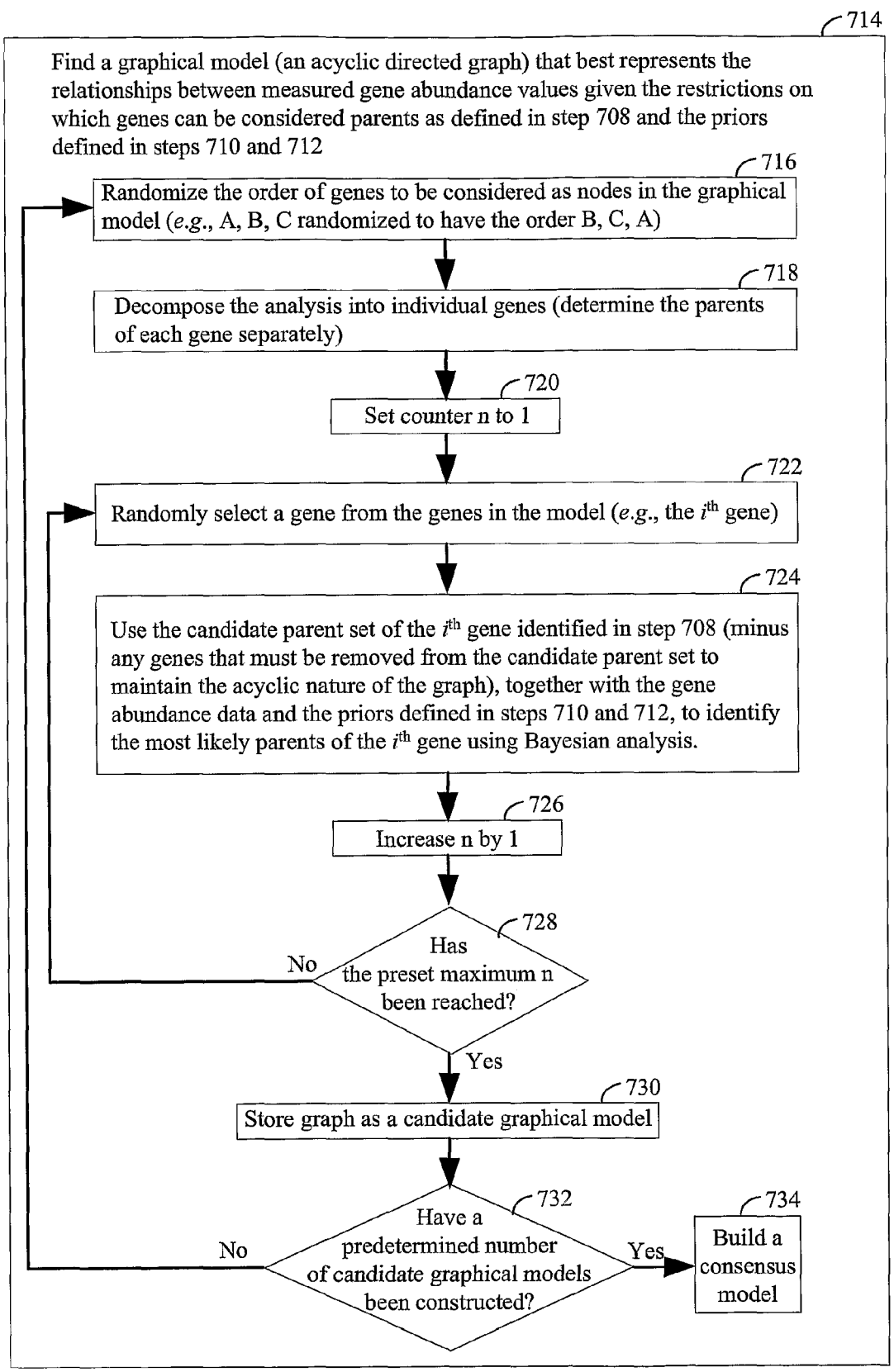

FIG. 6 illustrates a system 10 that is operated in accordance with one embodiment of the present invention. In addition, FIGS. 7A and 7B illustrate the processing steps that are performed in accordance with one embodiment of the present invention. These figures will be referenced in this section in order to disclose the advantages and features of the present invention. System 10 comprises standard components including a central processing unit 22, and memory 36 for storing program modules and data structures, user input/output device 32, a network interface 20 for coupling computer 10 to other computers via a communication network 34, and one or more busses 30 that interconnect these components. User input/output device 26 comprises one or more user input/output components such as a mouse, display 26, and keyboard 28. In some embodiments, some of the program modules and data structures are stored in a permanent storage device 14 that is controlled by controller 12. In some embodiments, device 14 is a hard disk. System 10 further includes a power source 24 to power the aforementioned components.

Memory 36 comprises a number of modules and data structures that are used in accordance with the present invention. It will be appreciated that, at any one time during operation of the system, a portion of the modules and/or data structures stored in memory 36 is stored in random access memory while another portion of the modules and/or data structures is stored in non-volatile storage 14. In a typical embodiment, memory 36 comprises an operating system 40. Operating system 40 comprises procedures for handling various basic system services and for performing hardware dependent tasks. Memory 24 further comprises a file system 42 for file management. In some embodiments, file system 42 is a component of operating system 40.

Exemplary Algorithm

Methods for reconstructing networks in accordance with the present invention are described in this section in conjunction with FIG. 7. In some embodiments, some of the steps described in this method are performed using Bayesian network reconstruction module 56 (FIG. 6).

Step 702.

The present invention begins with the step of obtaining genotype data 52. Genotype data 52 comprises the actual alleles for each genetic marker typed in each individual in a plurality of individuals under study. In some embodiments, the plurality of individuals under study is, for example, mice, cats, dogs, rabbits, pigs, cows, or corn. Genotype data 52 includes marker data at intervals across the genome under study or in gene regions of interest. Marker data comprises those markers that will be used in the population under study to assess genotypes. In one embodiment, marker data comprises the names of the markers, the type of markers, and the physical and genetic location of the markers in the genomic sequence. Exemplary types of markers include, but are not limited to, restriction fragment length polymorphisms "RFLPs", random amplified polymorphic DNA "RAPDs", amplified fragment length polymorphisms "AFLPs", simple sequence repeats "SSRs", single nucleotide polymorphisms "SNPs", microsatellites, etc.). Further, in some embodiments, marker data comprises the different alleles associated with each marker. For example, a particular microsatellite marker consisting of 'CA' repeats can represent ten different alleles in the population under study, with each of the ten different alleles, in turn, consisting of some number of repeats. Representative marker data in accordance with one embodiment of the present invention is found in Section 5.2, below.

In one embodiment of the present invention, the genetic markers used comprise single nucleotide polymorphisms (SNPs), microsatellite markers, restriction fragment length polymorphisms, short tandem repeats, DNA methylation markers, sequence length polymorphisms, random amplified polymorphic DNA, amplified fragment length polymorphisms, or simple sequence repeats.

In some embodiments, step 702 uses pedigree data. Pedigree data comprises the relationships between individuals in the population under study. The extent of the relationships between the individuals under study can be as simple as an inbred $F_2$ population, an $F_t$ population, an $F_{2:3}$ population, a Designer population, or as complicated as extended human family pedigrees. Exemplary sources of genotype and pedigree data are described in Section 5.2.

In some embodiments, a genetic map is generated from genotype data 52 and pedigree data. Such a genetic map includes the genetic distance between each of the markers present in genotype data 68. These genetic distances are computed using pedigree data. In some embodiments, the plurality of organisms under study represents a segregating population and pedigree data is used to construct the marker map. As such, in one embodiment of the present invention, genotype probability distributions for the individuals under study are computed. Genotype probability distributions take into account information such as marker information of parents, known genetic distances between markers, and estimated genetic distances between the markers. Computation of genotype probability distributions generally requires pedigree data. In some embodiments of the present invention, pedigree data is not provided and genotype probability distributions are not computed. In some embodiments, a genetic map is not constructed.

In some embodiments, the population that is used for the methods illustrated in FIG. 7 is a population that is derived from a select set of strains (e.g., a small, but diverse number of founding mice) or individuals (e.g., the Icelandic population, which was founded by a small to moderate number of individuals). In some embodiments, two strains of a species diverse with respect to complex phenotypes associated with human disease are chosen. In some embodiments, the species is mice. Representative human diseases include, but are not limited to, cancer, obesity, diabetes, atherosclerosis and associated morbidities, metabolic syndrome, depression/anxiety, osteoporosis, bone development, asthma, and chronic obstructive pulmonary disease. In one representative embodiment, the species under study is mice and all or a portion of the following strains are used: B6_DBA GTMs (Jake Lusis, University of California, Los Angeles), B6-CAST GTMs (Jake Lusis, University of California, Los Angeles), B6 DBA Consomics (Joe Nadaeu, Case Western Reserve University), AXB recombinant inbred (RI) lines (JAX, Bar Harbor Me.), BXA RI lines (JAX), LXS RI lines (Rob Williams, University of Tennessee), AKXD RI lines (JAX), 8-way cross mice (Rob Hitzmann, Oregon Health and Science University), D129S1/SvImJ (JAX), A/J (JAX), C57BL/6J (JAX), BALB/cJ (JAX), C3H/HeJ (JAX), CAST/Ei (JAX), DBA/2J (JAX), NOD/LtJ (JAX), NZB/B1NJ (JAX), SJL/J (JAX), AKR/J (JAX), CBA/J (JAX), FVB/NJ (JAX), and SWR/J (JAX).

In preferred embodiments, the species that is selected for study using the methods illustrated in FIG. 7 can be crossed. In such preferred embodiments, crosses (e.g. $F_2$ intercrosses) between pairs of the founding strains are performed. In some embodiments, rather than performing an $F_2$ intercross, other cross designs are used. For example, in some embodiments, a backcross or $F_2$ random mating scheme is employed. In some embodiments "random" intercrossing at the $F_1$ level is performed.

In some embodiments, the final segregating population size that is studied has a size of between 20 and 100 organisms, between 30 and 500 organisms, less than 500 organisms, or between 5 and 1000 organisms. In some embodiments, this population is treated as a single large pedigree and genotype information is collected from this population using a standard set of, for example, more 10, 20, 30, 40, 50, 70, or 100 markers. In some embodiments phenotypic data 56 is collected as well.

Step 704.

In step 704 abundance data 44 (e.g., from a gene expression study or a proteomics study) is obtained for a plurality of cellular constituents from one or more tissues in each member of the population under study. In some embodiments, cellular constituent abundance data 44 comprises the processed microarray images for each individual (organism) 46 in a population under study. For example, in one such embodiment, this data comprises, for each individual 46, gene transcript abundance information 50 for each gene 48 represented on the array, optional background signal information, and optional associated annotation information describing the probeset used for the respective gene (FIG. 1). See, for example, Section 5.3, below.

In various embodiments of the present invention, aspects of the biological state other than the transcriptional state, such as the translational state, the activity state, or mixed aspects can be measured and used as abundance data representing a plurality of genes. See, for example, Section 5.4, below. For instance, in some embodiments, abundance data 44 is, in fact, protein levels for various proteins in the organisms 46 under study. Thus, in some embodiments, abundance data comprises amounts or concentrations of the cellular constituent in tissues of the organisms under study, cellular constituent activity levels in one or more tissues of the organisms under study, the state of cellular constituent modification (e.g., phosphorylation), or other measurements relevant to the genes under study.

In one aspect of the present invention, the expression level of a gene in an organism in the population of interest is determined by measuring an amount of at least one cellular constituent that corresponds to the gene in one or more cells of the organism In one embodiment, the amount of the at least one cellular constituent that is measured comprises abundances of at least one RNA species present in one or more cells. Such abundances can be measured by a method comprising contacting a gene transcript array with RNA from one or more cells of the organism, or with cDNA derived therefrom. A gene transcript array comprises a surface with attached nucleic acids or nucleic acid mimics. The nucleic acids or nucleic acid mimics are capable of hybridizing with the RNA species or with cDNA derived from the RNA species. In one particular embodiment, the abundance of the RNA is measured by contacting a gene transcript array with the RNA from one or more cells of an organism in the plurality of organisms under study, or with nucleic acid derived from the RNA, such that the gene transcript array comprises a positionally addressable surface with attached nucleic acids or nucleic acid mimics, where the nucleic acids or nucleic acid mimics are capable of hybridizing with the RNA species, or with nucleic acid derived from the RNA species.

In some embodiments, cellular constituent abundance data 44 is taken from tissues that have been associated with a trait under study. For example, in one nonlimiting embodiment where the complex trait under study is human obesity, cellular constituent abundance data 44 is taken from the liver, brain, or adipose tissues. More generally, in some embodiments of the present invention, cellular constituent abundance data 44 is measured from multiple tissues of each organism 46 (FIG. 1) under study. For example, in some embodiments, cellular constituent abundance data 44 is collected from one or more tissues selected from the group of liver, brain, heart, skeletal muscle, white adipose from one or more locations, and blood. In such embodiments, the data is stored in a data structure such as data structure 78 of FIG. 11 of PCT application No. PCT/US2004/017754, filed Jun. 4, 2004, which is hereby incorporated by reference in its entirety.

In some embodiments, once abundance data has been assembled, the data is transformed into abundance statistics that are used to represent each gene in a plurality of genes under study. In some embodiments, between 100 and 1000 genes are under study. In some embodiments, between 200 and 40,000 genes are under study. In some embodiments, between 500 and 10,000 genes are under study. In some embodiments, between 1000 and 5,000 genes are under study. In some embodiments, between 500 and 3,000 genes are under study. In some embodiments, at least 40%, at least 50%, or at least 60% of the genes in the human genome are under study. In some embodiments, gene abundance data 44 (FIG. 1) comprises gene expression data for a plurality of genes (or cellular constituents that correspond to the plurality of genes). In one embodiment, the plurality of genes comprises at least five genes. In another embodiment, the plurality of genes comprises at least one hundred genes, at least one thousand genes, at least twenty thousand genes, or more than thirty thousand genes. The expression statistics commonly used as quantitative traits in the analyses in one embodiment of the present invention include, but are not limited to the mean log ratio, log intensity, and background-corrected intensity. In other embodiments, other types of expression statistics are used as quantitative traits. In one embodiment, the transformation of gene abundance data 44 is performed using a normalization module. In such embodiments, the expression levels of a plurality of genes in each organism under study are normalized. Any normalization routine can be used by normalization module 72. Representative normalization routines and error correction techniques that can be applied are described in Draghici, 2003, *Data Analysis Tools For DNA Microarrays*, CRC Press LLC, Boca Raton, Fla., which is hereby incorporated by reference in its entirety. Specifically, representative normalization routines include, but are not limited to, Z-score of intensity, median intensity, log median intensity, Z-score standard deviation log of intensity, Z-score mean absolute deviation of log intensity calibration DNA gene set, user normalization gene set, ratio median intensity correction, and intensity background correction. Furthermore, combinations of normalization routines can be used. Exemplary normalization routines in accordance with the present invention are disclosed in more detail in Section 5.5, below. Such expression statistics formed from the transformations can be stored in a abundance/genotype warehouse 78 described in application No. PCT/US2004/017754, filed Jun. 4, 2004, which is hereby incorporated by reference in its entirety.

Optional Step 706.

Abundance data for a large number of genes is measured in step 704. In optional step 706, the number of genes under consideration for reconstruction into a gene network is reduced by applying one or more filtering criteria. A first filtering criterion requires that those genes that exhibit abundance values that are significantly above background noise (e.g., P<0.05) be selected and all other genes excluded from further consideration. A second filtering criterion requires that those genes that exhibit abundance values that change at least 1.5-fold with an associated P-value less than 0.01 for at least 25% of the population be selected and all other genes excluded from further consideration. The present invention provides for variations on the first and second filtering criterion. In some embodiments, both criteria are imposed. In some embodiments, the threshold P valued used for first criterion is P=0.1, P=0.05 or P=0.001. In some embodiments, the threshold P valued used for second criterion is P=0.1, P=0.05, P=0.001, or P=0.0001. In some embodiments, the second filtering criterion requires a 2.0-fold change, a 2.5-fold change, a 3.0-fold change, or greater. In some embodiments, the second filtering criterion requires the percentage of population across which a fold-change must be exhibited is 25% or greater, 30% or greater, 35% or greater, 40% or greater, 45% or greater, 50% or greater, 55% or greater, or 60% or greater.

In some embodiment a filtering criterion is applied that requires that, for a given gene to be considered, the difference between the log intensity in the experimental channel and the log intensity in the control channel for the gene has a p-value of less than, for example, 0.01, for at least a threshold portion (e.g. at least 25%, at least 30%, at least 35%, at least 40%, at least 45%, at least 50%, at least 55%, or at least 60%) of the population.

Optional Step 708.

In preceding steps, abundance data for a plurality of genes from each member of a segregating population was measured. Optionally, the number of genes under consideration for reconstruction into a genetic network was reduced by applying one or more filtering criterion designed to limit the analysis to genes that differentially express across the population. In optional step 708, for each respective gene i that remains under consideration in the plurality of genes, a determination is made as to which genes in the plurality of genes can be considered as a parent node (a "parent gene") for the respective gene i. For a given gene i, such genes are referred to as the candidate parent set of the gene i. Genes in the candidate parent set of gene i qualify for consideration as the immediate parent of gene i. In typical embodiments, the candidate parent set of gene i is not used to determine relationships further upstream than the parent or parents of gene i. The goal of step 708 is not to identify the parent gene of gene i. Rather, the goal is to simply to limit the number of genes in the plurality of genes that can be evaluated to determine whether they are the parent of gene i. For instance, consider the case in which a total of 1088 genes remain after step 706. The goal is to construct a genetic network for the genes. In this genetic network, some genes will be parental genes (upstream) to other genes. In optional step 708, limits are placed on which genes can be evaluated to determined whether they are a parental gene of another gene. Thus, in optional step 708, for each gene j in the set of measured genes, allow gene j to be a candidate parent gene of if gene j satisfies a parental test. The present invention provides a number of parental tests. Two such parental tests (Parental test A and Parental test B) are described below. Any combination of these parental tests can be used to limit the candidate parent gene pool for a given gene in the plurality of genes for which a genetic network is to be constructed. In some embodiments, genes are eligible for consideration as parents of a given gene i if they satisfy parental test A or parental test B.

Parental test A. In parental test A, a requirement is imposed that gene j score in the $80^{th}$ percentile, or other chosen percentile, with respect to a correlation of overlapping eQTL vectors between gene j and gene i. This test is based on the premise that, if RNA levels for two genes are tightly associated, or if such levels are genetically controlled by a similar set of loci, then their eQTL should overlap. To appreciate this test, a description of how an eQTL vector is constructed for a gene should be understood. In some embodiments, the genome-wide eQTL computation described by Schadt et al., 2003, Nature 422, 297-302, hereby incorporated by reference in its entirety, was used. In some embodiments, the techniques described in Section 5.6 are used to construct an abundance statistics set 804 for each gene i under consideration. The extent of eQTL overlap, then, for two given genes is measured by computing the correlation coefficient between the corresponding abundance statistic sets 804 of the two genes.

In some embodiments, such correlations are computed as a weighted average of correlations for each individual chromosome:

$$r = \sum_c w(c) * r(c), \quad (1)$$

where r(c) is the correlation coefficient between the portion of the abundance statistics sets 804 for the two genes that fall on chromosome c, and w(c) is the chromosome-specific weight. The chromosome-specific correlation coefficient is given by:

$$r(c) = \frac{\sum_l x_c(l) * y_c(l) * I_c(l)}{\sum_l x_c(l) * x_c(l) + \sum_l y_c(l) * y_c(l)}. \quad (2)$$

In this equation, $x_c(l)$ and $y_c(l)$ are LOD scores at locus l (or other forms of statistical scores that signify the relationship between variance at a given locus and variance in abundance of a gene across a population) on chromosome c, and $I_c(l)$ is an indicator function defined as $$I_c(l) = \begin{cases} 1, \text{ if } x_c(l) > 1.5, y_c(l) > 1.5 \\ 0, \text{ otherwise} \end{cases}, \quad (3)$$

which was incorporated to eliminate low LOD scores (or any other such types of score used) that would have likely only contributed noise to the correlation measures. The chromosome-specific weight terms are given by:

$$w(c) = \max_l(\min(x_c(l),10)*\min(y_c(l),10)). \quad (4)$$

In effect, this equation provides for those chromosomes with high LOD scores (or other such types of scores used) to more significantly influence the overall correlation measure. This heuristic weight is intuitively appealing since gene expression traits with common significant eQTL have a larger percentage of their overall variation explained by these common genetic effects. For each gene under consideration, the correlation coefficients described above are computed for all genes in the set under consideration, and a predetermined percentile (e.g., $60^{th}$, $65^{th}$, $70^{th}$, $75^{th}$, $80^{th}$, $85^{th}$, $90^{th}$) of the rank-ordered list of correlations is arbitrarily chosen as the cutoff for genes to be considered as parental nodes in the network for a given gene of interest. For instance, if the $90^{th}$ percentile is chosen as the cutoff, only those genes scoring in the top 10 percentile are eligible for consideration as the parent under parental test A.

Parental test B. In parental test B, a requirement is imposed that gene j score in the $80^{th}$ percentile, or other chosen percentile, with respect to a measure of the mutual information between gene j and gene i. To differentiate between co-localization of QTL for a pair of traits due to common genetic effects (pleiotropy) versus multiple closely linked QTL, an assessment can be made of the extent of phenotypic (RNA levels) association using the mutual information measure:

$$\text{mi}(A, B) = \sum_{i,j} p(a_i, b_j) \log \frac{p(a_i, b_j)}{p(a_i)p(b_j)} \quad (5)$$

where p(x) is the probability density function for the expression of gene X in the system of interest. As in the case of the correlation calculations (Parental test A), the mutual information measure (Parental test B) can be computed for all gene pairs in the plurality of genes for which a network is sought, and the genes can be rank ordered. For example, consider the case in which gene i is among the plurality of genes for which a network is sought. To determine which genes can be considered parents of gene i, the respective mutual information score between gene i and each gene in the plurality of genes is computed. Thus, if there are 100 genes in the plurality of genes, 99 mutual information scores are computed. The 99 genes (all the genes other than gene i) are ranked ordered based on their mutual information scores and only the top predetermined percentile can be considered potential parents of gene i under parental test B. This process is repeated for each gene in the plurality of genes under consideration. In some embodiments, the predetermined percentile is, for example, the top $60^{th}$, $65^{th}$, $70^{th}$, $75^{th}$, $80^{th}$, $85^{th}$, or $90^{th}$ of the rank-ordered list. For instance, if the $90^{th}$ percentile is chosen as the cutoff, only those genes scoring in the top 10 percentile are eligible for consideration as the parent under parental test B.

Step 710.

By the time step 710 is reached, the plurality of genes for which network reconstruction is sought has been identified. In step 710, preparation begins for reconstruction of such networks by learning a Bayesian network. Before learning the Bayesian network, priors need to be constructed. As noted in Pearl, *Probabilistic Reasoning In Intelligent Systems Networks of Plausible Inference*, Morgan Kaufmann Publishers, Inc., San Francisco, Calif., which is hereby incorporated by reference, the inversion formula:

$$P(H\mid e) = \frac{P(e\mid H)P(H)}{P(e)}$$

states that the belief accorded a hypothesis H upon obtaining evidence e can be computed by multiplying a previous belief P(H) by the likelihood P(e|H) that e will materialize if H is true. P(H|e) is sometimes called the posterior probability (or simply posterior), and P(H) is called the prior probability (or prior).

As applied in the present invention, the goal is to identify a graphical model M (a gene network) that best represents the relationships between genes, given the gene expression data set, D, of interest. Here, D is the genes that remain under consideration after optional steps 706 and 708. Given data D, a search is conducted for the model M with the highest posterior probability P(M|D), where $$P(M\mid D) \propto P(D\mid M)P(M) \quad (6)$$

In this relationship, P(D|M) is the likelihood of D given M, and P(M) is the prior probability of model M $$P(M) = \prod_{X \to Y} p(X \to Y), \quad (7)$$

taken over all paths in the network (M) under consideration.

In step 710, priors p(X→Y) are constructed based on the relative complexity of the eQTL vectors for X and Y, where X and Y are two genes in the plurality of genes under consideration. The eQTL vector for a given gene is described in step 708, above, for "Parental test A." Complexity is best explained by example. Suppose gene expression trait X has two high confidence eQTL at loci $L_1$ and $L_2$ in its eQTL vector, while gene expression trait Y has a single eQTL at $L_1$ in its eQTL vector that is more significant than the eQTL for X at $L_1$. In this instance, it is reasonable to infer that Y controls X (or is "causal" for X), since if X were controlling Y it is expected that Y would have an eQTL at $L_2$ in addition to the eQTL a $L_1$, given X has an eQTL at $L_2$. Further, the asymmetry in the significance of the eQTL at $L_1$ for X and Y also favors Y as being causal for X. Thus, it is possible to use the eQTL overlap information to infer causality by defining the prior for a candidate relationship as:

$$p(X \to Y) = r(X, Y)\frac{N(Y)}{N(X) + N(Y)}, \quad (8)$$

where N is a gene expression trait's complexity as measured by the number of significant eQTL mapped for the given gene expression trait. Specifically, N(Y) is a number of eQTL in the eQTL vector for gene Y;

N(X) is a number of eQTL in the eQTL vector for gene X; and r(X,Y) is a weight that represents a correlation between the eQTL vector for said gene X and the eQTL vector for said gene Y. In some embodiments, this correlation is computed in accordance with equation (2), above. In some embodiments, $I_c(l)$ of equation (2) is as defined in equation (3) above. However, in other embodiments, $I_c(l)$ is computed with different criteria. For example, in various embodiments, $I_c(l)=1$ if $x_c(l)$ and $y_c(l)$ are each greater than 1.6, 1.7, 1.8, 1.9, 2.0, 2.1, 2.2, 2.3, 2.4, 2.5, 2.6, 2.7, 2.8, 2.9, 3.0 or greater and zero otherwise. In some embodiments $I_c(l)$ is always 1. If X and Y have coincident QTL (e.g., within a support interval, e.g., within 100 cM of each other, within 10 cM of each other, within 1 cM of each other, within 0.5 cM of each other, etc.), but the overall complexity of Y is greater than the overall complexity of X, then the inference can be made that X causes Y(X→Y), as opposed to Y→X. Implicit in this weighting scheme is the assumption that traits driven by common QTL are causally related (e.g., one trait drives the other), even though it is possible that the traits could be independently driven by the same set of QTL. However, in cases where multiple traits are independently driven by a common set of QTL, the correlation between the traits will be smaller than when the traits are causally related, so the prior will carry less weight. Further, the conditional mutual information measure discussed below will also serve to prevent, in at least some cases, causal links from being made between genes that are independently driven by a common set of QTL. In embodiments where the complexity of X and Y is equal the prior p(X→Y) is constructed by considering the relative strength of any eQTL that overlap in the eQTL vector for gene X and the eQTL vector for gene Y. For example, consider the case in which there is a solitary eQTL in the eQTL vector for gene X that overlaps with an eQTL in the eQTL vector for gene y. Then, for this one overlapping eQTL, the prior p(X→Y) is constructed, as p(X→Y)=(LodX/LodY)/(LodY/LodX+LodX/LodY)

For two overlaping eQTLs, the prior p(X→Y) is constructed, as p(X→Y)=prod(LodX$_i$/LodY$_i$)/(prod(LodY$_i$/LodX$_i$)+prod(LodX$_i$/LodY$_i$)).

In some embodiments, statistical scores other than Lod scores are used in such computations.

Step 712.

In step 712 additional priors were defined. Specifically, p(X→Y)=0 for each gene X and Y when gene expression trait X has an eQTL at a locus that is coincident with gene X's physical location (gene X is cis-acting) and gene expression trait Y has an eQTL mapping to the physical location of gene X. Such priors were set because of the following rational. If a gene expression trait X has an eQTL at locus L that is coincident with the gene's physical location, it can be stated that the gene has a cis-acting eQTL at L. This relationship indicates it is likely that DNA variations in the gene itself at least partially explain variations in the gene's observed RNA levels. Therefore, the inference can be made that a gene with a cis-acting eQTL is at least partially under the control of the gene itself. In this particular situation, where another gene expression trait Y has an eQTL mapping to the physical location of the cis-acting gene X, the inference can be made that X may be causal for Y, and that Y is likely not causal for X.

Steps 714, 716-732.

In step 714 a graphical model M (a gene network) that best represents the relationships between genes, given the gene expression data set, D, of interest and the priors defined in steps 710 and 712. Here, D is the genes that remain under consideration after optional steps 706 and 708. Thus, given data D, a search is conducted for the model M with the highest posterior probability P(M|D), where

P(M|D)∝P(D|M)P(M).

In this relationship, P(D|M) is the likelihood of D given M, and P(M) is the prior probability of model M $$P(M) = \prod_{X \to Y} p(X \to Y)$$

taken over all paths in the network (M) under consideration. FIG. 7B illustrates one method that can be used to compute a graphical model M. In fact, in the approach illustrated in FIG. 7B, a predetermined number of models M (see step 732 of FIG. 7B) are computed and each such model can be scored by computing P(M|D), where the priors developed in steps 710 and 712 are used. In some embodiments, the predetermined number in step 732 is 10 and therefore 10 candidate graphical models Mare computed. In other embodiments, 30 or more, 50 or more, 100 or more, 500 or more, or 1000 or more models Mare computed.

Central to the construction of a given model M is step 724, in which the candidate parent set of the $i^{th}$ gene identified in step 708, together with the gene abundance data and the priors defined in steps 710 and 712 is used, is the identification of the most likely parents of the $i^{th}$ gene. In some embodiments, the priors developed in steps 710 and 712 are used to find the most likely parent to the $i^{th}$ gene using the local maximum search algorithm implemented by Friedman et al., 2000, J. Comput Biol 7, 601-620, which is hereby incorporated by reference in its entirety, from among the candidate parent set determined for the $i^{th}$ gene in step 708.

Step 734.

In some embodiments, the plurality of networks constructed using the novel priors of the present invention, are used to construct a consensus gene network. This consensus network is derived from the plurality of networks by identifying links between gene pairs that existed in more than a predetermined percentage of the networks. In some embodiments, this predetermined percentage is 30% or more, 40% or more, 50% or more, or 60% or more of the networks (Models M computed in steps 716-732. Each link is assigned a confidence value corresponding to the number of times it appeared in the plurality of networks considered. Cycles in the resulting consensus network are broken by removing links in the cycle associated with the lowest confidence values.

Figure 2:
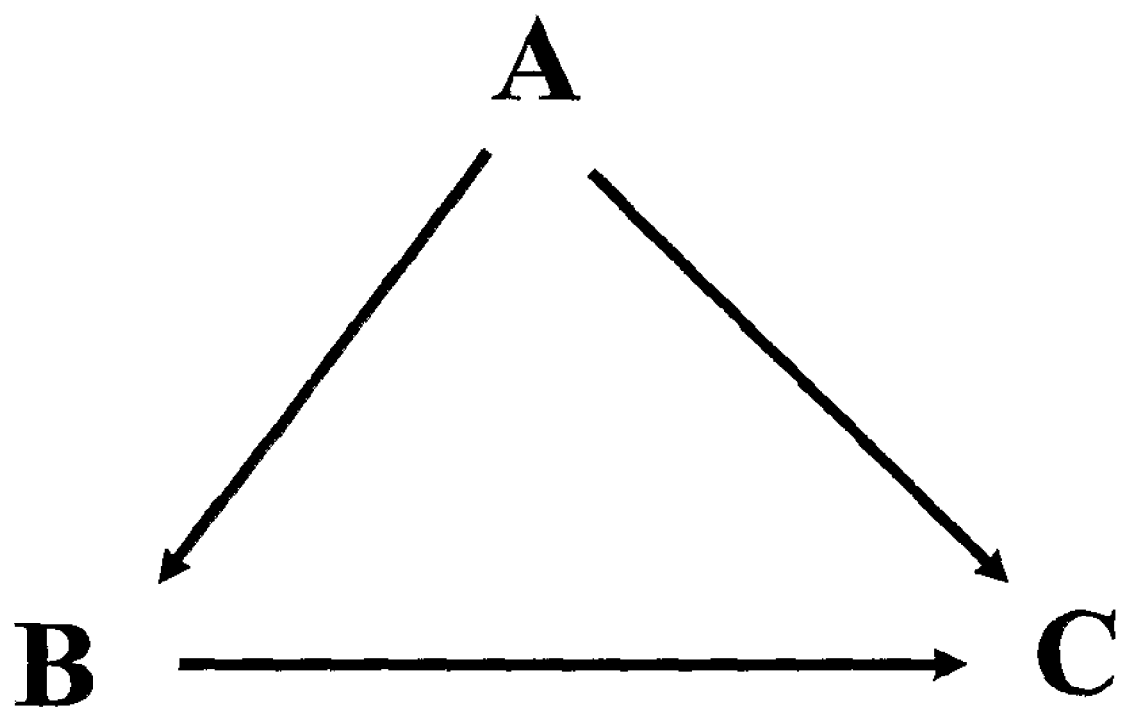
FIG. 2 illustrates an example of a sub-network that potentially over fits the data. Node A is seen as causal for nodes B and C, and node B is seen as causal for C. To determine whether the causal association between B and C is a consequence of A, the conditional mutual information between B and C given A is computed. If this value does not differ significantly from 0, then the link between B and C is removed.

In some embodiments, starting with the consensus network, identification of the most parsimonious model given the data is sought using maximum likelihood method. Although priors for network structure (e.g., the priors of steps 710 and 712) are introduced to penalize more complex topologies, there is still the possibility that optimal networks derived from this process over fit the data. To lessen the likelihood that the resulting networks in fact over fit the data, in some embodiments, links in the network are removed to simplify relationships among genes using a conditional information measure. For instance, if the type of sub-network shown in FIG. 2 is found to exist in the larger network, the conditional mutual information between B and C is computed to determine whether B and C are still found to be dependent given information on node A. The conditional mutual information in this instance was given by $$MI(B, C \mid A) = \sum_{i,j,k} p(b_i, c_j, a_k) \log\left(\frac{p(b_i, c_j \mid a_k)}{p(b_i \mid a_k) p(c_j \mid a_k)}\right). \quad (9)$$

If MI(B,C|A) are not significantly different from 0, then the link B→C can be safely removed.

Sources of Marker Data

Several forms of genetic markers that can be used in various implementations of Section 5.1 are known in the art. A common genetic marker is single nucleotide polymorphisms (SNPs). SNPs occur approximately once every 600 base pairs in the genome. See, for example, Kruglyak and Nickerson, 2001, Nature Genetics 27, 235, which is hereby incorporated by reference in its entirety. The present invention contemplates the use of genotypic databases such as SNP databases as a source of genetic markers. Alleles making up blocks of such SNPs in close physical proximity are often correlated, resulting in reduced genetic variability and defining a limited number of "SNP haplotypes" each of which reflects descent from a single ancient ancestral chromosome. See Fullerton et al., 2000, Am. J. Hum. Genet. 67, 881 which is hereby incorporated by reference in its entirety. Such haplotype structure is useful in selecting appropriate genetic variants for analysis. Patil et al. found that a dense set of SNPs is needed to capture all the common haplotype information. Once common haplotype information is available, it can be used to identify much smaller subsets of SNPs useful for comprehensive whole-genome studies. See Patil et al., 2001, Science 294, 1719-1723, which is hereby incorporated by reference in its entirety.

Other suitable sources of genetic markers include databases that have various types of gene expression data from platform types such as spotted microarray (microarray), high-density oligonucleotide array (HDA), hybridization filter (filter) and serial analysis of gene expression (SAGE) data. Another example of a genetic database that can be used is a DNA methylation database. For details on a representative DNA methylation database, see Grunau et al., 2001, Nucleic Acids Research 29, 270-274, which is hereby incorporated by reference in its entirety.

In one embodiment of the present invention, a set of genetic markers is derived from any type of genetic database that tracks variations in the genome of an organism of interest. Information that is typically represented in such databases is a collection of locus within the genome of the organism of interest. For each locus, strains for which genetic variation information is available are represented. For each represented strain, variation information is provided. Variation information is any type of genetic variation information. Representative genetic variation information includes, but is not limited to, single nucleotide polymorphisms, restriction fragment length polymorphisms, microsatellite markers, restriction fragment length polymorphisms, and short tandem repeats. Therefore, suitable genotypic databases include, but are not limited to:

TABLE 1

Representative genotypic databases

| Genetic variation type | Uniform resource location |
|---|---|
| SNP | http://bioinfo.pal.roche.com/usuka_bioinformatics/cgi-bin/msnp/msnp.pl |
| SNP | http://snp.cshl.org/ |
| SNP | http://www.ibc.wustl.edu/SNP/ |
| SNP | http://www-genome.wi.mit.edu/SNP/mouse/ |
| SNP | http://www.ncbi.nlm.nih.gov/SNP/ |
| Microsatellite markers | http://www.informatics.jax.org/searches/polymorphism_form.shtml |
| Restriction fragment length polymorphisms | http://www.informatics.jax.org/searches/polymorphism_form.shtml |
| Short tandem repeats | http://www.cidr.jhmi.edu/mouse/mmset.html |
| Sequence length polymorphisms | http://mcbio.med.buffalo.edu/mit.html |
| DNA methylation database | http://genome.imb-jena.de/public.html |
| Short tandem-repeat polymorphisms | Broman et al., 1998, Comprehensive human genetic maps: Individual and sex-specific variation in recombination, American Journal of Human Genetics 63, 861-869 |
| Microsatellite markers | Kong et al., 2002, A high-resolution recombination map of the human genome, Nat Genet 31, 241-247 |

Each database listed in Table 1 is hereby incorporated by reference in its entirety.

Another form of genetic marker that may be used in the present invention is restriction fragment length polymorphisms (RFLPs). RFLPs are the product of allelic differences between DNA restriction fragments caused by nucleotide sequence variability. As is well known to those of skill in the art, RFLPs are typically detected by extraction of genomic DNA and digestion with a restriction endonuclease. Generally, the resulting fragments are separated according to size and hybridized with a probe; single copy probes are preferred. As a result, restriction fragments from homologous chromosomes are revealed. Differences in fragment size among alleles represent an RFLP (see, for example, Helentjaris et al., 1985, Plant Mol. Bio. 5:109-118, and U.S. Pat. No. 5,324,631, each of which is hereby incorporated by reference in its entirety). Another form of genetic marker that may be used in the present invention is random amplified polymorphic DNA (RAPD). The phrase "random amplified polymorphic DNA" or "RAPD" refers to the amplification product of the distance between DNA sequences homologous to a single oligonucleotide primer appearing on different sites on opposite strands of DNA. Mutations or rearrangements at or between binding sites will result in polymorphisms as detected by the presence or absence of amplification product (see, for example, Welsh and McClelland, 1990, Nucleic Acids Res. 18:7213-7218; Hu and Quiros, 1991, Plant Cell Rep. 10:505-511, each of which is hereby incorporated by reference in its entirety).

Yet another form of genetic marker map that may be used in the present invention is amplified fragment length polymorphisms (AFLP). AFLP technology refers to a process that is designed to generate large numbers of randomly distributed molecular markers (see, for example, European Patent Application No. 0534858 A1, which is hereby incorporated by reference in its entirety). Still another form of genetic data that may be used in the present invention is "simple sequence repeats" or "SSRs". SSRs are di-, tri- or tetra-nucleotide tandem repeats within a genome. The repeat region may vary in length between genotypes while the DNA flanking the repeat is conserved such that the same primers will work in a plurality of genotypes. A polymorphism between two genotypes represents repeats of different lengths between the two flanking conserved DNA sequences (see, for example, Akagi et al., 1996, Theor. Appl. Genet. 93, 1071-1077; Bligh et al., 1995, Euphytica 86:83-85; Struss et al., 1998, Theor. Appl. Genet. 97, 308-315; Wu et al., 1993, Mol. Gen. Genet 241, 225-235; and U.S. Pat. No. 5,075,217, each of which are hereby incorporated by reference in their entirety). SSR are also known as satellites or microsatellites.

As described above, many genetic markers suitable for use with the present invention are publicly available. Those skilled in the art can also readily prepare suitable markers. For molecular marker methods, see generally, The DNA Revolution by Andrew H. Paterson 1996 (Chapter 2) in: *Genome Mapping in Plants* (ed. Andrew H. Paterson) by Academic Press/R. G. Landis Company, Austin, Tex., 7-21, which is hereby incorporated by reference in its entirety.

Transcriptional State Measurements

This section provides some exemplary methods for measuring the abundance level of genes. One of skill in the art will appreciate that this invention is not limited to the following specific methods for measuring the abundance level of genes in each organism in a plurality of organisms.

Transcript Assay Using Microarrays

The techniques described in this section are particularly useful for the determination of the expression state or the transcriptional state of a cell sample and/or tissue sample by monitoring expression profiles. These techniques include the provision of polynucleotide probe arrays that can be used to provide simultaneous determination of the expression levels of a plurality of genes. These techniques further provide methods for designing and making such polynucleotide probe arrays.

The expression level of a nucleotide sequence in a gene can be measured by any high throughput techniques. However measured, the result is either the absolute or relative amounts of transcripts or response data, including but not limited to values representing abundances or abundance rations. Preferably, measurement of the expression profile is made by hybridization to transcript arrays, which are described in this subsection. In one embodiment, "transcript arrays" or "profiling arrays" are used. Transcript arrays can be employed for analyzing the expression profile in a cell sample and especially for measuring the expression profile of a cell sample of a particular tissue type or developmental state or exposed to a drug of interest.

In one embodiment, an expression profile is obtained by hybridizing detectably labeled polynucleotides representing the nucleotide sequences in mRNA transcripts present in a cell (e.g., fluorescently labeled cDNA synthesized from total cell mRNA) to a microarray. A microarray is an array of positionally-addressable binding (e.g., hybridization) sites on a support for representing many of the nucleotide sequences in the genome of a cell or organism, preferably most or almost all of the genes. Each of such binding sites consists of polynucleotide probes bound to the predetermined region on the support. Microarrays can be made in a number of ways, of which several are described herein below. See, for example, Draghici, 2003, *Data Analysis Tools For DNA Microarrays*, CRC Press LLC, Boca Raton, Fla., which is hereby incorporated by reference in its entirety.

However produced, microarrays share certain characteristics. The arrays are reproducible, allowing multiple copies of a given array to be produced and easily compared with each other. Preferably, the microarrays are made from materials that are stable under binding (e.g., nucleic acid hybridization) conditions. Microarrays are preferably small, e.g., between 1 $cm^2$ and 25 $cm^2$, preferably 1 to 3 $cm^2$. However, both larger and smaller arrays are also contemplated and may be preferable, e.g., for simultaneously evaluating a very large number or very small number of different probes.

Preferably, a given binding site or unique set of binding sites in the microarray will specifically bind (e.g., hybridize) to a nucleotide sequence in a single gene from a cell or organism (e.g., to exon of a specific mRNA or a specific cDNA derived therefrom).

The microarrays used can include one or more test probes, each of which has a polynucleotide sequence that is complementary to a subsequence of RNA or DNA to be detected. Each probe typically has a different nucleic acid sequence, and the position of each probe on the solid surface of the array is usually known. Indeed, the microarrays are preferably addressable arrays, more preferably positionally addressable arrays. Each probe of the array is preferably located at a known, predetermined position on the solid support so that the identity (e.g., the sequence) of each probe can be determined from its position on the array (e.g., on the support or surface). In some embodiments, the arrays are ordered arrays.

Preferably, the density of probes on a microarray or a set of microarrays is 100 different (e.g., non-identical) probes per 1 $cm^2$ or higher. More preferably, a microarray used in the methods of the invention will have at least 550 probes per 1 $cm^2$, at least 1,000 probes per 1 $cm^2$, at least 1,500 probes per 1 $cm^2$ or at least 2,000 probes per 1 $cm^2$. In a particularly preferred embodiment, the microarray is a high density array, preferably having a density of at least 2,500 different probes per 1 $cm^2$. The microarrays used in the invention therefore preferably contain at least 2,500, at least 5,000, at least 10,000, at least 15,000, at least 20,000, at least 25,000, at least 50,000 or at least 55,000 different (e.g., non-identical) probes. In one embodiment, the microarray if the Affymetrix U133+2.0 microarray (Santa Clara, Calif.).

In one embodiment, the microarray is an array (e.g., a matrix) in which each position represents a discrete binding site for a nucleotide sequence of a transcript encoded by a gene (e.g., for an exon of an mRNA or a cDNA derived therefrom). The collection of binding sites on a microarray contains sets of binding sites for a plurality of genes. For example, in various embodiments, the microarrays of the invention can comprise binding sites for products encoded by fewer than 50% of the genes in the genome of an organism. Alternatively, the microarrays of the invention can have binding sites for the products encoded by at least 50%, at least 75%, at least 85%, at least 90%, at least 95%, at least 99% or 100% of the genes in the genome of an organism. In other embodiments, the microarrays of the invention can having binding sites for products encoded by fewer than 50%, by at least 50%, by at least 75%, by at least 85%, by at least 90%, by at least 95%, by at least 99% or by 100% of the genes expressed by a cell of an organism. The binding site can be a DNA or DNA analog to which a particular RNA can specifically hybridize. The DNA or DNA analog can be, e.g. a synthetic oligomer or a gene fragment, e.g. corresponding to an exon.

In some embodiments of the present invention, a gene or an exon in a gene is represented in the profiling arrays by a set of binding sites comprising probes with different polynucleotides that are complementary to different sequence segments of the gene or the exon. Such polynucleotides are preferably of the length of 15 to 200 bases, more preferably of the length of 20 to 100 bases, most preferably 40-60 bases. Each probe sequence may also comprise linker sequences in addition to the sequence that is complementary to its target sequence. As used herein, a linker sequence is a sequence between the sequence that is complementary to its target sequence and the surface of support. For example, in preferred embodiments, the profiling arrays of the invention comprise one probe specific to each target gene or exon. However, if desired, the profiling arrays may contain at least 2, 5, 10, 100, or 1000 or more probes specific to some target genes or exons. For example, the array may contain probes tiled across the sequence of the longest mRNA isoform of a gene at single base steps.

In specific embodiments of the invention, when an exon has alternative spliced variants, a set of polynucleotide probes of successive overlapping sequences, i.e., tiled sequences, across the genomic region containing the longest variant of an exon can be included in the exon profiling arrays. The set of polynucleotide probes can comprise successive overlapping sequences at steps of a predetermined base intervals, e.g. at steps of 1, 5, or 10 base intervals, span, or are tiled across, the mRNA containing the longest variant. Such sets of probes therefore can be used to scan the genomic region containing all variants of an exon to determine the expressed variant or variants of the exon to determine the expressed variant or variants of the exon. Alternatively or additionally, a set of polynucleotide probes comprising exon specific probes and/or variant junction probes can be included in the exon profiling array. As used herein, a variant junction probe refers to a probe specific to the junction region of the particular exon variant and the neighboring exon. In some cases, the probe set contains variant junction probes specifically hybridizable to each of all different splice junction sequences of the exon. In other cases, the probe set contains exon specific probes specifically hybridizable to the common sequences in all different variants of the exon, and/or variant junction probes specifically hybridizable to the different splice junction sequences of the exon.

In some cases, an exon is represented in the exon profiling arrays by a probe comprising a polynucleotide that is complementary to the full length exon. In such instances, an exon is represented by a single binding site on the profiling arrays. In some preferred cases, an exon is represented by one or more binding sites on the profiling arrays, each of the binding sites comprising a probe with a polynucleotide sequence that is complementary to an RNA fragment that is a substantial portion of the target exon. The lengths of such probes are normally between 15-600 bases, preferably between 20-200 bases, more preferably between 30-100 bases, and most preferably between 40-80 bases. The average length of an exon is about 200 bases (see, e.g., Lewin, Genes V, Oxford University Press, Oxford, 1994). A probe of length of 40-80 allows more specific binding of the exon than a probe of shorter length, thereby increasing the specificity of the probe to the target exon. For certain genes, one or more targeted exons may have sequence lengths less than 40-80 bases. In such cases, if probes with sequences longer than the target exons are to be used, it may be desirable to design probes comprising sequences that include the entire target exon flanked by sequences from the adjacent constitutively splice exon or exons such that the probe sequences are complementary to the corresponding sequence segments in the mRNAs. Using flanking sequence from adjacent constitutively spliced exon or exons rather than the genomic flanking sequences, e.g., intron sequences, permits comparable hybridization stringency with other probes of the same length. Preferably the flanking sequence used is from the adjacent constitutively spliced exon or exons that are not involved in any alternative pathways. More preferably the flanking sequences used do not comprise a significant portion of the sequence of the adjacent exon or exons so that cross-hybridization can be minimized. In some embodiments, when a target exon that is shorter than the desired probe length is involved in alternative splicing, probes comprising flanking sequences in different alternatively spliced mRNAs are designed so that expression level of the exon expressed in different alternatively spliced mRNAs can be measured.

In some instances, when alternative splicing pathways and/or exon duplication in separate genes are to be distinguished, the DNA array or set of arrays can also comprise probes that are complementary to sequences spanning the junction regions of two adjacent exons. Preferably, such probes comprise sequences from the two exons which are not substantially overlapped with probes for each individual exons so that cross hybridization can be minimized. Probes that comprise sequences from more than one exons are useful in distinguishing alternative splicing pathways and/or expression of duplicated exons in separate genes if the exons occurs in one or more alternative spliced mRNAs and/or one or more separated genes that contain the duplicated exons but not in other alternatively spliced mRNAs and/or other genes that contain the duplicated exons. Alternatively, for duplicate exons in separate genes, if the exons from different genes show substantial difference in sequence homology, it is preferable to include probes that are different so that the exons from different genes can be distinguished.

It will be apparent to one skilled in the art that any of the probe schemes, supra, can be combined on the same profiling array and/or on different arrays within the same set of profiling arrays so that a more accurate determination of the expression profile for a plurality of genes can be accomplished. It will also be apparent to one skilled in the art that the different probe schemes can also be used for different levels of accuracies in profiling. For example, a profiling array or array set comprising a small set of probes for each exon may be used to determine the relevant genes and/or RNA splicing pathways under certain specific conditions. An array or array set comprising larger sets of probes for the exons that are of interest is then used to more accurately determine the exon expression profile under such specific conditions. Other DNA array strategies that allow more advantageous use of different probe schemes are also encompassed.

Preferably, the microarrays used in the invention have binding sites (e.g., probes, probe sets) for sets of exons for one or more genes relevant to the action of a drug of interest or in a biological pathway of interest. As discussed above, a "gene" is identified as a portion of DNA that is transcribed by RNA polymerase, which may include a 5' untranslated region ("UTR"), introns, exons and a 3' UTR. The number of genes in a genome can be estimated from the number of mRNAs expressed by the cell or organism, or by extrapolation of a well characterized portion of the genome. When the genome of the organism of interest has been sequenced, the number of ORFs can be determined and mRNA coding regions identified by analysis of the DNA sequence. For example, the genome of Saccharomyces cerevisiae has been completely sequenced and is reported to have approximately 6275 ORFs encoding sequences longer the 99 amino acid residues in length. Analysis of these ORFs indicates that there are 5,885 ORFs that are likely to encode protein products (Goffeau et al., 1996, Science 274: 546-567). In contrast, the human genome has more genes. In some embodiments of the invention, an array set comprising in total probes for all known or predicted exons in the genome of an organism is provided. As a non-limiting example, the present invention provides an array set comprising one or two probes for each known or predicted exon in the human genome.

It will be appreciated that when cDNA complementary to the RNA of a cell is made and hybridized to a microarray under suitable hybridization conditions, the level of hybridization to the site in the array corresponding to an exon of any particular gene will reflect the prevalence in the cell of mRNA or mRNAs containing the exon transcribed from that gene. For example, when detectably labeled (e.g., with a fluorophore) cDNA complementary to the total cellular mRNA is hybridized to a microarray, the site on the array corresponding to an exon of a gene (e.g., capable of specifically binding the product or products of the gene expressing) that is not transcribed or is removed during RNA splicing in the cell will have little or no signal (e.g., fluorescent signal), and an exon of a gene for which the encoded mRNA expressing the exon is prevalent will have a relatively strong signal. The relative abundance of different mRNAs produced from the same gene by alternative splicing is then determined by the signal strength pattern across the whole set of exons monitored for the gene.

In some embodiments of the invention, at least 5, 10, 20, or 100 dyes of different colors can be used for labeling. Such labeling permits simultaneous hybridizing of the distinguishably labeled cDNA populations to the same array, and thus measuring, and optionally comparing the expression levels of; mRNA molecules derived from more than two samples. Dyes that can be used include, but are not limited to, fluorescein and its derivatives, rhodamine and its derivatives, texas red, 5'carboxy-fluorescein ("FMA"), 2',7'-dimethoxy-4',5'-dichloro-6-carboxy-fluorescein ("JOE"), N,N,N',N'-tetramethyl-6-carboxy-rhodamine ("TAMRA"), 6'carboxy-X-rhodamine ("ROX"), HEX, TET, ERD40, and IRD41, cyamine dyes, including but are not limited to Cy3, Cy3.5 and Cy5; BODIPY dyes including but are not limited to BODIPY-FL, BODIPY-TR, BODIPY-TMR, BODIPY-630/650, and BODIPY-650/670; and ALEXA dyes, including but are not limited to ALEXA-488, ALEXA-532, ALEXA-546, ALEXA-568, and ALEXA-594; as well as other fluorescent dyes which will be known to those who are skilled in the art.

In some embodiments of the invention, hybridization data are measured at a plurality of different hybridization times so that the evolution of hybridization levels to equilibrium can be determined. In such embodiments, hybridization levels are most preferably measured at hybridization times spanning the range from 0 to in excess of what is required for sampling of the bound polynucleotides (e.g., the probe or probes) by the labeled polynucleotides so that the mixture is close to or substantially reached equilibrium, and duplexes are at concentrations dependent on affinity and abundance rather than diffusion. However, the hybridization times are preferably short enough that irreversible binding interactions between the labeled polynucleotide and the probes and/or the surface do not occur, or are at least limited. For example, in embodiments where polynucleotide arrays are used to probe a complex mixture of fragmented polynucleotides, typical hybridization times may be approximately 0-72 hours. Appropriate hybridization times for other embodiments will depend on the particular polynucleotide sequences and probes used, and may be determined by those skilled in the art (see, e.g., Sambrook et al., Eds., 1989, *Molecular Cloning: A Laboratory Manual*, 2nd ed., Vol. 1-3, Cold Spring Harbor Laboratory, Cold Spring Harbor, N.Y., which is hereby incorporated by reference in its entirety).

In one embodiment, hybridization levels at different hybridization times are measured separately on different, identical microarrays. For each such measurement, at hybridization time when hybridization level is measured, the microarray is washed briefly, preferably in room temperature in an aqueous solution of high to moderate salt concentration (e.g., 0.5 to 3 M salt concentration) under conditions which retain all bound or hybridized polynucleotides while removing all unbound polynucleotides. The detectable label on the remaining, hybridized polynucleotide molecules on each probe is then measured by a method which is appropriate to the particular labeling method used. The resulted hybridization levels are then combined to form a hybridization curve. In another embodiment, hybridization levels are measured in real time using a single microarray. In this embodiment, the microarray is allowed to hybridize to the sample without interruption and the microarray is interrogated at each hybridization time in a non-invasive manner. In still another embodiment, one can use one array, hybridize for a short time, wash and measure the hybridization level, put back to the same sample, hybridize for another period of time, wash and measure again to get the hybridization time curve.

Preparing Probes for Microarrays

As noted above, the "probe" to which a particular polynucleotide molecule, such as an exon, specifically hybridizes according to the invention is a complementary polynucleotide sequence. Preferably one or more probes are selected for each target exon. For example, when a minimum number of probes are to be used for the detection of an exon, the probes normally comprise nucleotide sequences greater than 40 bases in length. Alternatively, when a large set of redundant probes is to be used for an exon, the probes normally comprise nucleotide sequences of 40-60 bases. The probes can also comprise sequences complementary to full length exons. The lengths of exons can range from less than 50 bases to more than 200 bases. Therefore, when a probe length longer than exon is to be used, it is preferable to augment the exon sequence with adjacent constitutively spliced exon sequences such that the probe sequence is complementary to the continuous mRNA fragment that contains the target exon. This will allow comparable hybridization stringency among the probes of an exon profiling array. It will be understood that each probe sequence may also comprise linker sequences in addition to the sequence that is complementary to its target sequence.

The probes may comprise DNA or DNA "mimics" (e.g., derivatives and analogues) corresponding to a portion of each exon of each gene in an organism's genome. In one embodiment, the probes of the microarray are complementary RNA or RNA mimics. DNA mimics are polymers composed of subunits capable of specific, Watson-Crick-like hybridization with DNA, or of specific hybridization with RNA. The nucleic acids can be modified at the base moiety, at the sugar moiety, or at the phosphate backbone. Exemplary DNA mimics include, e.g., phosphorothioates. DNA can be obtained, e.g., by polymerase chain reaction (PCR) amplification of exon segments from genomic DNA, cDNA (e.g., by RT-PCR), or cloned sequences. PCR primers are preferably chosen based on known sequence of the exons or cDNA that result in amplification of unique fragments (e.g., fragments that do not share more than 10 bases of contiguous identical sequence with any other fragment on the microarray). Computer programs that are well known in the art are useful in the design of primers with the required specificity and optimal amplification properties, such as Oligo version 5.0 (National Biosciences). Typically each probe on the microarray will be between 20 bases and 600 bases, and usually between 30 and 200 bases in length. PCR methods are well known in the art, and are described, for example, in Innis et al., eds., 1990, *PCR Protocols: A Guide to Methods and Applications*, Academic Press Inc., San Diego, Calif., which is hereby incorporated by reference in its entirety. It will be apparent to one skilled in the art that controlled robotic systems are useful for isolating and amplifying nucleic acids.

An alternative, preferred means for generating the polynucleotide probes of the microarray is by synthesis of synthetic polynucleotides or oligonucleotides, e.g., using N-phosphonate or phosphoramidite chemistries (Froehler et al., 1986, *Nucleic Acid Res.* 14:5399-5407; McBride et al., 1983, *Tetrahedron Lett.* 24:246-248, each of which is hereby incorporated by reference in its entirety). Synthetic sequences are typically between 15 and 600 bases in length, more typically between 20 and 100 bases, most preferably between 40 and 70 bases in length. In some embodiments, synthetic nucleic acids include non-natural bases, such as, but by no means limited to, inosine. As noted above, nucleic acid analogues may be used as binding sites for hybridization. An example of a suitable nucleic acid analogue is peptide nucleic acid (see, e.g., Egholm et al., 1993, *Nature* 363:566-568; and U.S. Pat. No. 5,539,083, which is hereby incorporated by reference in its entirety).

In alternative embodiments, the hybridization sites (e.g., the probes) are made from plasmid or phage clones of genes, cDNAs (e.g., expressed sequence tags), or inserts therefrom (Nguyen et al., 1995, *Genomics* 29:207-209, which is hereby incorporated by reference in its entirety).

Attaching Nucleic Acids to the Solid Surface

Preformed polynucleotide probes can be deposited on a support to form the array. Alternatively, polynucleotide probes can be synthesized directly on the support to form the array. The probes are attached to a solid support or surface, which may be made, e.g., from glass, plastic (e.g., polypropylene, nylon), polyacrylamide, nitrocellulose, gel, or other porous or nonporous material.

A preferred method for attaching the nucleic acids to a surface is by printing on glass plates, as is described generally by Schena et al, 1995, *Science* 270:467-470. This method is especially useful for preparing microarrays of cDNA (See also, DeRisi et al, 1996, *Nature Genetics* 14:457-460; Shalon et al., 1996, *Genome Res.* 6:639-645; and Schena et al., 1995, *Proc. Natl. Acad. Sci. U.S.A.* 93:10539-11286).

A second preferred method for making microarrays is by making high-density polynucleotide arrays. Techniques are known for producing arrays containing thousands of oligonucleotides complementary to defined sequences, at defined locations on a surface using photolithographic techniques for synthesis in situ (see, Fodor et al., 1991, *Science* 251:767-773; Pease et al., 1994, *Proc. Natl. Acad. Sci. U.S.A.* 91:5022-5026; Lockhart et al., 1996, *Nature Biotechnology* 14:1675; U.S. Pat. Nos. 5,578,832; 5,556,752; and 5,510,270) or other methods for rapid synthesis and deposition of defined oligonucleotides (Blanchard et al., *Biosensors & Bioelectronics* 11:687-690). When these methods are used, oligonucleotides (e.g., 60-mers) of known sequence are synthesized directly on a surface such as a derivatized glass slide. The array produced can be redundant, with several polynucleotide molecules per exon.

Other methods for making microarrays, e.g. by masking (Maskos and Southern, 1992, *Nucl. Acids. Res.* 20:1679-1684), may also be used. In principle, and as noted supra, any type of array, for example, dot blots on a nylon hybridization membrane (see Sambrook et al., supra) could be used. However, as will be recognized by those skilled in the art, very small arrays will frequently be preferred because hybridization volumes will be smaller.

In a particularly preferred embodiment, microarrays of the invention are manufactured by means of an ink jet printing device for oligonucleotide synthesis, e.g., using the methods and systems described by Blanchard in International Patent Publication No. WO 98/41531, published Sep. 24, 1998; Blanchard et al., 1996, *Biosensors and Bioelectronics* 11:687-690; Blanchard, 1998, in *Synthetic DNA Arrays in Genetic Engineering*, Vol. 20, J. K. Setlow, Ed., Plenum Press, New York at pages 111-123; and U.S. Pat. No. 6,028,189 to Blanchard. Specifically, the polynucleotide probes in such microarrays are preferably synthesized in arrays, e.g., on a glass slide, by serially depositing individual nucleotide bases in "microdroplets" of a high surface tension solvent such as propylene carbonate. The microdroplets have small volumes (e.g. 100 pL or less, more preferably 50 pL or less) and are separated from each other on the microarray (e.g., by hydrophobic domains) to form circular surface tension wells which define the locations of the array elements (i.e., the different probes). Polynucleotide probes are normally attached to the surface covalently at the 3' end of the polynucleotide. Alternatively, polynucleotide probes can be attached to the surface covalently at the 5' end of the polynucleotide (see for example, Blanchard, 1998, in *Synthetic DNA Arrays in Genetic Engineering*, Vol. 20, J. K. Setlow, Ed., Plenum Press, New York at pages 111-123).

Target Polynucleotide Molecules

Target polynucleotides that can be analyzed by the methods and compositions of the invention include RNA molecules such as, but by no means limited to, messenger RNA (mRNA) molecules, ribosomal RNA (rRNA) molecules, cRNA molecules (e.g., RNA molecules prepared from cDNA molecules that are transcribed in vivo), cDNA, and fragments thereof. Target polynucleotides that may also be analyzed by the methods and compositions of the present invention include, but are not limited to DNA molecules such as genomic DNA molecules, cDNA molecules, and fragments thereof including oligonucleotides, ESTs, STSs, etc.

The target polynucleotides can be from any source. For example, the target polynucleotide molecules may be naturally occurring nucleic acid molecules such as genomic or extragenomic DNA molecules isolated from an organism, or RNA molecules, such as mRNA molecules, isolated from an organism. Alternatively, the polynucleotide molecules may be synthesized, including, e.g. nucleic acid molecules synthesized enzymatically in vivo or in vitro, such as cDNA molecules, or polynucleotide molecules synthesized by PCR, RNA molecules synthesized by in vitro transcription, etc. The sample of target polynucleotides can comprise, e.g. molecules of DNA, RNA, or copolymers of DNA and RNA. In preferred embodiments, the target polynucleotides of the invention will correspond to particular genes or to particular gene transcripts (e.g., to particular mRNA sequences expressed in cells or to particular cDNA sequences derived from such mRNA sequences). However, in many embodiments, particularly those embodiments wherein the polynucleotide molecules are derived from mammalian cells, the target polynucleotides may correspond to particular fragments of a gene transcript. For example, the target polynucleotides may correspond to different exons of the same gene, e.g., so that different splice variants of that gene may be detected and/or analyzed.

In preferred embodiments, the target polynucleotides to be analyzed are prepared in vitro from nucleic acids extracted from cells. For example, in one embodiment, RNA is extracted from cells (e.g., total cellular RNA, poly(A)$^+$ messenger RNA, fraction thereof) and messenger RNA is purified from the total extracted RNA. Methods for preparing total and poly(A)$^+$ RNA are well known in the art, and are described generally, e.g., in Sambrook et al., supra. In one embodiment, RNA is extracted from cells of the various types of interest in this invention using guanidinium thiocyanate lysis followed by CsCl centrifugation and an oligo dT purification (Chirgwin et al., 1979, *Biochemistry* 18:5294-5299). In another embodiment, RNA is extracted from cells using guanidinium thiocyanate lysis followed by purification on RNeasy columns (Qiagen). cDNA is then synthesized from the purified mRNA using, e.g., oligo-dT or random primers. In preferred embodiments, the target polynucleotides are cRNA prepared from purified messenger RNA extracted from cells. As used herein, cRNA is defined here as RNA complementary to the source RNA. The extracted RNAs are amplified using a process in which doubled-stranded cDNAs are synthesized from the RNAs using a primer linked to an RNA polymerase promoter in a direction capable of directing transcription of anti-sense RNA. Anti-sense RNAs or cRNAs are then transcribed from the second strand of the double-stranded cDNAs using an RNA polymerase (see, e.g. U.S. Pat. Nos. 5,891,636; 5,716,785; 5,545,522; 6,132,997; and 6,271,002, each of which is hereby incorporated by reference in its entirety). Both oligo-dT primers (U.S. Pat. Nos. 5,545,522 and 6,132,997) or random primers that contain an RNA polymerase promoter or complement thereof can be used. Preferably, the target polynucleotides are short and/or fragmented polynucleotide molecules which are representative of the original nucleic acid population of the cell.

The target polynucleotides to be analyzed by the methods and compositions of the invention are often detectably labeled. For example, cDNA can be labeled directly, e.g., with nucleotide analogs, or indirectly, e.g., by making a second, labeled cDNA strand using the first strand as a template. Alternatively, the double-stranded cDNA can be transcribed into cRNA and labeled.

In some embodiments, the detectable label is a fluorescent label, e.g., by incorporation of nucleotide analogs. Other labels suitable for use in the present invention include, but are not limited to, biotin, imminobiotin, antigens, cofactors, dinitrophenol, lipoic acid, olefinic compounds, detectable polypeptides, electron rich molecules, enzymes capable of generating a detectable signal by action upon a substrate, and radioactive isotopes. Exemplary radioactive isotopes include, but are not limited to, $^{32}$P, $^{35}$S, $^{14}$G, $^{15}$N and $^{125}$I. Fluorescent molecules suitable for the present invention include, but are not limited to, fluorescein and its derivatives, rhodamine and its derivatives, texas red, 5'carboxy-fluorescein ("FMA"), 2',7'-dimethoxy-4',5'-dichloro-6-carboxy-fluorescein ("JOE"), N,N,N',N'-tetramethyl-6-carboxy-rhodamine ("TAMRA"), 6'carboxy-X-rhodamine ("ROX"), HEX, TET, IRD40, and IRD41. Fluorescent molecules that are suitable for the invention further include: cyamine dyes, including by not limited to Cy3, Cy3.5 and Cy5; BODIPY dyes including but not limited to BODIPY-FL, BODIPY-TR, BODIPY-TMR, BODIPY-630/650, and BODIPY-650/670; and ALEXA dyes, including but not limited to ALEXA-488, ALEXA-532, ALEXA-546, ALEXA-568, and ALEXA-594; as well as other fluorescent dyes which will be known to those who are skilled in the art. Electron rich indicator molecules suitable for the present invention include, but are not limited to, ferritin, hemocyanin, and colloidal gold. Alternatively, in some embodiments the target polynucleotides is labeled by specifically complexing a first group to the polynucleotide. A second group, covalently linked to an indicator molecules and which has an affinity for the first group, can be used to indirectly detect the target polynucleotide. In such an embodiment, compounds suitable for use as a first group include, but are not limited to, biotin and iminobiotin. Compounds suitable for use as a second group include, but are not limited to, avidin and streptavidin.

Hybridization to Microarrays

As described supra, nucleic acid hybridization and wash conditions are chosen so that the polynucleotide molecules to be analyzed by the invention (referred to herein as the "target polynucleotide molecules") specifically bind or specifically hybridize to the complementary polynucleotide sequences of the array, preferably to a specific array site, wherein its complementary DNA is located.

Arrays containing double-stranded probe DNA situated thereon are preferably subjected to denaturing conditions to render the DNA single-stranded prior to contacting with the target polynucleotide molecules. Arrays containing single-stranded probe DNA (e.g., synthetic oligodeoxyribonucleic acids) may need to be denatured prior to contacting with the target polynucleotide molecules, e.g., to remove hairpins or dimers which form due to self complementary sequences.

Optimal hybridization conditions will depend on the length (e.g., oligomer versus polynucleotide greater than 200 bases) and type (e.g., RNA, or DNA) of probe and target nucleic acids. General parameters for specific (i.e., stringent) hybridization conditions for nucleic acids are described in Sambrook et al., (supra), and in Ausubel et al., 1987, *Current Protocols in Molecular Biology*, Greene Publishing and Wiley-Interscience, New York, which is hereby incorporated by reference in its entirety. When the cDNA microarrays of Schena et al. are used, typical hybridization conditions are hybridization in 5×SSC plus 0.2% SDS at 65° C. for four hours, followed by washes at 25° C. in low stringency wash buffer (1×SSC plus 0.2% SDS), followed by 10 minutes at 25° C. in higher stringency wash buffer (0.1×SSC plus 0.2% SDS) (Schena et al., 1996, *Proc. Nal. Acad. Sci. U.S.A.* 93:10614). Useful hybridization conditions are also provided in, e.g., Tijessen, 1993, *Hybridization With Nucleic Acid Probes*, Elsevier Science Publishers; and Kricka, 1992, Nonisotopic DNA Probe Techniques, Academic Press, San Diego, Calif., each of which is hereby incorporated by reference in its entirety.

Particularly preferred hybridization conditions for use with the screening and/or signaling chips of the present invention include hybridization at a temperature at or near the mean melting temperature of the probes (e.g., within 5° C., more preferably within 2° C.) in 1 M NaCl, 50 mM MES buffer (pH 6.5), 0.5% sodium Sarcosine and 30% formamide.

Signal Detection and Data Analysis

It will be appreciated that when target sequences, e.g., cDNA or cRNA, complementary to the RNA of a cell sample and/or tissue sample is made and hybridized to a microarray under suitable hybridization conditions, the level of hybridization to the site in the array corresponding to an exon of any particular gene will reflect the prevalence in the cell of mRNA or mRNAs containing the exon transcribed from that gene. For example, when detectably labeled (e.g., with a fluorophore) cDNA complementary to the total cellular mRNA is hybridized to a microarray, the site on the array corresponding to an exon of a gene (e.g., capable of specifically binding the product or products of the gene expressing) that is not transcribed or is removed during RNA splicing in the cell will have little or no signal (e.g., fluorescent signal), and an exon of a gene for which the encoded mRNA expressing the exon is prevalent will have a relatively strong signal. The relative abundance of different mRNAs produced from the same gene by alternative splicing is then determined by the signal strength pattern across the whole set of exons monitored for the gene.

Signals are recorded and, in a preferred embodiment, analyzed by computer. In one embodiment, the scanned image is despeckled using a graphics program (e.g. Hijaak Graphics Suite) and then analyzed using an image gridding program that creates a spreadsheet of the average hybridization at each wavelength at each site. If necessary, an experimentally determined correction for "cross talk" (or overlap) between the channels for the two fluors may be made. For any particular hybridization site on the transcript array, a ratio of the emission of the two fluorophores can be calculated. The ratio is independent of the absolute expression level of the cognate gene, but is useful for genes whose expression is significantly modulated by drug administration, gene deletion, or any other tested event.

Transcript Assay Using RT-PCR

In certain embodiments, to determine the abundance of genes, the level of expression of one or more of the genes of interest is measured by amplifying RNA from a sample using reverse transcription (RT) in combination with the polymerase chain reaction (PCR). In accordance with such embodiments, the reverse transcription may be quantitative or semi-quantitative. The RT-PCR methods taught herein may be used in conjunction with the microarray methods described above. For example, a bulk PCR reaction may performed, the PCR products may be resolved and used as probe spots on a microarray.

Total RNA, or mRNA from a sample is used as a template and a primer specific to the transcribed portion of the gene(s) is used to initiate reverse transcription. Primer design can be accomplished based on known nucleotide sequences that have been published or available from any publicly available sequence database such as GenBank. For example, primers may be designed for the genes of interest. Further, primer design may be accomplished by utilizing commercially available software (e.g., Primer Designer 1.0, Scientific Software etc.). The product of the reverse transcription is subsequently used as a template for PCR.

PCR provides a method for rapidly amplifying a particular nucleic acid sequence by using multiple cycles of DNA replication catalyzed by a thermostable, DNA-dependent DNA polymerase to amplify the target sequence of interest. PCR requires the presence of a nucleic acid to be amplified, two single-stranded oligonucleotide primers flanking the sequence to be amplified, a DNA polymerase, deoxyribonucleoside triphosphates, a buffer and salts. The method of PCR is well known in the art. PCR, is performed as described in Mullis and Faloona, 1987, Methods Enzymol. 155:335, which is incorporated herein by reference.

PCR can be performed using template DNA or cDNA (at least 1 fg; more usefully, 1-1000 ng) and at least 25 pmol of oligonucleotide primers. A typical reaction mixture includes: 2 µl of DNA, 25 pmol of oligonucleotide primer, 2.5 µl of 10 M PCR buffer 1 (Perkin-Elmer, Foster City, Calif.), 0.4 µl of 1.25 M dNTP, 0.15 µl (or 2.5 units) of Taq DNA polymerase (Perkin Elmer, Foster City, Calif.) and deionized water to a total volume of 25 µl. Mineral oil is overlaid and the PCR is performed using a programmable thermal cycler.

The length and temperature of each step of a PCR cycle, as well as the number of cycles, are adjusted according to the stringency requirements in effect. Annealing temperature and timing are determined both by the efficiency with which a primer is expected to anneal to a template and the degree of mismatch that is to be tolerated. The ability to optimine the stringency of primer annealing conditions is well within the knowledge of one of moderate skill in the art. An annealing temperature of between 30° C. and 72° C. is used. Initial denaturation of the template molecules normally occurs at between 92° C. and 99° C. for 4 minutes, followed by 2040 cycles consisting of denaturation (94-99° C. for 15 seconds to 1 minute), annealing (temperature determined as discussed above; 1-2 minutes), and extension (72° C. for 1 minute). The final extension step is generally carried out for 4 minutes at 72° C., and may be followed by an indefinite (0-24 hour) step at 4° C.

Quantitative RT-PCR ("QRT-PCR"), which is quantitative in nature, can also be performed to provide a quantitative measure of gene expression levels. In QRT-PCR reverse transcription and PCR can be performed in two steps, or reverse transcription combined with PCR can be performed concurrently. One of these techniques, for which there are commercially available kits such as Taqman (Perkin Elmer, Foster City, Calif.) or as provided by Applied Biosystems (Foster City, Calif.) is performed with a transcript-specific antisense probe. This probe is specific for the PCR product (e.g. a nucleic acid fragment derived from a gene) and is prepared with a quencher and fluorescent reporter probe complexed to the 5' end of the oligonucleotide. Different fluorescent markers are attached to different reporters, allowing for measurement of two products in one reaction. When Taq DNA polymerase is activated, it cleaves off the fluorescent reporters of the probe bound to the template by virtue of its 5'-to-3' exonuclease activity. In the absence of the quenchers, the reporters now fluoresce. The color change in the reporters is proportional to the amount of each specific product and is measured by a fluorometer; therefore, the amount of each color is measured and the PCR product is quantified. The PCR reactions are performed in 96-well plates so that samples derived from many individuals are processed and measured simultaneously. The Taqman system has the additional advantage of not requiring gel electrophoresis and allows for quantification when used with a standard curve.

A second technique useful for detecting PCR products quantitatively without is to use an intercalating dye such as the commercially available QuantiTect SYBR Green PCR (Qiagen, Valencia Calif.). RT-PCR is performed using SYBR green as a fluorescent label which is incorporated into the PCR product during the PCR stage and produces a flourescense proportional to the amount of PCR product.

Both Taqman and QuantiTect SYBR systems can be used subsequent to reverse transcription of RNA. Reverse transcription can either be performed in the same reaction mixture as the PCR step (one-step protocol) or reverse transcription can be performed first prior to amplification utilizing PCR (two-step protocol).

Additionally, other systems to quantitatively measure mRNA expression products are known including Molecular Beacons® which uses a probe having a fluorescent molecule and a quencher molecule, the probe capable of forming a hairpin structure such that when in the hairpin form, the fluorescence molecule is quenched, and when hybridized the fluorescence increases giving a quantitative measurement of gene expression.

Additional techniques to quantitatively measure RNA expression include, but are not limited to, polymerase chain reaction, ligase chain reaction, Qbeta replicase (see, e.g., International Application No. PCT/US87/00880, which is hereby incorporated by reference in its entirety), isothermal amplification method (see, e.g. Walker et al., 1992, PNAS 89:382-396, herein incorporated by reference), strand displacement amplification (SDA), repair chain reaction, Asymmetric Quantitative PCR (see, e.g., U.S. Publication No. US 2003/30134307A1, herein incorporated by reference) and the multiplex microsphere bead assay described in Fuja et al., 2004, Journal of Biotechnology 108:193-205, herein incorporated by reference in its entirety.

The level of expression of one or more of the genes of interest can, for example, be measured by amplifying RNA from a sample using amplification (NASBA). See, e.g., Kwoh et al., 1989, PNAS USA 86:1173; International Publication No. WO 88/10315; and U.S. Pat. No. 6,329,179, each of which is hereby incorporated by reference in its entirety. In NASBA, the nucleic acids may be prepared for amplification using conventional methods, e.g., phenol/chloroform extraction, heat denaturation, treatment with lysis buffer and minispin columns for isolation of DNA and RNA or guanidinium chloride extraction of RNA. These amplification techniques involve annealing a primer that has target specific sequences. Following polymerization, DNA/RNA hybrids are digested with RNase H while double stranded DNA molecules are heat denatured again. In either case the single stranded DNA is made fully double stranded by addition of second target specific primer, followed by polymerization. The double-stranded DNA molecules are then multiply transcribed by a polymerase such as T7 or SP6. In an isothermal cyclic reaction, the RNA's are reverse transcribed into double stranded DNA, and transcribed once with a polymerase such as T7 or SP6. The resulting products, whether truncated or complete, indicate target specific sequences.

Several techniques can be used to separate amplification products. For example, amplification products may be separated by agarose, agarose-acrylamide or polyacrylamide gel electrophoresis using conventional methods. See Sambrook et al., 2001. Several techniques for detecting PCR products quantitatively without electrophoresis may also be used according to the invention (see, e.g., *PCR Protocols, A Guide* to *Methods and Applications*, Innis et al. 1990, Academic Press, Inc. N.Y., which is hereby incorporated by reference. For example, chromatographic techniques may be employed to effect separation. There are many kinds of chromatography which may be used in the present invention: adsorption, partition, ion-exchange and molecular sieve, HPLC, and many specialized techniques for using them including column, paper, thin-layer and gas chromatography (Freifelder, *Physical Biochemistry Applications to Biochemistry and Molecular Biology*, 2nd ed., Wm. Freeman and Co., New York, N.Y., 1982, which is hereby incorporated by reference).

Another example of a separation methodology is done by covalently labeling the oligonucleotide primers used in a PCR reaction with various types of small molecule ligands. In one such separation, a different ligand is present on each oligonucleotide. A molecule, perhaps an antibody or avidin if the ligand is biotin, that specifically binds to one of the ligands is used to coat the surface of a plate such as a 96 well ELISA plate. Upon application of the PCR reactions to the surface of such a prepared plate, the PCR products are bound with specificity to the surface. After washing the plate to remove unbound reagents, a solution containing a second molecule that binds to the first ligand is added. This second molecule is linked to some kind of reporter system. The second molecule only binds to the plate if a PCR product has been produced whereby both oligonucleotide primers are incorporated into the final PCR products. The amount of the PCR product is then detected and quantified in a commercial plate reader much as ELISA reactions are detected and quantified. An ELISA-like system such as the one described here has been developed by the Raggio Italgene company under the C-Track trade name.

Amplification products are typically visualized in order to confirm amplification of the nucleic acid sequences of interest, e.g., nucleic acid sequences of one or more of the genes of interest. One typical visualization method involves staining of a gel with ethidium bromide and visualization under UV light. Alternatively, if the amplification products are integrally labeled with radio- or fluorometrically-labeled nucleotides, the amplification products may then be exposed to x-ray film or visualized under the appropriate stimulating spectra, following separation.

In one embodiment, visualization is achieved indirectly. Following separation of amplification products, a labeled, nucleic acid probe is brought into contact with the amplified nucleic acid sequence of interest. The probe preferably is conjugated to a chromophore but may be radiolabeled. In another embodiment, the probe is conjugated to a binding partner, such as an antibody or biotin, where the other member of the binding pair carries a detectable moiety.

In another embodiment, detection is by Southern blotting and hybridization with a labeled probe. The techniques involved in Southern blotting are well known to those of skill in the art and may be found in many standard books on molecular protocols. Briefly, amplification products are separated by gel electrophoresis. The gel is then contacted with a membrane, such as nitrocellulose, permitting transfer of the nucleic acid and non-covalent binding. Subsequently, the membrane is incubated with a chromophore-conjugated probe that is capable of hybridizing with a target amplification product. Detection is by exposure of the membrane to x-ray film or ion-emitting detection devices. One example of the foregoing is described in U.S. Pat. No. 5,279,721, incorporated by reference herein, which discloses an apparatus and method for the automated electrophoresis and transfer of nucleic acids. The apparatus permits electrophoresis and blotting without external manipulation of the gel and is ideally suited to carrying out methods according to the present invention.

Nuclease Protection Assays

In particular embodiments, gene abundance can be obtained by performing nuclease protection assays (including both ribonuclease protection assays and S1 nuclease assays) to detect and quantitate specific mRNAs. Such assays are described in, for example, Sambrook et al., 2001, supra. In nuclease protection assays, an antisense probe (labeled with, e.g., radiolabeled or nonisotopic) hybridizes in solution to an RNA sample. Following hybridization, single-stranded, unhybridized probe and RNA are degraded by nucleases. An acrylamide gel is used to separate the remaining protected fragments. Typically, solution hybridization is more efficient than membrane-based hybridization, and it can accommodate up to 100 μg of sample RNA, compared with the 20-30 μg maximum of blot hybridizations.

The ribonuclease protection assay, which is a common type of nuclease protection assay, requires the use of RNA probes. Oligonucleotides and other single-stranded DNA probes can only be used in assays containing S1 nuclease. The single-stranded, antisense probe must typically be completely homologous to target RNA to prevent cleavage of the probe: target hybrid by nuclease.

Northern Blot Assays

Any hybridization technique known to those of skill in the art can be used to generate abundance values for genes of interest. In some embodiments, abundance values are obtained by Northern blot analysis (to detect and quantify specific RNA molecules. A standard Northern blot assay can be used to ascertain an RNA transcript size, identify alternatively spliced RNA transcripts, and the relative amounts of one or more genes of interest (in particular, mRNA) in a sample, in accordance with conventional Northern hybridization techniques known to those persons of ordinary skill in the art. In Northern blots, RNA samples are first separated by size via electrophoresis in an agarose gel under denaturing conditions. The RNA is then transferred to a membrane, crosslinked and hybridized with a labeled probe. Nonisotopic or high specific activity radiolabeled probes can be used including random-primed, nick-translated, or PCR-generated DNA probes, in vitro transcribed RNA probes, and oligonucleotides. Additionally, sequences with only partial homology (e.g., cDNA from a different species or genomic DNA fragments that might contain an exon) may be used as probes. The labeled probe, e.g. a radiolabelled cDNA, either containing the full-length, single stranded DNA or a fragment of that DNA sequence may be at least 20, at least 30, at least 50, or at least 100 consecutive nucleotides in length. The probe can be labeled by any of the many different methods known to those skilled in this art. The labels most commonly employed for these studies are radioactive elements, enzymes, chemicals that fluoresce when exposed to ultraviolet light, and others. A number of fluorescent materials are known and can be utilized as labels. These include, but are not limited to, fluorescein, rhodamine, auramine, Texas Red, AMCA blue and Lucifer Yellow. The radioactive label can be detected by any of the currently available counting procedures. Non-limiting examples of isotopes include 3H, 14C, 32P, 35S, 36Cl, 51Cr, 57Co, 58Co, 59Fe, 90Y, 125I, 131I, and 186Re. Enzyme labels are likewise useful, and can be detected by any of the presently utilized colorimetric, spectrophotometric, fluorospectrophotometric, amperometric or gasometric techniques. The enzyme is conjugated to the selected particle by reaction with bridging molecules such as carbodiimides, diisocyanates, glutaraldehyde and the like. Any enzymes known to one of skill in the art can be utilized. Examples of such enzymes include, but are not limited to, peroxidase, beta-D-galactosidase, urease, glucose oxidase plus peroxidase and alkaline phosphatase. U.S. Pat. Nos. 3,654,090, 3,850,752, and 4,016,043, hereby incorporated by reference, are referred to by way of example for their disclosure of alternate labeling material and methods.

Other Methods of Transcriptional State Measurement

The transcriptional state of a cell can be measured by other gene expression technologies known in the art Several such technologies produce pools of restriction fragments of limited complexity for electrophoretic analysis, such as methods combining double restriction enzyme digestion with phasing primers (see, e.g., European Patent O 534858 A1, filed Sep. 24, 1992, by Zabeau et al., each of which is hereby incorporated by reference in its entirety), or methods selecting restriction fragments with sites closest to a defined mRNA end (see, e.g., Prashar et al., 1996, Proc. Natl. Acad. Sci. USA 93:659-663, which is hereby incorporated by reference in its entirety). Other methods statistically sample cDNA pools, such as by sequencing sufficient bases (e.g., 20-50 bases) in each of multiple cDNAs to identify each cDNA, or by sequencing short tags (e.g., 9-10 bases) that are generated at known positions relative to a defined mRNA end (see, e.g., Velculescu, 1995, Science 270, 484-487, which is hereby incorporated by reference in its entirety).

Other Types of Measurements of Gene Abundance

In various embodiments of the present invention, aspects of the biological state other than the transcriptional state, such as the translational state, the activity state, or mixed aspects can be measured. Thus, in such embodiments, gene expression data can include translational state measurements or even protein expression measurements. Details of embodiments in which aspects of the biological state other than the transcriptional state are described in this section.

Translational State Measurements

In specific embodiments of the invention, gene abundance can be obtained by detecting proteins, for example, by detecting the expression product (e.g. a nucleic acid or protein) of one or more genes of interest, or post-translationally modified, or otherwise modified, or processed forms of such proteins. Measurement techniques include, but are not limited to protein microarray analysis, immunohistochemistry and mass spectrometry. In one example, whole genome monitoring of protein (e.g., the "proteome,") can be carried out by constructing a microarray in which binding sites comprise immobilized, preferably monoclonal, antibodies specific to a plurality of protein species encoded by the cell genome. Preferably, antibodies are present for a substantial fraction of the encoded proteins, or at least for those proteins relevant to the action of a drug of interest. Methods for making monoclonal antibodies are well known (see, e.g., Harlow and Lane, 1988, *Antibodies: A Laboratory Manual*, Cold Spring Harbor, N.Y., which is incorporated in its entirety for all purposes). In one embodiment, monoclonal antibodies are raised against synthetic peptide fragments designed based on genomic sequence of the cell. With such an antibody array, proteins from the cell are contacted to the array and their binding is assayed with assays known in the art.

Alternatively, proteins can be separated by two-dimensional gel electrophoresis systems. Two-dimensional gel electrophoresis is well-known in the art and typically involves iso-electric focusing along a first dimension followed by SDS-PAGE electrophoresis along a second dimension. See, e.g., Hames et al., 1990, *Gel Electrophoresis of Proteins: A Practical Approach*, IRL Press, New York; Shevchenko et al., 1996, *Proc. Natl. Acad. Sci. USA* 93:1440-1445; Sagliocco et al., 1996, Yeast 12:1519-1533; Lander, 1996, *Science* 274: 536-539. The resulting electropherograms can be analyzed by numerous techniques, including mass spectrometric techniques, Western blotting and immunoblot analysis using polyclonal and monoclonal antibodies, and internal and N-terminal micro-sequencing. Using these techniques, it is possible to identify a substantial fraction of all the proteins produced under given physiological conditions, including in cells (e.g., in yeast) exposed to a drug, or in cells modified by, e.g., deletion or over-expression of a specific gene.

Standard techniques may be utilized for determining the amount of the protein or proteins of interest present in a sample. For example, standard techniques can be employed using, e.g., immunoassays such as, for example Western blot, immunoprecipitation followed by sodium dodecyl sulfate polyacrylamide gel electrophoresis, (SDS-PAGE), immunocytochemistry, and the like to determine the amount of protein or proteins of interest present in a sample. One exemplary agent for detecting a protein of interest is an antibody capable of specifically binding to a protein of interest, preferably an antibody detectably labeled, either directly or indirectly.

For such detection methods, if desired a protein from the sample to be analyzed can easily be isolated using techniques which are well known to those of skill in the art. Protein isolation methods can, for example, be such as those described in Harlow and Lane, 1988, Antibodies: A Laboratory Manual. Cold Spring Harbor Laboratory Press (Cold Spring Harbor, N.Y.), which is incorporated by reference herein in its entirety.

In certain embodiments, methods of detection of the protein or proteins of interest involve their detection via interaction with a protein-specific antibody. For example, antibodies directed to a protein of interest. Antibodies can be generated utilizing standard techniques well known to those of skill in the art. In specific embodiments, antibodies can be polyclonal, or more preferably, monoclonal. An intact antibody, or an antibody fragment (e.g., scFv, Fab or F(ab')$_2$) can, for example, be used.

For example, antibodies, or fragments of antibodies, specific for a protein of interest can be used to quantitatively or qualitatively detect the presence of a protein. This can be accomplished, for example, by immunofluorescence techniques. Antibodies (or fragments thereof) can, additionally, be employed histologically, as in immunofluorescence or immunoelectron microscopy, for in situ detection of a protein of interest. In situ detection can be accomplished by removing a biological sample (e.g. a biopsy specimen) from a patient, and applying thereto a labeled antibody that is directed to a protein of interest (e.g., a protein expressed from a gene in Table 30). The antibody (or fragment) is preferably applied by overlaying the antibody (or fragment) onto a biological sample. Through the use of such a procedure, it is possible to determine not only the presence of the protein of interest, but also its distribution, in a particular sample. A wide variety of well-known histological methods (such as staining procedures) can be utilized to achieve such in situ detection.

Immunoassays for a protein of interest typically comprise incubating a biological sample of a detectably labeled antibody capable of identifying a protein of interest, and detecting the bound antibody by any of a number of techniques well-known in the art. As discussed in more detail, below, the term "labeled" can refer to direct labeling of the antibody via, e.g., coupling (i.e., physically linking) a detectable substance to the antibody, and can also refer to indirect labeling of the antibody by reactivity with another reagent that is directly labeled. Examples of indirect labeling include detection of a primary antibody using a fluorescently labeled secondary antibody.

The biological sample can be brought in contact with and immobilized onto a solid phase support or carrier such as nitrocellulose, or other solid support which is capable of immobilizing cells, cell particles or soluble proteins. The support can then be washed with suitable buffers followed by treatment with the detectably labeled fingerprint gene-specific antibody. The solid phase support can then be washed with the buffer a second time to remove unbound antibody. The amount of bound label on solid support can then be detected by conventional methods.

By "solid phase support or carrier" is intended any support capable of binding an antigen or an antibody. Well-known supports or carriers include glass, polystyrene, polypropylene, polyethylene, dextran, nylon, amylases, natural and modified celluloses, polyacrylamides and magnetite. The nature of the carrier can be either soluble to some extent or insoluble for the purposes of the present invention. The support material can have virtually any possible structural configuration so long as the coupled molecule is capable of binding to an antigen or antibody. Thus, the support configuration can be spherical, as in a bead, or cylindrical, as in the inside surface of a test tube, or the external surface of a rod. Alternatively, the surface can be flat such as a sheet, test strip, etc. Preferred supports include polystyrene beads. Those skilled in the art will know many other suitable carriers for binding antibody or antigen, or will be able to ascertain the same by use of routine experimentation.

One of the ways in which an antibody specific for a protein of interest can be detectably labeled is by linking the same to an enzyme and use in an enzyme immunoassay (EIA) (Voller, 1978, "The Enzyme Linked Immunosorbent Assay (ELISA)", Diagnostic Horizons 2: 1-7, Microbiological Associates Quarterly Publication, Walkersville, M D; Voller et al., 1978, J. Clin. Pathol. 31:507-520; Butler, J. E., 1981, Meth. Enzymol. 73:482-523; Maggio, E. (ed.), 1980, Enzyme Immunoassay, CRC Press, Boca Raton, Fla.; Ishikawa, E. et al., (eds.), 1981, Enzyme Immunoassay, Kgaku Shoin, Tokyo, each of which is hereby incorporated by reference in its entirety). The enzyme which is bound to the antibody will react with an appropriate substrate, preferably a chromogenic substrate, in such a manner as to produce a chemical moiety which can be detected, for example, by spectrophotometric, fluorimetric or by visual means. Enzymes which can be used to detectably label the antibody include, but are not limited to, malate dehydrogenase, staphylococcal nuclease, delta-5-steroid isomerase, yeast alcohol dehydrogenase, alpha-glycerophosphate, dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase. The detection can be accomplished by colorimetric methods which employ a chromogenic substrate for the enzyme. Detection can also be accomplished by visual comparison of the extent of enzymatic reaction of a substrate in comparison with similarly prepared standards.

Detection can also be accomplished using any of a variety of other immunoassays. For example, by radioactively labeling the antibodies or antibody fragments, it is possible to detect a protein of interest through the use of a radioimmunoassay (RIA) (see, for example, Weintraub, B., Principles of Radioimmunoassays, Seventh Training Course on Radioligand Assay Techniques, The Endocrine Society, March, 1986, which is incorporated by reference herein). The radioactive isotope (e.g., $^{125}$I, $^{131}$I, $^{35}$S or $^{3}$H) can be detected by such means as the use of a gamma counter or a scintillation counter or by autoradiography.

It is also possible to label the antibody with a fluorescent compound. When the fluorescently labeled antibody is exposed to light of the proper wavelength, its presence can then be detected due to fluorescence. Among the most commonly used fluorescent labeling compounds are fluorescein isothiocyanate, rhodamine, phycoerythrin, phycocyanin, allophycocyanin, o-phthaldehyde and fluorescamine.

The antibody can also be detectably labeled using fluorescence emitting metals such as $^{152}$Eu, or others of the lanthanide series. These metals can be attached to the antibody using such metal chelating groups as diethylenetriaminepentacetic acid (DTPA) or ethylenediaminetetraacetic acid (EDTA).

The antibody also can be detectably labeled by coupling it to a chemiluminescent compound. The presence of the chemiluminescent-tagged antibody is then determined by detecting the presence of luminescence that arises during the course of a chemical reaction. Examples of particularly useful chemilurninescent labeling compounds are luminol, isoluminol, theromatic acridinium ester, imidazole, acridinium salt and oxalate ester.

Likewise, a bioluminescent compound can be used to label the antibody of the present invention. Bioluminescence is a type of chemiluminescence found in biological systems in, which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

In another embodiment, specific binding molecules other than antibodies, such as aptamers, may be used to bind the biomarkers. In yet another embodiment, the biomarker profile may comprise a measurable aspect of an infectious agent (e.g., lipopolysaccharides or viral proteins) or a component thereof.

In some embodiments, a protein chip assay (e.g., The ProteinChip® Biomarker System, Ciphergen, Fremont, Calif.) is used to measure feature values for the biomarkers in the biomarker profile. See also, for example, Lin, 2004, Modern. Pathology, 1-9; Li, 2004, Journal of Urology 171, 1782-1787; Wadsworth, 2004, Clinical Cancer Research, 10, 1625-1632; Prieto, 2003, Journal of Liquid Chromatography & Related Technologies 26, 2315-2328; Coombes, 2003, Clinical Chemistry 49, 1615-1623; Mian, 2003, Proteomics 3, 1725-1737; Lehre et al., 2003, BJU International 92, 223-225; and Diamond, 2003, Journal of the American Society for Mass Spectrometry 14, 760-765, which are hereby incorporated by reference in their entireties.

Other Types of Gene Abundance Measurements

The methods of the invention are applicable to any cellular constituent that can be monitored. For example, where activities of proteins can be measured, embodiments of this invention can use such measurements. Activity measurements can be performed by any functional, biochemical, or physical means appropriate to the particular activity being characterized. Where the activity involves a chemical transformation, the cellular protein can be contacted with the natural substrate(s), and the rate of transformation measured. Where the activity involves association in multimeric units, for example association of an activated DNA binding complex with DNA, the amount of associated protein or secondary consequences of the association, such as amounts of mRNA transcribed, can be measured. Also, where only a functional activity is known, for example, as in cell cycle control, performance of the function can be observed. However known and measured, the changes in protein activities form the response data analyzed by the foregoing methods of this invention.

In some embodiments of the present invention, cellular constituent measurements are derived from cellular phenotypic techniques. One such cellular phenotypic technique uses cell respiration as a universal reporter. In one embodiment, 96-well microtiter plate, in which each well contains its own unique chemistry is provided. Each unique chemistry is designed to test a particular phenotype. The biological sample (e.g., tissue sample, cell sample) from the organism of interest are pipetted into each well. If the sample exhibits the appropriate phenotype, it will respire and actively reduce a tetrazolium dye, forming a strong purple color. A weak phenotype results in a lighter color. No color means that the cells don't have the specific phenotype. Color changes can be recorded as often as several times each hour. During one incubation, more than 5,000 phenotypes can be tested. See, for example, Bochner et al., 2001, Genome Research 11, p. 1246, which is hereby incorporated by reference in its entirety.

In some embodiments of the present invention, the cellular constituents that are measured are metabolites. Metabolites include, but are not limited to, amino acids, metals, soluble sugars, sugar phosphates, and complex carbohydrates. Such metabolites can be measured, for example, at the whole-cell level using methods such as pyrolysis mass spectrometry (Irwin, 1982, *Analytical Pyrolysis: A Comprehensive Guide*, Marcel Dekker, New York; Meuzelaar et al., 1982, *Pyrolysis Mass Spectrometry of Recent and Fossil Biomaterials*, Elsevier, Amsterdam, each of which is hereby incorporated by reference in its entirety), fourier-transform infrared spectrometry (Griffiths and de Haseth, 1986, *Fourier transform infrared spectrometry*, John Wiley, New York; Helm et al., 1991, J. Gen. Microbiol. 137, 69-79; Naumann et al., 1991, Nature 351, 81-82; Naumann et al., 1991, In: *Modern techniques for rapid microbiological analysis*, 43-96; and Nelson, W. H., ed., VCH Publishers, New York, each of which is hereby incorporated by reference in its entirety), Raman spectrometry, gas chromatography-mass spectroscopy (GC-MS) (Fiehn et al., 2000, Nature Biotechnology 18, 1157-1161, which is hereby incorporated by reference in its entirety), capillary electrophoresis (CE)/MS, high pressure liquid chromatography/mass spectroscopy (HPLC/MS), as well as liquid chromatography (LC)-Electrospray and cap-LC-tandem-electrospray mass spectrometries. Such methods can be combined with established chemometric methods that make use of pattern classification algorithms (e.g., artificial neural networks, genetic programming) in order to discriminate between closely related samples.

Exemplary Normalization Routines

A number of different normalization protocols can be used to normalize gene abundance data 44. Some such normalization protocols are described in this section. Typically, the normalization comprises normalizing the expression level measurement of each gene in a plurality of genes that is expressed by an organism in a population of interest. Many of the normalization protocols described in this section are used to normalize microarray data. It will be appreciated that there are many other suitable normalization protocols that may be used in accordance with the present invention. All such protocols are within the scope of the present invention. Many of the normalization protocols found in this section are found in publicly available software, such as Microarray Explorer (Image Processing Section, Laboratory of Experimental and Computational Biology, National Cancer Institute, Frederick, Md. 21702, USA).

One normalization protocol is Z-score of intensity. In this protocol, raw expression intensities are normalized by the (mean intensity)/(standard deviation) of raw intensities for all spots in a sample. For microarray data, the Z-score of intensity method normalizes each hybridized sample by the mean and standard deviation of the raw intensities for all of the spots in that sample. The mean intensity $mnI_i$ and the standard deviation $sdI_i$ are computed for the raw intensity of control genes. It is useful for standardizing the mean (to 0.0) and the range of data between hybridized samples to about −3.0 to +3.0. When using the Z-score, the Z differences ($Z_{diff}$) are computed rather than ratios. The Z-score intensity (Z-score$_{ij}$) for intensity $I_{ij}$ for probe i (hybridization probe, protein, or other binding entity) and spot j is computed as:

$$Z\text{-score}_{ij} = (I_{ij} - mnI_i)/sdI_i,$$

and $$Zdiff_j(x,y) = Z\text{-score}_{xj} - Z\text{-score}_{yj}$$

where x represents the x channel and y represents the y channel.

Another normalization protocol is the median intensity normalization protocol in which the raw intensities for all spots in each sample are normalized by the median of the raw intensities. For microarray data, the median intensity normalization method normalizes each hybridized sample by the median of the raw intensities of control genes (medianI$_i$) for all of the spots in that sample. Thus, upon normalization by the median intensity normalization method, the raw intensity $I_{ij}$ for probe i and spot j, has the value $Im_{ij}$ where, $$Im_{ij} = (I_{ij}/\text{median}I_i).$$

Another normalization protocol is the log median intensity protocol. In this protocol, raw expression intensities are normalized by the log of the median scaled raw intensities of representative spots for all spots in the sample. For microarray data, the log median intensity method normalizes each hybridized sample by the log of median scaled raw intensities of control genes (medianI$_i$) for all of the spots in that sample. As used herein, control genes are a set of genes that have reproducible accurately measured expression values. The value 1.0 is added to the intensity value to avoid taking the log(0.0) when intensity has zero value. Upon normalization by the median intensity normalization method, the raw intensity $I_{ij}$ for probe i and spot j, has the value $Im_{ij}$ where, $$Im_{ij} = \log(1.0 + (I_{ij}/\text{median}I_i)).$$

Yet another normalization protocol is the Z-score standard deviation log of intensity protocol. In this protocol, raw expression intensities are normalized by the mean log intensity (mmLI$_i$) and standard deviation log intensity (sdLI$_i$). For microarray data, the mean log intensity and the standard deviation log intensity is computed for the log of raw intensity of control genes. Then, the Z-score intensity $Z \log S_{ij}$ for probe i and spot j is:

$$Z \log S_{ij}=(\log(I_{ij})-mnLI_i)/sdLI_i.$$

Still another normalization protocol is the Z-score mean absolute deviation of log intensity protocol. In this protocol, raw expression intensities are normalized by the Z-score of the log intensity using the equation (log(intensity)−mean logarithm)/standard deviation logarithm. For microarray data, the Z-score mean absolute deviation of log intensity protocol normalizes each bound sample by the mean and mean absolute deviation of the logs of the raw intensities for all of the spots in the sample. The mean log intensity $mnLI_i$ and the mean absolute deviation log intensity $madLI_i$ are computed for the log of raw intensity of control genes. Then, the Z-score intensity $Z \log A_{ij}$ for probe i and spot j is:

$$Z \log A_{ij}=(\log(I_{ij})-mnLI_i)/ madLI_i.$$

Another normalization protocol is the user normalization gene set protocol. In this protocol, raw expression intensities are normalized by the sum of the genes in a user defined gene set in each sample. This method is useful if a subset of genes has been determined to have relatively constant expression across a set of samples. Yet another normalization protocol is the calibration DNA gene set protocol in which each sample is normalized by the sum of calibration DNA genes. As used herein, calibration DNA genes are genes that produce reproducible expression values that are accurately measured. Such genes tend to have the same expression values on each of several different microarrays. The algorithm is the same as user normalization gene set protocol described above, but the set is predefined as the genes flagged as calibration DNA.

Yet another normalization protocol is the ratio median intensity correction protocol. This protocol is useful in embodiments in which a two-color fluorescence labeling and detection scheme is used. In the case where the two fluors in a two-color fluorescence labeling and detection scheme are Cy3 and Cy5, measurements are normalized by multiplying the ratio (Cy3/Cy5) by medianCy5/medianCy3 intensities. If background correction is enabled, measurements are normalized by multiplying the ratio (Cy3/Cy5) by (medianCy5-medianBkgdCy5)/(medianCy3-medianBkgdCy3) where medianBkgd means median background levels.

In some embodiments, intensity background correction is used to normalize measurements. The background intensity data from a spot quantification programs may be used to correct spot intensity. Background may be specified as either a global value or on a per-spot basis. If the array images have low background, then intensity background correction may not be necessary.

Computation of eQTL eQTL for each gene for which abundance data is available can be computed using quantitative trait locus (QTL) analysis. For example, in the case in which there are 1,000 genes for abundance data is available, the result is 1,000 separate eQTL analyses. In one example, each eQTL analysis steps through the genome of the organism of interest. Linkages to the gene under consideration are tested at each step or location along the length of the genome. In such embodiments, each step or location along the length of the chromosome is at regularly defined intervals. In some embodiments, these regularly defined intervals are defined in Morgans or, more typically, centiMorgans (cM). In other embodiments, each regularly defined interval is less than 10 cM, less than 5 cM, or less than 2.5 cM.

Figure 8:
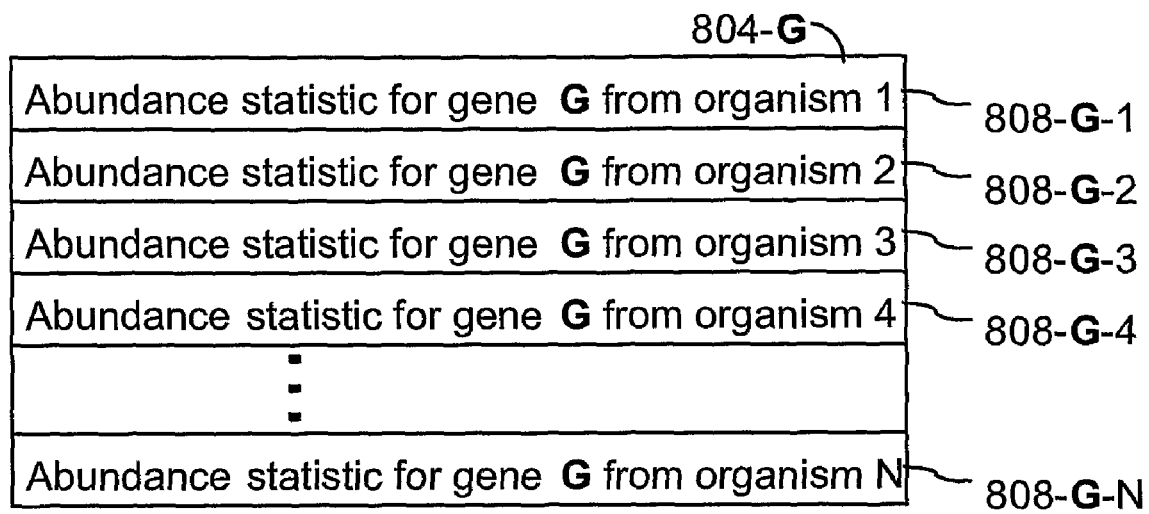
FIG. 8 illustrates a data structure for storing gene abundance data in accordance with one embodiment of the present invention.

In each eQTL analysis, abundance data for, or corresponding to, a gene i for which eQTL data is sought, is used as a quantitative trait. More specifically, for any given gene G, the quantitative trait used in the eQTL analysis is an abundance statistic set for the gene G. Such data includes abundance data for the gene G from each organism in the population under study. FIG. 8 illustrates an exemplary abundance statistic set 804 in accordance with one embodiment of the present invention. The exemplary abundance statistic set 804 of FIG. 8 includes the abundance level of gene G (or cellular constituent that corresponds to gene G) from each organism in a plurality of organisms. For example, consider the case where there are ten organisms in the plurality of organisms, and each of the ten organisms expresses gene G. In this case, the abundance statistic set includes ten entries, each entry corresponding to a different one of the ten organisms in the plurality of organisms. Further, each entry represents the abundance level (e.g., expression level) of gene Gin the organism represented by the entry. So, entry "1" (808-G-1) corresponds to the abundance level of gene G in organism 1, entry "2" (808-G-2) corresponds to the abundance level of gene G in organism 2, and so forth.

In one embodiment of the present invention, a QTL analysis for a given gene G comprises: (i) testing for linkage between a position in a genome and an abundance statistic set 804 (plurality of abundance statistics 808), (ii) advancing the position in the genome by an amount (e.g., less than 100 cM, less than 5 cM, greater than 100 cM), and (iii) repeating steps (i) and (ii) until the entire genome is tested. In some embodiments, testing for linkage between a given position in the genome and the abundance statistic set 804 comprises correlating differences in the abundance found in the abundance level statistic with differences in the genotype at the given position using single marker tests (for example using t-tests, analysis of variance, or simple linear regression statistics). See, e.g., *Statistical Methods*, Snedecor and Cochran, 1985, Iowa State University Press, Ames, Iowa, which is hereby incorporated by reference in its entirety. However, there are many other methods for testing for linkage between abundance statistic set 804 and a given position in the chromosome. In particular, if abundance statistic set 804 is treated as the phenotype (in this case, a quantitative phenotype), then methods such as those disclosed in Doerge, 2002, Mapping and analysis of quantitative trait loci in experimental populations, *Nature Reviews: Genetics* 3:43-62, which is hereby incorporated by reference in its entirety, may be used. Concerning steps (i) through (iii) above, if the genetic length of a given genome is N cM and 1 cM steps are used, then N different tests for linkage are performed.

In some embodiments, the eQTL data produced from each respective eQTL analysis comprises a logarithm of the odds score (lod) computed at each position tested in the genome under study. A lod score is a statistical estimate of whether two loci are likely to lie near each other on a chromosome and are therefore likely to be genetically linked. In the present case, a lod score is a statistical estimate of whether a given position in the genome under study is linked to (correlated with) the quantitative trait corresponding to a given gene. Lod scores are further defined in Section 5.7, below. In some embodiments, a lod score of 2.0 or more is generally taken to indicate that two loci are genetically linked. In some embodiments, a lod score of 3.0 or more is generally taken to indicate that two loci are genetically linked. In some embodiments, a lod score of 4.0 or more, 5.0 or more, or 6.0 or more is generally taken to indicate that two loci are genetically linked. The generation of lod scores generally requires pedigree data. Accordingly, in embodiments in which a lod score is generated, computation of an eQTL linkage analysis, as described in Lynch and Walsh, 1998, *Genetics and Analysis of Quantitative Traits*, Sinauer Associates, Inc. Sunderland Mass., hereby incorporated by reference in its entirety, with the exception that the quantitative trait under study is derived from data, such as cellular constituent expression statistics, rather than classical phenotypes such as eye color.

In situations where pedigree data is not available, genotype data from each of the organisms in the population can be compared to each abundance statistic set 804 using allelic association analysis, as described in Lynch and Walsh, 1998, *Genetics and Analysis of Quantitative Traits*, Sinauer Associates, Inc. Sunderland Mass., hereby incorporated by reference in its entirety, in order to identify QTL that are linked to (correlated with) each expression statistic set 804. In one form of association analysis, an affected population is compared to a control population. In particular, haplotype or allelic frequencies in the affected population are compared to haplotype or allelic frequencies in a control population in order to determine whether particular haplotypes or alleles occur at significantly higher frequency amongst affected compared with control samples. Statistical tests such as a chi-square test are used to determine whether there are differences in allele or genotype distributions.

Figure 9:
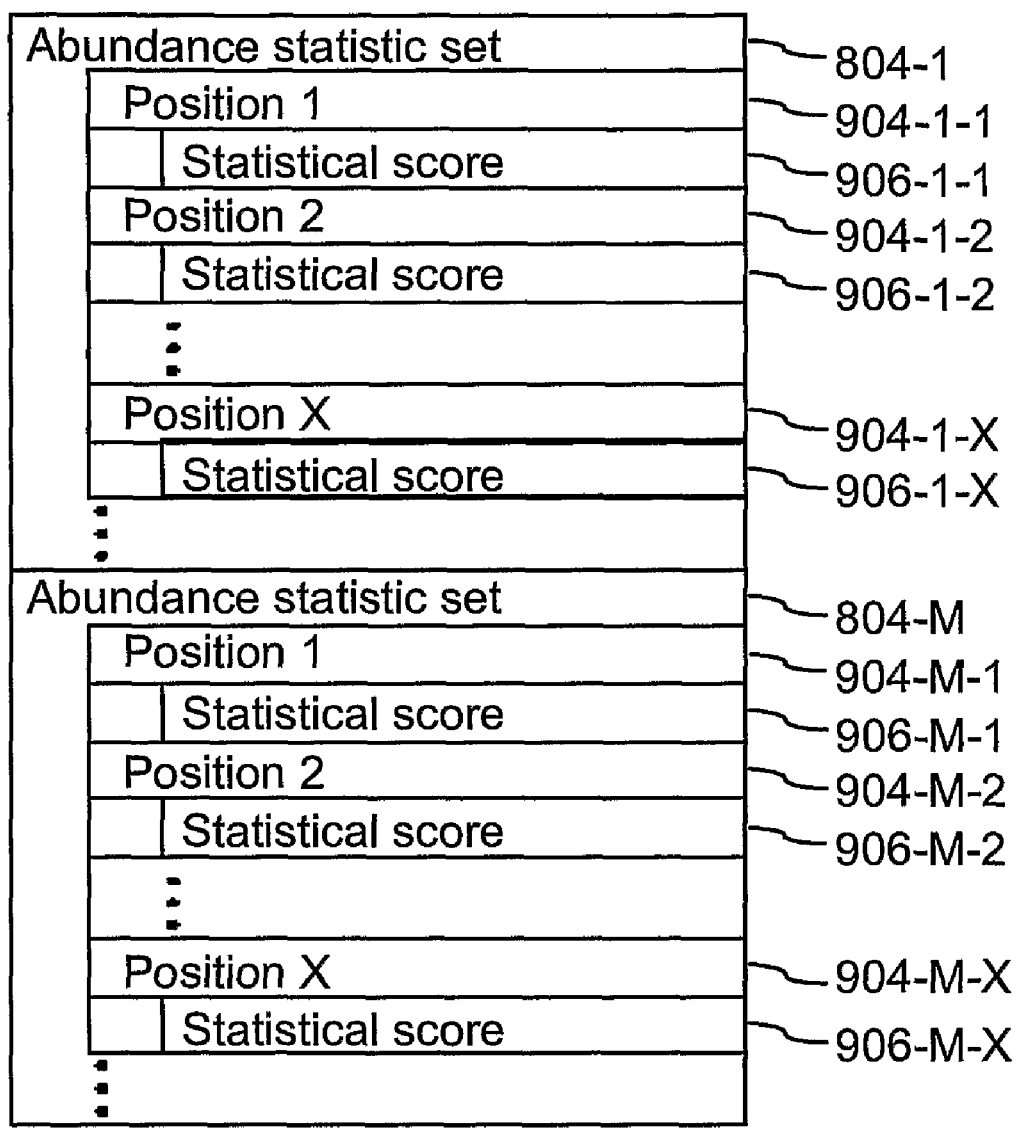
FIG. 9 illustrates an eQTL results database in accordance with the present invention.

Regardless of whether linkage analysis or association analysis is used, the results of each QTL analysis can be stored in a QTL results database 900 (FIG. 9) as an eQTL vector. QTL results database 900 can be stored in memory 36 of computer 10 (FIG. 1, not shown). For each abundance statistic set 804 (FIG. 8), QTL results database 900 comprises an eQTL vector which, in turn, comprises all tested positions 904 in the genome of the organism that were tested for linkage to the quantitative trait (expression statistic 804) and, for each position 904, a statistical measure (e.g., statistical score 906), such as the maximum lod score between the position and the abundance statistic 804. Thus, data structure 900 comprises all the positions in the genome of the organism of interest that are genetically linked to (correlated with) each abundance statistic 804 tested.

Logarithm of the Odds Scores

Denoting the joint probability of inheriting all genotypes P(g), and the joint probability of all observed data x (trait and marker species) conditional on genotypes P(x|g), the likelihood L for a set of data is $L = \Sigma P(g) P(x|g)$ where the summation is over all the possible joint genotypes g (trait and marker) for all pedigree members. What is unknown in this likelihood is the recombination fraction θ, on which P(g) depends.

The recombination fraction θ is the probability that two loci will recombine during meioses. The recombination fraction θ is correlated with the distance between two loci. By definition, the genetic distance is defined to be infinity between the loci on different chromosomes (nonsyntenic loci), and for such unlinked loci, θ=0.5. For linked loci on the same chromosome (syntenic loci), θ<0.5, and the genetic distance is a monotonic fraction of θ. See, e.g., Ott, 1985, *Analysis of Human Genetic Linkage*, first edition, Baltimore, Md., John Hopkins University Press, which is hereby incorporated by reference in its entirety. The essence of linkage analysis is to estimate the recombination fraction θ and to test whether θ=0.5. When the position of one locus in the genome is known, genetic linkage can be exploited to obtain an estimate of the chromosomal position of a second locus relative to the first locus. In linkage analysis, QTL analysis is used to map the unknown location of genes predisposing to various quantitative phenotypes relative to a large number of marker loci in a genetic map. In the ideal situation, where recombinant and nonrecombinant meioses can be counted unambiguously, θ is estimated by the frequency of recombinant meioses in a large sample of meioses. If two loci are linked, then the number of nonrecombinant meioses N is expected to be larger than the number of recombinant meioses R. The recombination fraction between the new locus and each marker can be estimated as:

$$\hat{\theta} = \frac{R}{N + R}$$

The likelihood of interest is:

$L = \Sigma P(g|\theta) P(x|g)$ and inferences are based about a test recombination fraction θ on the likelihood ratio $\nabla = L(\theta)/L(\frac{1}{2})$ or, equivalently, its logarithm.

Thus, in a typical clinical genetics study, the likelihood of the trait and a single marker is computed over one or more relevant pedigrees. This likelihood function L(θ) is a function of the recombination fraction θ between the trait (e.g., classical trait or quantitative trait) and the marker locus. The standardized loglikelihood $Z(\theta) = \log_{10}[L(\theta)/L(\frac{1}{2})]$ is referred to as a lod score. Here, "lod" is an abbreviation for "logarithm of the odds." A lod score permits visualization of linkage evidence. As a rule of thumb, in human studies, geneticists provisionally accept linkage if $Z(\hat{\theta}) \geq 3$ at its maximum θ on the interval [0,1/2], where $\hat{\theta}$ represents the maximum θ on the interval. Further, linkage is provisionally rejected at a particular θ if $Z(\hat{\theta}) \leq -2$.

However, for complex traits, other rules have been suggested. See, for example, Lander and Kniglyak, 1995, Nature Genetics 11, 241, which is hereby incorporated by reference in its entirety.

Acceptance and rejection are treated asymmetrically because, with 22 pairs of human autosomes, it is unlikely that a random marker even falls on the same chromosome as a trait locus. See Lange, 1997, *Mathematical and Statistical Methods for Genetic Analysis*, Springer-Verlag, New York; and Olson, 1999, Tutorial in Biostatistics: Genetic Mapping of Complex Traits, *Statistics in Medicine* 18, 2961-2981, each of which is hereby incorporated by reference in its entirety.

When the value of L is large, the null hypothesis of no linkage, L(½), to a marker locus of known location can be rejected, and the relative location of the locus corresponding to the quantitative trait can be estimated by $\hat{\theta}$. Therefore, lod scores provide a method to calculate linkage distances as well as to estimate the probability that two genes (and/or QTLS) are linked.

Those of skill in the art will appreciate that lod score computation is species dependent. For example, methods for computing the lod score in mouse different from that described in this section. However, methods for computing lod scores are known in the art and the method described in this section is only by way of illustration and not by limitation.

Kits

One embodiment of the present invention provides a computer and/or a computer program product encoding instructions for obtaining an eQTL vector for a gene X in a plurality of genes and instructions for obtaining an eQTL vector for a gene Y in this plurality of genes. The eQTL vectors can be obtained in a number of different ways. For example, the data can be obtained from input data, formed directly from measurement data, retrieved from memory (e.g., memory 36 or disk 14 of FIG. 6), and/or obtained a remote system. Furthermore, the eQTL vectors can be obtained from a database that is stored locally (e.g., memory 36 or disk 14 of FIG. 6) or stored in a remote system accessible, for example, through Internet 34 (FIG. 6). The computer and/or computer program product further stores instructions for constructing a prior p(X→Y) that represents a probability that gene X is upstream of gene Y in a biological pathway, wherein $$p(X \to Y) = r(X, Y) \frac{N(Y)}{N(X) + N(Y)},$$

wherein
N(Y) is a number of eQTL in the eQTL vector for the gene Y;
N(X) is a number of eQTL in the eQTL vector for the gene X; and
r(X,Y) is a weight that represents a correlation between the eQTL vector for the gene X and the eQTL vector for the gene Y.

The computer and/or computer program product further stores instructions for computing a model of a biological pathway using Bayesian analysis that incorporates this prior p(X→Y).

Another embodiment of the present invention provides a computer program product and/or computer that stores instructions for obtaining an eQTL vector for a gene X in a plurality of genes; and instructions for obtaining an eQTL vector for a gene Y in this plurality of genes. The eQTL vectors can be obtained in a number of different ways. For example, the data can be obtained from input data, formed directly from measurement data, retrieved from memory (e.g., memory 36 or disk 14 of FIG. 6), and/or obtained a remote system. Furthermore, the eQTL vectors can be obtained from a database that is stored locally (e.g., memory 36 or disk 14 of FIG. 6) or stored in a remote system accessible, for example, through Internet 34 (FIG. 6). The computer program product and/or computer further stores instructions for constructing a prior p(X→Y) that represents a probability that gene X is upstream of gene Y in a biological pathway, wherein $p(X \to Y) = 0$ when
(i) there is an eQTL in the eQTL vector for the gene Y that is coincident with the physical location of gene Y; and
(ii) there is an eQTL in the eQTL vector for the gene X that is coincident with the physical location of gene Y.

The computer program product further stores instructions for computing a model of a biological pathway using Bayesian analysis that incorporates the prior p(X→Y).

Still another embodiment of the present invention provides a computer program product and/or a computer system that stores instructions for obtaining a plurality of eQTL vectors, where each eQTL vector represents a different gene in a plurality of genes. The eQTL vectors can be obtained in a number of different ways. For example, the data can be obtained from input data, formed directly from measurement data, retrieved from memory (e.g., memory 36 or disk 14 of FIG. 6), and/or obtained a remote system. Furthermore, the eQTL vectors can be obtained from a database that is stored locally (e.g., memory 36 or disk 14 of FIG. 6) or stored in a remote system accessible, for example, through Internet 34 (FIG. 6). The computer program product and/or computer further comprises instructions for computing, for each respective eQTL vector in the plurality of eQTL vectors, a correlation between the respective eQTL vector and the eQTL vector that represents gene Y, thereby obtaining a correlation coefficient for each gene in the plurality of genes with respect to gene Y. The computer program product and/or computer further comprises instructions for ranking the plurality of genes by correlation coefficient with respect to gene Y thereby forming a ranked list of genes that includes a gene X. The computer program product and/or computer further comprises instructions for constructing a prior p(X→Y) that represents a probability that gene X is upstream of a gene Y in the biological pathway, where $p(X \to Y) = 0$ when the correlation coefficient for gene X is below a threshold percentile in the ranked list of genes. The computer program product and/or computer further comprises instructions for computing a model of a biological pathway using Bayesian analysis that incorporates the prior p(X→Y).

Still another aspect of the invention provides a computer program product and/or computer system that comprises instructions for obtaining a plurality of eQTL vectors, where each eQTL vector represents a different gene in a plurality of genes. The eQTL vectors can be obtained in a number of different ways. For example, the data can be obtained from input data, formed directly from measurement data, retrieved from memory (e.g., memory 36 or disk 14 of FIG. 6), and/or obtained a remote system. Furthermore, the eQTL vectors can be obtained from a database that is stored locally (e.g., memory 36 or disk 14 of FIG. 6) or stored in a remote system accessible, for example, through Internet 34 (FIG. 6). The computer program product and/or computer further stores instructions for computing, for each respective eQTL vector in the plurality of eQTL vectors, a measure of mutual information between the respective eQTL vector and the eQTL vector that represents gene Y, thereby obtaining a mutual information score for each gene in the plurality of genes with respect to gene Y. The computer program product and/or computer further stores instructions for ranking the plurality of genes by mutual information score with respect to gene Y thereby forming a ranked list of genes that includes a gene X. The computer program product and/or computer further stores instructions for constructing a prior p(X→Y) that represents a probability that gene X is upstream of a gene Y in the biological pathway, wherein $p(X \to Y) = 0$ when the mutual information score for gene X is below a threshold percentile in the ranked list of genes. The computer program product and/or computer further stores instructions for computing a model of a biological pathway using Bayesian analysis that incorporates the prior p(X→Y).

EXAMPLES

Experimental Design and Data Collection

The F2 mouse population and gene expression data used in this study have been previously described by Drake et al., 2001, Physiol Genomics 5: 205-15; and Schadt et al., 2003, Nature 422: 297-302, each of which is hereby incorporated by reference in its entirety. Briefly, an F2 population consisting of 111 mice was constructed from two inbred strains of mice, C57BL/6J and DBA/2J. Only female mice were maintained in this population. All mice were housed under conditions meeting the guidelines of the Association for Accreditation of Laboratory Animal Care. Mice were on a rodent chow diet up to twelve months of age, and then switched to an atherogenic high-fat, high-cholesterol diet for another four months. At sixteen months of age the mice were phenotyped and their livers extracted for gene expression profiling. The mice were genotyped at 139 microsatellite markers uniformly distributed over the mouse genome to allow for the genetic mapping of the gene expression and disease traits.

At the time of sacrifice, livers were removed from the F2 animals and RNA isolated for gene expression profiling, as described by Schadt et al., 2003, Nature 422: 297-302, which is hereby incorporated by reference. Prepared RNA from each F2 animal was hybridized against a pool of RNA, constructed from equal aliquots of RNA from each F2 animal, using a comprehensive 23,574 gene microarray manufactured by Agilent Technologies. In all, 18,131 genes gave rise to intensity measures that were significantly above the background noise (p-value<0.05). However, only 1088 of these genes were detected as significantly differentially expressed based on criteria that expression levels change at least 1.5 fold with an associated p-value less than 0.01 for at least 25% of the mice. These 1088 genes were used in the network reconstruction study and are referred to as the F2 data set.

To assess the accuracy of the predicted network and further refine it, a perturbation experiment was performed on Ppara. Ppara is one of the 1088 genes in the network constructed from the F2 data set, and perturbations in Ppara activity can be seen to down-regulate Hsd11b1. Nineteen male C57BL/6J mice between the ages of 10 and 13 weeks were used in the experiment. The following three treatments were administered orally for seven days: 1) six mice treated with 200 mpk of Fenofibrate, six mice treated with 30 mpk of WY-14643, and 3) seven mice treated as vehicle controls. After the seven day treatment regimen, which allowed the mice to reach a new steady state with respect to Ppara activity, all mice were sacrificed and RNA was extracted from the livers of each animal for profiling on gene expression microarrays. RNA from randomly formed pairs of animals in the treatment groups was pooled, resulting in three replicate RNA samples for each treatment group. These RNA samples were hybridized against a pool of RNA constructed from equal aliquots of RNA from each control mouse using microarrays manufactured by Agilent Technologies (Palo Alto, Calif.).

Network Reconstruction Using Bayesian Networks

Forming candidate relationships among genes was carried out using an extension of standard Bayesian network reconstruction methods. See Friedman et al., 2000, Journal of Computational Biology 7, 601-620, which is hereby incorporated by reference in its entirety. In the extension of these methods, QTL information was incorporated for the transcript abundances of each gene considered in the network.

It is well known that searching for the best possible network linking a moderately sized set of genes is an NP-hard problem. Exhaustively searching for the optimal network with hundreds of genes is presently a computationally intractable problem. Therefore, various simplifications are typically applied to reduce the size of the search space and to reduce the number of parameters that need to be estimated from the data. Here two simplifying assumptions were employed to achieve such reductions. First, it was assumed that while any gene in a biological system can control many other genes, a given gene was not allowed to be controlled by more than three genes. Second, only a subset of candidate genes was allowed to be considered as possible causal drivers (parent nodes) for a given gene, instead of allowing for the possibility of any gene in the complete gene set to be so considered.

Selection of potential parents for each gene. To select potential parents for each gene a strategy to assess the extent of genetic overlap between any two gene expression traits was employed. If RNA levels for two genes are tightly associated, or if such levels are genetically controlled by a similar set of loci, then their eQTL should overlap. The genome-wide eQTL computed by Schadt et al. (2003) was used to determine whether any two genes in the 1088 gene set had overlapping eQTL. The extent of QTL overlap was measured by computing the correlation coefficient between vectors of LOD scores associated with eQTL identified over entire chromosomes for each gene. If no epistasis between eQTL is assumed for a given expression trait, then the eQTL can be considered independent between chromosomes, and a measure of genetic relatedness over all chromosomes for any two traits can be subsequently computed as a weighted average of correlations for each individual chromosome using the weighting scheme described in step 708 in Section 5.1 "Parental test A." For each gene, the correlation coefficients described in step 708 in Section 5.1 "Parental test A," was computed for all genes in the set of 1088 genes of interest, and the $80^{th}$ percentile of the rank-ordered list of correlations was arbitrarily chosen as the cutoff for genes to be considered as parental nodes in the network for a given gene of interest.

In some embodiments, for each gene, the mutual information score described in step 708 in Section 5.1 "Parental test B," was computed for all genes in the set of 1088 genes of interest. Specifically, as was done for the correlation calculations, the mutual information measure was computed for all gene pairs in the F2 data set, and again this list was rank ordered and those genes in the $80^{th}$ percentile were chosen as candidate parental nodes for a given gene of interest.

The selection of a given gene that appears in both the $80^{th}$ percentile of the rank-ordered list generated from the correlation measure and the $80^{th}$ percentile of the rank-ordered list generated from the mutual information measure provides the prior evidence that a given gene is causally related to the gene for which a parent gene is sough. The QTL data provide the causal anchors that allow this type of inference to be made. That is, by definition, a QTL controlling for the expression of two gene expression traits implies that DNA variations in the QTL lead to variations in the expression of the associated gene traits. Therefore, it should be the case that any gene expression trait pair controlled by a common QTL is either 1) independently driven by the same QTL, or 2) causally associated in that one of the two traits is driven by the QTL, while the other trait responds to the trait driven by the QTL. The conditional mutual information measure, described below, helps to resolve which of these cases holds.

Integration of QTL information into the network reconstruction process. In addition to utilizing the QTL information as prior information to restrict the types of relationships that can be established among genes, the QTL information can be more intimately integrated into the network reconstruction process. Because correlation measures are symmetric, they can indicate association but not causality. However, as indicated above, QTL mapping information for the gene expression traits can be used to help sort out causal relationships as well. Thus, priors $p(X \rightarrow Y)$, where X and Y are genes in the plurality of genes for which a gene network reconstruction is sought, were weighed by complexity in the manner described for step 710 in Section 5.1. Specifically, the prior p(X→Y) was weighted by:

$$p(X \rightarrow Y) = r(X, Y) \frac{N(Y)}{N(X) + N(Y)},$$

where N is a gene expression trait's complexity as measured by the number of significant eQTL mapped for the given gene expression trait. The conditional mutual information measure discussed below served to prevent, in at least some cases, causal links from being made between genes that were independently driven by a common set of QTL.

Consideration of cis-acting genes. The causality relationships between gene expression traits can be further assessed by considering whether the QTL for a particular gene expression trait is cis-acting. If a gene expression trait X has an eQTL at locus L that is coincident with the gene's physical location, it can be stated that the gene has a cis-acting eQTL at L. This relationship indicates it is likely that DNA variations in the gene itself at least partially explain variations in the gene's observed RNA levels. Therefore, the inference can be made that a gene with a cis-acting eQTL is at least partially under the control of the gene itself. In this particular situation, where another gene expression trait Y has an eQTL mapping to the physical location of the cis-acting gene X, the inference can be made that X may be causal for Y, and that Y is likely not causal for X. As a result, when this condition holds we set p(Y→X) equal to 0 in accordance with step 712 of Section 5.1

Construction of a graphical model. With the various constraints and measures defined above, a graphical model M (a gene network) that best represents the relationships between genes, given a gene expression data set, D, of interest, was sought The algorithm employed to search through all possible models to find the network that best fits the data is similar to the local maximum search algorithm implemented by Friedman et al., 2000, J Computational Biology 7, 601-620, which is hereby incorporated by reference in its entirety.

Exploratory Clustering in the Gene Expression and QTL Dimensions

Figure 1B:
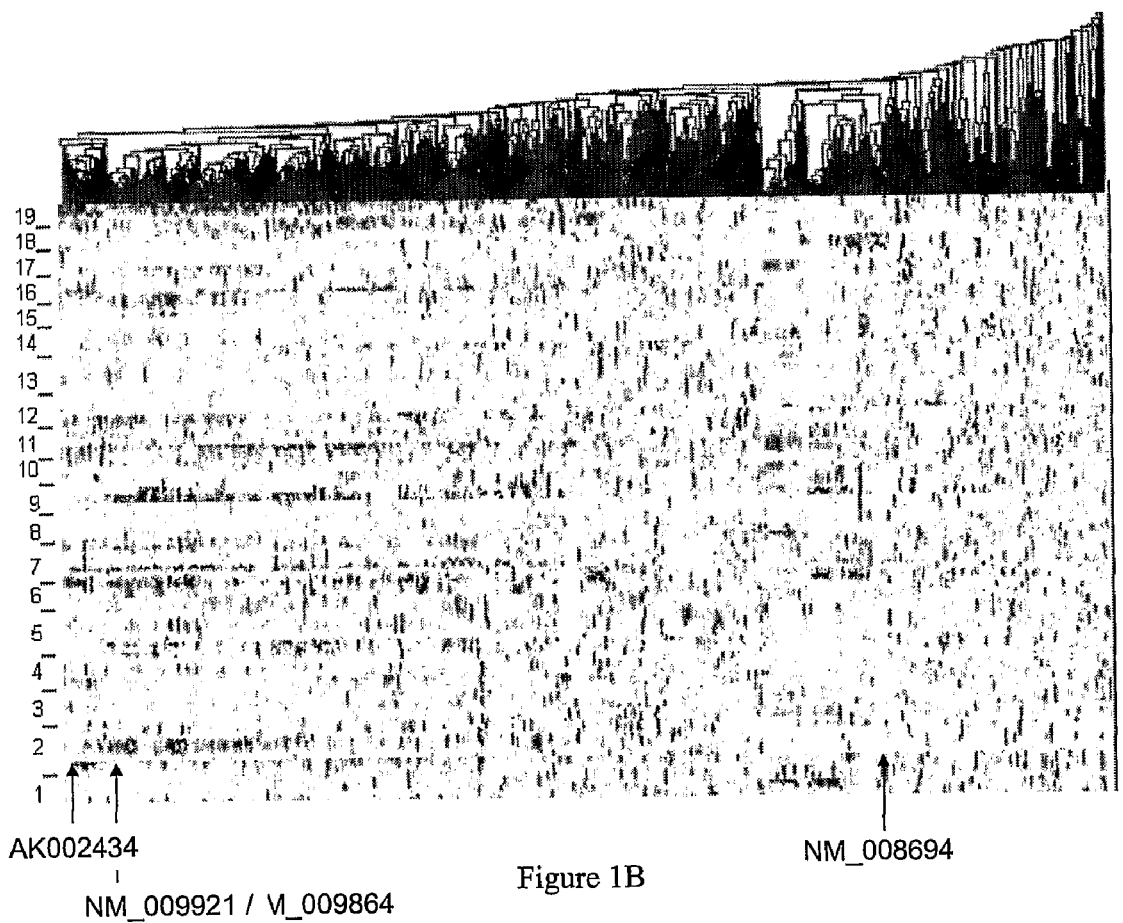
FIG. 1 illustrates hierarchical clustering of the F2 data set in the gene expression and eQTL dimensions. (A) Matrix display of cluster results in the gene expression and experiment dimensions. The horizontal and vertical axes represent the gene expression and experiment dimensions, respectively. Four genes that cluster tightly together are highlighted. (B) Matrix display of cluster results in the QTL dimension, given along the horizontal axis. The vertical axis is ordered according to chromosomal location. Each element of the matrix represents a LOD score for a given gene expression trait at a given chromosomal location. The four genes highlighted in (A) are also highlighted in this plot. While these four genes grouped tightly together in the expression cluster, NM_009864 does not group well with the other three genes in the eQTL dimension, indicating the genetic component of NM_009864 does not contribute significantly to the overall correlation structure between this gene and the other three genes.

Similarities for the transcript abundances of the 1088 genes in the F2 data set were broadly assessed using hierarchical clustering in the gene expression and eQTL dimensions. FIG. 1A depicts hierarchical clustering results for the gene expression and experiment dimensions, where the Pearson correlation measure on relative transcript abundances was used as the similarity metric, as described by Schadt et al., 2003, Nature 422: 297-302, which is hereby incorporated by reference in its entirety. FIG. 1B depicts the hierarchical clustering results in the eQTL dimension, where in this case the similarity metric used is the correlation measure defined in equation (1).

From FIG. 1A it is noted that the relatively tight associations among the genes that break the mice roughly into two general groups. From the eQTL clustering in FIG. 1B, it is apparent there is no preferred grouping of the genes, but instead genes driven by the same set of QTL, which can be seen as the bright bands running along the chromosome-location axis of the display matrix, appear to group most tightly together. That is, while genes that are highly correlated group together in the standard gene expression cluster shown in FIG. 1A, for eQTL clustering those genes driven by common genetic loci are more closely associated, indicating that the genetic component of the overall correlation structure between all gene expression trait pairs may give different preferred orderings, thereby highlighting different relationships among genes that are not apparent from the gene expression data alone. For example, NM_009921 (Camp) and NM_008694 (Ngp) are genes involved in defense response that are seen to cluster together in FIGS. 1A and 1B, indicating at least part of the correlation structure between these two genes is due to shared genetic components. However, AK002434 (Krt27) and NM_009864 (Cdh1) cluster together in FIG. 1A, but are spatially separated in FIG. 1B, indicating their correlation structure was largely a consequence of non-genetic components. These genetic relationships among genes were exploited, in addition to the raw gene expression relationships, to reconstruct gene networks.

Consensus Networks

The 1088 genes in the F2 data set were input into a Bayesian network program written in the C++ programming language and based on the reconstruction algorithm described above. A total of 1000 networks were reconstructed based on this set of genes and a consensus network was derived from this set of networks by identifying links between gene pairs that existed in more than 40% of the networks. Each link was assigned a confidence value corresponding to the number of times it appeared in the 1000 networks considered. Cycles in the resulting consensus network were broken by removing links in the cycle associated with the lowest confidence values.

Starting with the consensus network, identification of the most parsimonious model given the data was sought using the maximum likelihood method described above. Although priors for network structure were introduced to penalize more complex topologies, there was still a chance that optimal networks derived from this process over fit the data. To lessen the likelihood that the resulting networks in fact over fit the data, links in the network were removed to simplify relationships among genes using a conditional information measure. For instance, if the type of sub-network shown in FIG. 2 was found to exist in the larger network, the conditional mutual information between B and C was computed to determine whether B and C were still found to be dependent given information on node A. The conditional mutual information in this instance is given by equation (9) in Section 5.1, above. Using equation (9), if MI(B,C|A) were not significantly different from 0, then the determination was made that the link B→C can be safely removed. Pearl, 1988, *Probablistic Reasonsing In Intelligent Systems Networks of plausible Inference*, Morgan Kaufmann Publishers, Inc., San Francisco, Calif., which is hereby incorporated by reference, provides more details on this type of procedure.

After removing links causing cycles and links that lead to over fitting of the data, the resulting consensus network contained links for 909 genes. Interestingly, there were 179 genes that did not have any links in the network, suggesting these 179 genes were not informative for this network reconstruction problem. Clustering the expression values for these 179 genes (data not shown) indicated there were no clear patterns of expression that distinguished the mice in any meaningful way. One explanation for the lack of strong association between these 179 genes and the other 909 genes in the F2 data set could be that these 179 genes were an artifact of the microarray experiments.

Assessing the Significance of Predicted Networks

To determine whether the network reconstruction method involving expression and QTL data in a segregating population leads to optimal networks that possess greater predictive power than similar networks derived from the expression data alone, a series of comparisons were performed. First, after fitting the model to the F2 data, a goodness of fit test was used to assess whether the model fit the independent Ppara agonist data set well. Second, a determination was made as to whether the model was able to predict the expression response for a given gene perturbed in the independent Ppara agonist data set. Finally, a comparison was made of the predictive power of (i) the model of the present invention based on the combined gene expression/QTL data with (ii) a more basic model based on expression data alone.

Goodness of fit. The assessment of the goodness of fit of a model on a particular set of data using the likelihood P(D|M), where D represents the data and M the model (e.g., those models fitting the data better will yield a higher likelihood score). Here two model types were considered: 1) M1 based on the expression data alone, and 2) M2 based on the genotypic data as well as the expression data. Given relative transcript abundances for the 1088 genes in the F2 data set as measured in the 6 Ppara agonist treated mouse pairs, a comparison was made of (i) the likelihoods of the optimal networks identified for each model type and (ii) the likelihoods generated for each model type based on 1000 random permutations of the gene states. The resulting z-scores for these tests for each of the Ppara agonist treated mouse pairs were computed and are given in Table 2.

One experiment that assesses the predictive power of the Hsd11b1 sub-networks for each model type is the perturbation of the activity of Hsd11b1 directly in an independent mouse model in order to identify the set of genes that change in response to inhibiting Hsd11b1 activity. This gene set could then be compared to the predictions made from the networks of each type (M1 and M2). Since no genome-wide liver expression profiles exist in the public domain from Hsd11b1 knock out or Hsd11b1 inhibitor treated animals, this type of comparison was not directly performed. However, Hsd11b1 was seen to be down-regulated in the Ppara agonist experiments described above, a result that is consistent with those reported by Yamazaki et al., 2002, Biochem Biophys Res Commun 290, 1114-1122, which is hereby incorporated by reference in its entirety.

In addition to being regulated by fatty acids, Ppara's expression is also regulated by glucocorticoid. See Kroetz et al. 1998, Journal Biologlical Chemistry 273, 31581-31589, which is hereby incorporated by reference in its entirety. Because Hsd11b1 converts cortisone to cortisol, which in turn binds to glucocorticoid receptors, Ppara can also fall under the control of Hsd11b1. Therefore, it is expected that gene expression signatures induced by perturbations to Hsd11b1 and Ppara overlap given this connection between them. Pck1 and G6 pc were reported to change in Hsd11b1 knock out mice compared to wildtype. See Kotelevtsev et al., 1997,

TABLE 2

Goodness of fit statistics for the two model types described in the text.

| Network\Z-score | $F^1$ Pair 1 | $F^1$ Pair 2 | $F^1$ Pair 3 | $W^2$ Pair 1 | $W^2$ Pair 2 | $W^2$ Pair 3 |
|---|---|---|---|---|---|---|
| Network without genetics (M1) | 8.50 | 9.95 | 9.07 | 9.88 | 10.17 | 8.75 |
| Network with genetics (M2) | 7.67 | 8.71 | 8.19 | 8.78 | 9.85 | 8.75 |

[1]Fenofibrate treated
[2]WY-14,643 treated

Both model types are seen to fit the experimental data well, with a p-value less than $8.7\ e^{-15}$ reported for the best fits.

Figure 3A:
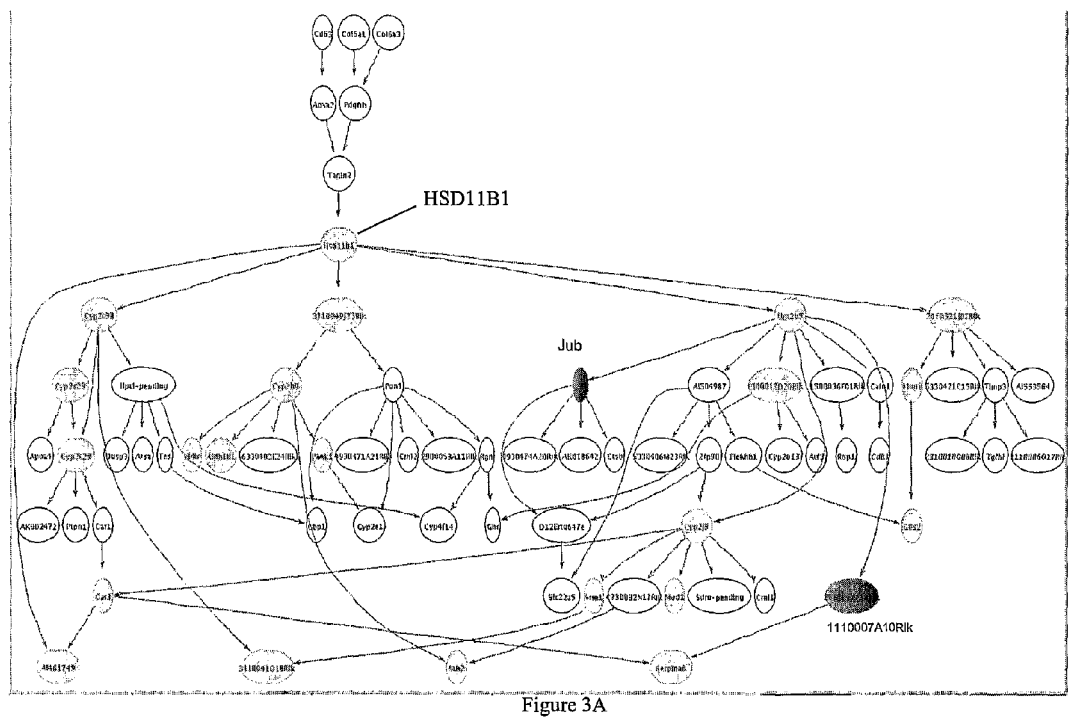
FIG. 3 illustrates a M2-type sub-networks associated with Hsd11b1. (A) The predicted sub-network centered at the Hsd11b1 node. The nodes (genes) making up this sub-network were identified by requiring that they have a path to Hsd11b1 no longer than three links. The gene expression state of each node is shaded according to the predicted state when Hsd11b1 is in the down-regulated state. Light shading indicates a gene is up-regulated relative to the reference pool, dark shading indicates a gene is down-regulated relative to the reference pool, and no fill indicates a gene is not differentially expressed relative to the reference pool. (B) An Hsd11b1 sub-network related to the sub-network given in (A). This sub-network is defined by those nodes in the complete network whose gene expression is predicted to change given the down-regulated state of Hsd11b1. Pictured here are the predicted expression states of 33 genes, given Hsd11b1 is in the down-regulated state. The stars indicate the 20 genes represented in the Ppara signature.

This goodness of fit test demonstrates that the expression levels of different genes are related, as seen in FIG. 1, and that Bayesian networks (or general graphic models) can well capture these inter-gene relationships. However, the more important question is whether the pathways inferred from these reconstructions are able to capture causal information reliably. If a network truly captures the state of a biological system, it should be able to identify which genes will change when a given gene is perturbed in the system. One of the genes represented in the optimal networks identified for each model type was Hsd11b1. FIG. 3A represents the sub-network derived from the M2 network by restricting attention to nodes that were within a path of length three to the Hsd11b1 node (e.g., an Hsd11b1-centered sub-network showing nodes that are "close" to the Hsd11b1 node). The Hsd11b1 sub-network indicates that Hsd11b1 plays a key regulatory role in the network, given it is controlled by relatively few genes and ultimately controls a large number of genes. This sub-network is of further interest because Hsd11b1 is significantly correlated with fat pad masses, insulin levels, leptin levels, cholesterol levels and other related phenotypes collected on the F2 mice making up the F2 data set. See, for example, Drake et al., 2001, Physiol Genomics 5, 205-215; Colinayo et al., 2003, Mamm Genome 14, 464-471; and Schadt et al. 2003, Nature 422, 297-302, each of which is hereby incorporated by reference in its entirety.

Proceedings National Academy of Science U.S.A. 94, 14924-14929, which is hereby incorporated by reference in its entirety.

Pck1 and G6 pc were also reported to change in Hsd11b1 inhibitor treated mice, compared to untreated mice. See, Alberts et al., 2002, Diabetologia 45, 1528-1532; and Alberts et al., 2003, Endocrinology 144: 4755-4762, which are hereby incorporated by reference in their entireties. In the Ppara agonist experiments described here, G6 pc and Pck1 were down regulated, providing direct confirmation that the Hsd11b1 and Ppara perturbation signatures overlap.

Figure 3B:
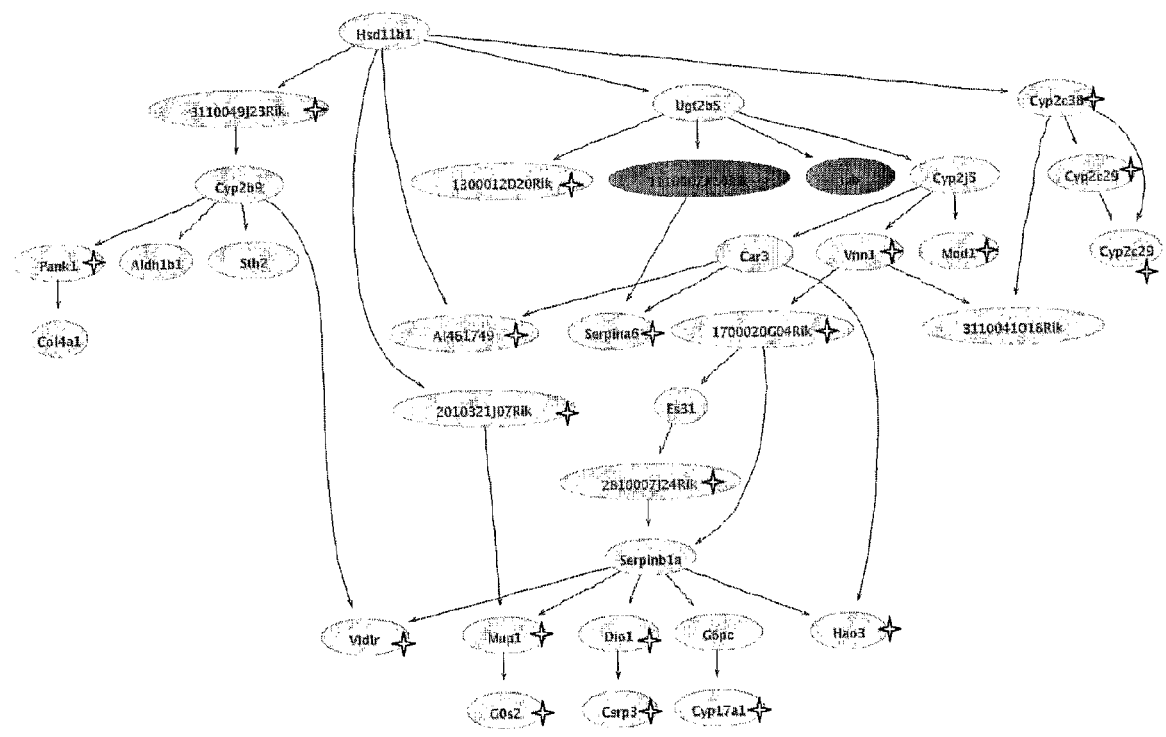

There were 1206 genes identified in the Ppara gene expression signature, and 322 of these overlapped the 1088 making up the F2 data set. This overlap is statistically significant, given the p-value that this overlap could have occurred by chance is effectively equal to zero using the Fisher Exact Test. This significant overlap indicates that Ppara targeted genes in the F2 set explain a significant proportion of the transcriptional variation in the F2 mice. Next those genes predicted by the network to change in response to down regulation of Hsd11b1 expression were identified, since Hsd11b1 is down-regulated in the Ppara signature. For model type M2, the expression/QTL-based model, there were 33 genes predicted by the network to change in response to changes in Hsd11b1, as shown in FIG. 3B. Of the 33 genes predicted to change, 20 overlapped the set of 322 genes in the Ppara agonist signature. The statistical significance of this overlap can be assessed using the Fisher Exact Test. The p-value for the null hypothesis that the overlap between the genes predicted to change by the network and the genes observed to change in response to down regulation of Hsd11b1 by the Ppara agonist, was approximately 1.7e(−4). It is of note that one of the two expression markers for Hsd11b1 inhibition identified by Alberts et al., 2002, Diabetologia 45, 1528-1532, G6 pc, was similarly predicted by the network in FIG. 3B to be down-regulated in response to Hsd11b1 inhibition. The other marker, Pck1, did not have a valid probe represented on the microarray used to generate the F2 data set, so the gene was not in the set of 1088 genes used to construct the network. On the other hand, only five genes were predicted to change by the best network of type M1 (the model based on the expression data alone) identified from the reconstruction process, and three of these overlapped the set of 322 Ppara influenced genes (p-value=0.16). These results clearly indicate that model type M2 has superior prediction capabilities compared to model M1, which does no better than would be expected by chance.

These tests demonstrate that network models based on gene expression and QTL data are better able to capture causal relationships. While both model types well capture interaction data, only the genetics-based model was able to capture causal relationships in a statistically significant way. It is of further note that the genes most causally associated with Hsd11b1 are not necessarily from the set of genes whose RNA levels are most correlated with Hsd11b1 RNA levels. For example, the top 33 genes in the network most correlated with Hsd11b1 yield a minimum coefficient of determination equal to 0.836. Thirteen of these top 33 most correlated and anti-correlated genes actually overlap the Ppara agonist signature (p-value=0.15). This again demonstrates that association based on expression data alone does not yield the causal information required to order pathways.

Sub-Networks and Cis-Acting QTL

The QTL data not only allow for stronger causal inferences to be made in the type of network reconstruction problem described above, these data also provide gene-specific perturbation information that can be utilized to identify genes affected by other genes, as highlighted for Hsd11b1. While genes with cis-acting eQTL likely have polymorphisms in the gene itself that result in variations in RNA levels, these causative polymorphisms will also lead to changes in the RNA levels of other genes, much in the same way that knock outs, transgenics and siRNA experiments targeting a particular gene lead to changes in the expression of other genes responding to the perturbation. The DNA variations provide definitive causal information that is useful in reconstructing pathways.

Of the 1088 genes in the F2 data set, 108 had cis-acting eQTL. Here, the term cis-acting eQTL means an eQTL located within 15 cM of the physical location of the gene and having an associated LOD score greater than 10. Of these 108 genes, 44 had children in the network, while 13 had more than 10 children, as shown in Table 3. Two of the genes represented in this table, Tcea3 and Isgf3g, are transcription-factor related genes. This functional role potentially explains why these two genes were identified as controlling for the expression of many other genes in the predicted network. In Table 3, column 1, entitled "Name," are the National Center for Biotechnology Information (NCBI) Genbank accession numbers, Nucleic Acids Research 32, (2004), 23-26, for the listed genes.

TABLE 3

Summary of the top 12 genes with the most children in the full M2.

| Name | Number of children | Symbol | Description |
| --- | --- | --- | --- |
| AJ251685 | 623 | Gpnmb | glycoprotein (transmembrane) nmb |
| AK018527 | 583 | 9030425 E11Rik | adipocyte-specific protein 5 |
| NM_026158 | 477 | 0610042 E07Rik | RIKEN Gene |
| AF345951 | 413 | Dusp16 | dual specificity phosphatase 16 |
| AI662255 | 291 | AI662255 | CYTOCHROME P450 2c40 |
| NM_018881 | 138 | Fmo2 | flavin containing monooxygenase 2 |
| NM_008394 | 56 | Isgf3g | interferon dependent positive acting transcription factor 3 gamma |
| AK017566 | 41 | Zdhhc2 | zinc finger, DHHC domain containing 2 |
| NM_007799 | 21 | Ctse | cathepsin E |
| NM_019393 | 20 | Pmsc11 | polymyositis/scleroderma autoantigen 11 |
| AK002319 | 19 | Tcea3 | transcription elongation factor A (SII), 3 |
| NM_008620 | 12 | Mpa2 | macrophage activation 2 |

The sequence of each gene listed in Table 3 is hereby incorporated by reference in its entirety.

As discussed above, it is known that one of the functional roles of Hsd11b1 is to convert cortisone to cortisol. Cortisol acts as an immunosuppressor by reducing T cell proliferation, reducing complement synthesis, and increasing the rate of B cell death. See, for example, Weyts et al., 1998, Dev Comp Immunol 22, 551-62, which is hereby incorporated by reference. Therefore, while it is expected that genes associated with immune response vary in response to perturbations in Hsd11b1, it is also expected that these immune response genes would be under the control of many other biochemical and physiological processes in a genetically more diverse setting, like that which exists in an F2 population. Therefore it is expected that genes downstream of the immune response processes are harder to link to Hsd11b1 expression in the network reconstruction process.

Figure 4:
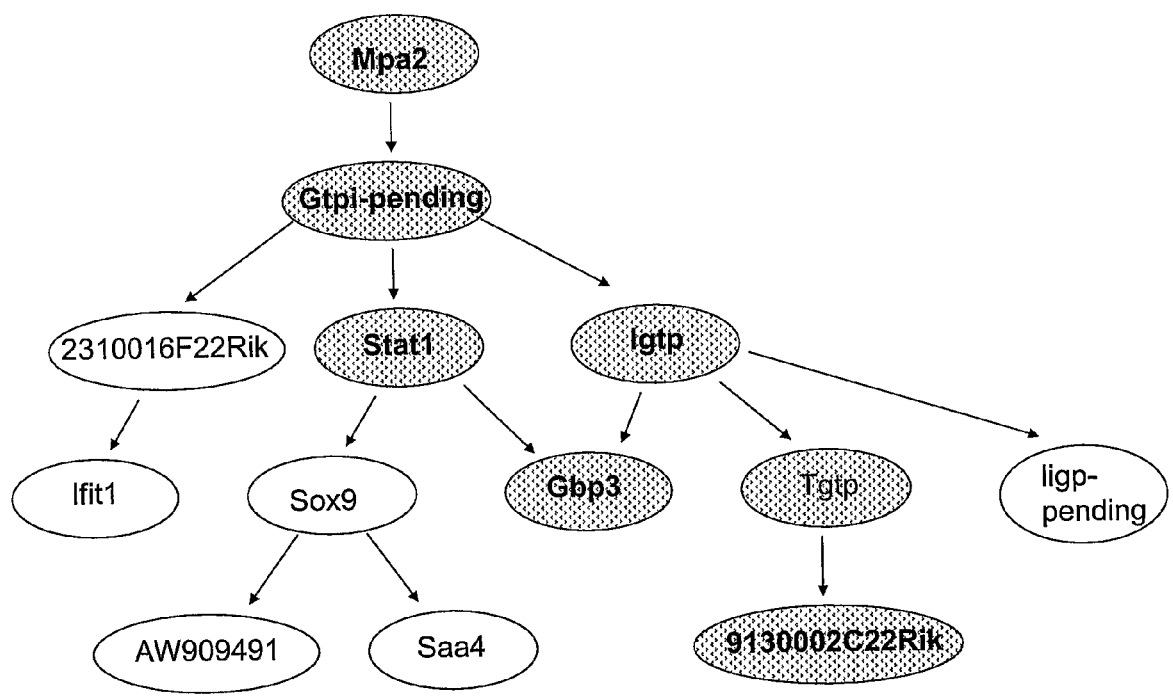
FIG. 4 illustrates a sub-network of Mpa2 (NM_008620). The predicted states for genes responding to Mpa2 when Mpa2 is up-regulated. Hatched ovals indicates the gene is unregulated, and no fill indicates no expression change relative to the reference pool.

As an example, consider the sub-network associated with guanylate-binding protein Mpa2, which is induced by interferon-gamma during macrophage induction. See Nguyen et al., 2002, J Interferon Cytokine Res 22, 899-909, which is hereby incorporated by reference in its entirety. However, there are many biochemical and physiological steps sitting between down regulating Hsd11b1, the subsequent decrease of cortisol, and the ultimate increase in T cell proliferation, which in turn results in the induction of Mpa2. Because the F2 mice were on an atherogenic diet, many of the transcriptionally active genes in the liver were associated with immune response. The sub-network associated with Mpa2 is given in FIG. 4. Table 4 lists the twelve genes that are given as nodes in FIG. 4. In Table 4, column 1, entitled "Name," are the National Center for Biotechnology Information (NCBI) Genbank accession numbers, Nucleic Acids Research 32, (2004), 23-26, for the listed genes.

TABLE 4

Genes controlled by MPA2 in the full M2 network.
Genes with an asterisk are predicted to change
when MPA2 is in the up-regulated state.

| Name | Symbol | Description |
|---|---|---|
| NM_019440* | Gtpi | interferon-g induced GTPase |
| AK018544* | Stat1 | signal transducer and activator of transcription 1 |
| AK009386 | 2310016F22Rik | RIKEN cDNA 2310016F22 gene |
| NM_018738* | Igtp | interferon gamma induced GTPase |
| NM_021792 | Iigp | interferon-inducible GTPase |
| BC004064 | Sox9 | SRY-box containing gene 9 |
| NM_018734* | Gbp3 | guanylate nucleotide binding protein 3 |
| NM_011579* | Tgtp | T-cell specific GTPase |
| NM_008331 | Ifit1 | interferon-induced protein with tetratricopeptide repeats 1 |
| AK018585* | 9130002C22Rik | RIKEN cDNA 9130002C22 gene |
| AW909491 | | hypothetical protein MGC41320 |
| NM_011316 | Saa4 | Serum amyloid A 4 |

The sequence of each gene listed in Table 4 is hereby incorporated by reference in its entirety.

Six of the genes are predicted to respond when Mpa2 is in the up-regulated state, and these genes can be seen to be involved in immune response functions. Therefore, from the Hsd11b1 and Mpa2 sub-networks, it is noted that the complexity of the immune response in the F2 data set results in a failing to link HSD11B1 as a driver of Mpa2 expression, most likely because of a diversity of immune response pathways that are active in this data set and that are unaffected by HSD11B1 activity. This example helps explain why a larger fraction of genes that may be under the control of HSD11B1 were not identified as being under the control of HSD11B1 in the sub-network predicted from the F2 data set.

Linkage Disequilibrium (LD) as a Confounding Factor in the Reconstruction of Gene Networks The network reconstruction procedures described here are strongly dependent on the correlation structures observed between gene expression traits and the associated pattern of overlapping eQTL to establish causal relationships. Any factors influencing these correlation structures, but that are independent of the actual functional relationships of interest between any two genes, could be expected to impact the structure of a predicted network. Perhaps the most striking example of such a confounding effect in an F2 population is linkage disequilibrium. Linkage disequilibrium (LD), or gametic phase disequilibrium, is a concept that describes the association of alleles across two or more loci. For example, consider two loci A and B with alleles (A1/A2 and B1/B2) that are polymorphic between two parental strains used to construct an F2 cross. Further suppose these two loci are physically proximal on the same chromosome. Then, it is expected that haplotypes A1B1 (or A1B2) and A2B2 (or A2B1) will be seen more often than haplotypes A1B2 and A2B1, since there would be few recombinations observed between these two genes, in an F2 population, given their close proximity. This type of effect is very pronounced in an F2 intercross, given all animals obtain from a single F1 founder, with only two meiotic events separating any two mice in the F2 population. If DNA variations at both loci cause variations in the RNA levels for the two genes, then the correlation structure between these RNA levels will be at least partially explained by gametic phase disequilibrium, as opposed to being explained by meaningful functional relationship between the genes.

Figure 5:
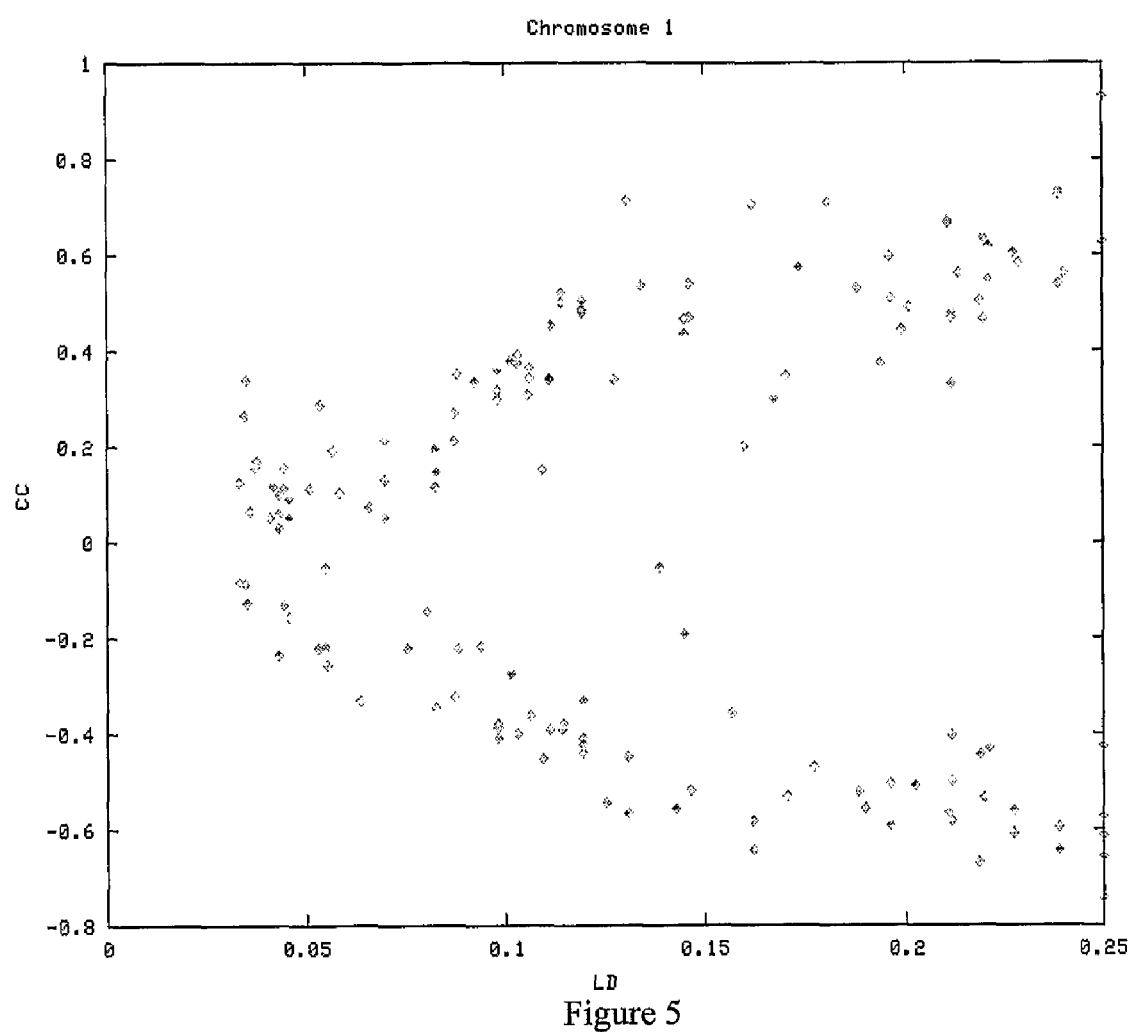
FIG. 5 illustrates pairwise correlations of mRNA levels as a function of gametic phase disequilibrium between the associated genes. Twenty genes physically residing on chromosome 1 were identified with strong cis-acting eQTL from an eQTL analysis on the F2 data set described in the main text. Pearson correlation coefficients were computed for the mean log expression ratios between each of the 190 pairs of genes. Each of the correlations was plotted against the linkage disequilibrium values corresponding to each gene pair. The pattern in this plot indicates that the magnitude of correlation is directly proportional to the linkage disequilibrium values, a relationship that is expected if the correlation structures were largely attributed to linkage disequilibrium.

While this issue has been well studied, the practical consequences of it have never before been observed in the context of tens of thousands of gene expression traits. As an example of how the correlation structure between two genes can be almost fully explained by linkage disequilibrium, all genes on chromosome 1 with cis-acting eQTL with LOD scores over 10.0, as given by Schadt et al., 2003, Nature 422, 297-302, are considered. FIG. 5 depicts a plot of all pairwise correlations between the transcript abundances of these genes as a function of linkage disequilibrium (LD). From this figure it is apparent that the correlations between these genes are largely a consequence of 1) being under strong genetic cis-acting control, and 2) being in LD with other genes that are under strong cis-acting genetic control. The practical consequence of this confounding effect in the context of network reconstruction can be seen as follows. Suppose that variations in the expression of gene g1 cause changes in the expression of gene g3, that g1 is physically close to gene g2, and that both g1 and g2 have strong cis-acting eQTL. Given this scenario, depending on the strength of the cis-acting eQTL and the genetic distance between them, it could be difficult to identify whether g1 or g2 was causal for g3, since g1 and g2 could be potentially significantly correlated. As a result, the relationship g2→g3 as well as the true relationship g1→g3 may be recovered due to the effect of LD.

Refinement Based on Additional Experiments

Because there are only 111 experiments in the F2 data set from which the 1088 nodes (genes) in the network were derived, there is the possibility that the network over fits the data. Even though priors were added to constrain the network topology based on QTL information, there are still many networks that fit the data equally well when the topologies between these different directed networks are similar. In addition, some links established in the reconstruction process may be due to the type of LD confounding effects just described. To refine the structure of a given network we can either integrate more data into the reconstruction process or design additional experiments to refine the causal relationships.

By incorporating additional experimental evidence, a given network can be updated to reflect the information the additional experiments provide, which may then result in better discriminating power to identify the best network out of the most likely network structures identified as part of the original reconstruction process. The Ppara agonist data can be used for these purposes. If a gene is in the Ppara agonist signature set, then the link between Hsd11b1 and this gene can be weighted with a higher prior probability to indicate Hsd11b1 activity may be causative for variations in the RNA levels of the gene. Applying the Ppara agonist data in this way, a refinement to the network given in FIG. 3 was obtained, fitted from the 1088 genes in the F2 data set. The refined network predicts 41 genes responding to Hsd11b1 in the down-regulated state, and 26 of these overlap with the Ppara signature, a statistically significant result with a p-value equal to 5.0e(−6). This overlap is even more significant than the results discussed for FIG. 3. These results further demonstrate the utility and flexibility of the Bayesian network approach in incorporating different data to elucidate pathway structures.

Discussion

To the inventors' knowledge, the first ever use of combined gene expression and genotypic data in a segregating population to reconstruct genetic networks has been described in this example. The method considers eQTL data in addition to gene expression data to constrain the possible types of relationships between any two genes in a system of interest, and then more formally integrates these data into classic Bayesian network reconstruction methods. The experiments above demonstrated that the network reconstruction algorithm is able to represent causal relationships among genes by validating predictions made from networks derived from the F2 data set, using the independent Ppara agonist data set. It has further been demonstrated that these same causal relationships could not be reliably inferred using existing expression based network reconstruction methods.

The methods based on Bayesian networks are better suited to study large global networks, compared to the dynamic modeling methods used to study small sub-networks such as described in Tegner et al., 2003, Proc Natl Acad Sci USA 100, 5944-5949. The structure of Bayesian networks can be automatically estimated from the data without any manual intervention. Also, predictions based on the fitted networks can be made in the context of the models developed herein. However, there are also limitations to the use of Bayesian networks to represent gene networks. First, Bayesian networks are acyclic, directed graphs, and so, they can not represent feedback loops. In a stable biological system, many processes are under negative feedback control, which presents difficulties in establishing causality since such loop structures cannot be represented using a Bayesian network. Further, if a gene's RNA levels are self-regulated, then these levels may vary in a narrow range, potentially resulting in only a marginally significant LOD score for the associated cis-acting eQTL. In this situation, without explicit information on the self-regulatory role of the gene, the potential exists for such a gene to be identified as a downstream responder of those genes that appear to be influencing its expression. For example, Ppara is selected as a downstream responder in the general network constructed from the 1088 genes in the F2 data set. However, Ppara knockout and agonist data suggest that Ppara may actually be causative for many of the genes falling upstream of it in the inventive network, given these genes are in the Ppara knockout and agonist gene expression signatures. Therefore, while the examples above demonstrate that eQTL information aids in sorting out causative relationships, ultimately additional data or more specific experimentation may be required to refine these relationships.

Despite these shortcomings, the significance of the predictions surrounding Hsd11b1 is encouraging, especially given the animals analyzed in the F2 and Ppara agonist experiments were genetically distinct and raised under dramatically different environmental conditions. Animals in the F2 set were more than one year old, all female, and they had been on a high-fat, atherogenic diet for sixteen weeks. Genetically, the chromosomes of the F2 mice are comprised of randomly assorted segments from the B6 and DBA inbred strains. Therefore, in the F2 data set, the observed variations in Hsd11b1 stem from a complicated mixture of extreme environmental conditions (given the atherogenic component of the diet) and different genetic backgrounds (each F2 animal represents a different genetic background), and with only 111 animals, the power to detect causal signals was likely minimal. On the other hand, the Ppara agonist experiment involved young, male mice (less than four months old) from a single genetic background under more natural environmental conditions, where just a single gene was strongly perturbed. Therefore, the extent of overlap between the genetic network and the Ppara signature set that was obtained is remarkable. The 26 genes in the overlap likely represent the key, most primary responders to Hsd11b1. Many of the other genes identified in the Ppara agonist experiment that did not overlap the network predictions may be the result of off-target effects and responders to these off-target effects, or they could represent more distant responders to the primary Hsd11b1 responders that are easily seen in a single gene perturbation experiment, but that get lost in the noise in a more complex, multifactorial perturbation experiment such as that achieved in an F2 cross. Additional experiments that involve directly perturbing Hsd11b1 can be conducted to better understand the Hsd11b1 mechanism of action and to better access the prediction accuracy of the Bayesian network approach presented.

Integrating genetic and genomic data using the Bayesian network algorithm developed here offers a promising approach to understanding the complex network of gene changes that are associated with complex traits, and that more generally underlie the complexity of living systems. The results presented in this example indicate that combining eQTL and gene expression information may allow for the possibility of ordering pathways associated with complex traits.

CONCLUSION

All references cited herein are incorporated herein by reference in their entirety and for all purposes to the same extent as if each individual publication or patent or patent application was specifically and individually indicated to be incorporated by reference in its entirety for all purposes.

What is claimed is:

1. A method for constructing a model of a biological pathway comprising a plurality of genes, the method comprising:
   (A) obtaining an eQTL vector for a gene X in said plurality of genes;
   (B) obtaining an eQTL vector for a gene Y in said plurality of genes;
   (C) constructing a prior p(X→Y) that represents a probability that said gene X is upstream of said gene Y in said biological pathway, wherein $$p(X \to Y) = r(X, Y) \frac{N(Y)}{N(X) + N(Y)},$$

wherein
   N(Y) is a number of eQTL in the eQTL vector for said gene Y;
   N(X) is a number of eQTL in the eQTL vector for said gene X; and
   r(X,Y) is a weight that represents a correlation between the eQTL vector for said gene X and the eQTL vector for said gene Y; and
   (D) computing said model of said biological pathway using Bayesian analysis that incorporates the prior p(X→Y) constructed in step (C), wherein said computing step is carried out on a suitably programmed computer.

2. The method of claim 1, wherein said plurality of genes is between 100 and 1000 genes.

3. The method of claim 1, wherein said plurality of genes is between 500 and 10,000 genes.

4. The method of claim 1, wherein said plurality of genes is between 1000 and 5,000 genes.

5. The method of claim 1, wherein each eQTL in the eQTL vector for said gene Y has a LOD score of 3.0 or more.

6. The method of claim 1, wherein each eQTL in the eQTL vector for said gene Y has a LOD score of 4.0 or more.

7. The method of claim 1, wherein each eQTL in the eQTL vector for said gene Y has a LOD score of 5.0 or more.

8. A computer program product for use in conjunction with a computer system, wherein the computer program product comprises a tangible, non-transitory computer readable storage medium on which computer-executable instructions are stored for implementing a method comprising:
  (A) obtaining an eQTL vector for a gene X in a plurality of genes;
  (B) obtaining an eQTL vector for a gene Y in said plurality of genes;
  (C) constructing a prior $p(X \rightarrow Y)$ that represents a probability that said gene X is upstream of said gene Y in said biological pathway, wherein $$p(X \rightarrow Y) = r(X, Y) \frac{N(Y)}{N(X) + N(Y)},$$

wherein
    N(Y) is a number of eQTL in the eQTL vector for said gene Y;
    N(X) is a number of eQTL in the eQTL vector for said gene X; and
    r(X,Y) is a weight that represents a correlation between the eQTL vector for said gene X and the eQTL vector for said gene Y; and
  (D) computing a model of a biological pathway using Bayesian analysis that incorporates the prior $p(X \rightarrow Y)$ constructed by said instructions for constructing (C).

9. A computer comprising:
  a central processing unit;
  a memory coupled to the central processing unit, the memory storing computer-executable instructions for implementing a method comprising:
    (A) obtaining an eQTL vector for a gene X in a plurality of genes;
    (B) obtaining an eQTL vector for a gene Y in said plurality of genes;
    (C) constructing a prior $p(X \rightarrow Y)$ that represents a probability that said gene X is upstream of said gene Y in said biological pathway, wherein $$p(X \rightarrow Y) = r(X, Y) \frac{N(Y)}{N(X) + N(Y)},$$

wherein
      N(Y) is a number of eQTL in the eQTL vector for said gene Y;
      N(X) is a number of eQTL in the eQTL vector for said gene X; and
      r(X,Y) is a weight that represents a correlation between the eQTL vector for said gene X and the eQTL vector for said gene Y; and
    (D) computing a model of a biological pathway using Bayesian analysis that incorporates the prior $p(X \rightarrow Y)$ constructed by said instructions for constructing (C).

* * * * *